(12) United States Patent
Fraser-Reid et al.

(10) Patent No.: US 7,741,475 B2
(45) Date of Patent: Jun. 22, 2010

(54) SYNTHESIS OF MONOVALENT AND POLYVALENT ARABINANS AND MANNOSE-CAPPED ARABINANS OF THE PROTECTIVE CELL-WALL COAT OF MYCOBACTERIUM TUBERCULOSIS

(75) Inventors: Bertram Fraser-Reid, Pittsboro, NC (US); Jun Lu, Cary, NC (US)

(73) Assignee: Natural Products & Glycotechnology Research Institute, Inc., Fearrington, NC (US)

( * ) Notice: Subject to any disclaimer, the term of this patent is extended or adjusted under 35 U.S.C. 154(b) by 314 days.

(21) Appl. No.: 11/674,287

(22) Filed: Feb. 13, 2007

(65) Prior Publication Data

US 2008/0015344 A1 Jan. 17, 2008

Related U.S. Application Data

(60) Provisional application No. 60/772,837, filed on Feb. 13, 2006.

(51) Int. Cl.
| | |
|---|---|
| C07H 1/00 | (2006.01) |
| C07H 3/00 | (2006.01) |
| C08B 37/00 | (2006.01) |
| C12P 19/04 | (2006.01) |
| C13K 5/00 | (2006.01) |
| C13K 7/00 | (2006.01) |

(52) U.S. Cl. ..................... 536/123; 536/124
(58) Field of Classification Search .................. None
See application file for complete search history.

(56) References Cited

OTHER PUBLICATIONS

Fraser Reid et al. Tetrahedron: Asymmetry 17 (2006) 2449-2463.*
Marotte et al. Eur. J. Org. Chem. 2003, 3587-3598.*
Turnbull et al. Angew. Chem. Int. Ed. 2004, 43, 3918-3922.*
Glatman-Freedman et al. Journal of Clinical Microbiology, Jul. 2004, p. 3225-3231.*
Gadikota et al. Journal of Carbohydrate Chemistry, vol. 22, Nos. 3 & 4, pp. 149-170, 2003.*
Lu et al. Organic Letters 2004, 6 (18), 3051-3054.*
Dyer et al., "Synthesis and Structure of Phosphatidylinositol Dimannoside," *J. Org. Chem*. 72:3282-3288 (2007).
Jayaprakash et al., "Regioselective Strategies Mediated by Lanthanide Triflates for Efficient Assembly of Oligomannans," *J. Org. Chem*. 72:5534-5545 (2007).
Zhang et al., "Characterization of a Distinct Arabinofuranosyltransferase in *Mycobacterium smegmatis*," *J. Am. Chem. Soc*. 129:9650-9662 (2007).
Borman. "Key Oligosaccharide of Cell Wall Prepared" *Chemical & Engineering News* 83(38):38 (2005).
Dao et al. "Mycobacterium tuberculosis Lipomannan Induces Apoptosis and Interleukin-12 Production in Macrophages" *Infection and Immunity* 72(4):2067-2074 (2004).
Gibson et al. "A Lipomannan Variant With Strong TLR-2-Dependent Pro-Infammatory Activity in *Saccharothrix aerocolonigenes*" *The Journal of Biological Chemistry* 280(31):28347-28356 (2005).
Gilleron et al. "*Mycobacterium smegmatis* Phosphoinositols-Glyceroarabinomannans" *The Journal of Biological Chemistry* 272(1):117-124 (1997).
Gilleron et al. "Mycobacterium tuberculosis H37Rv Parietal and Cellular Lipoarabinomannans" *The Journal of Biological Chemistry* 275(1):677-684 (2000).
Maeda et al. "The Cell Surface Receptor DC-SIGN Discriminates Between *Mycobacterium* Species Through Selective Recognition of the Mannose Caps on Lipoarabinomannan" *The Journal of Biological Chemistry* 278(8):5513-5516 (2003).
Nigou et al. "Lipoarabinomannans: From Structure to Biosynthesis" *Biochimie* 85:153-166 (2003).
Ziegler. "Protecting Group Strategies for Carbohydrates" in *Carbohydrate Chemistry*, Ed. Geert-Jan Boons, Blackie Academic & Professional, London, UK, pp. 21-45 (1998).

* cited by examiner

*Primary Examiner*—Shaojia Anna Jiang
*Assistant Examiner*—Layla Bland
(74) *Attorney, Agent, or Firm*—Myers Bigel Sibley & Sajovec, P.A.

(57) ABSTRACT

The present application provides arabinans and mannose-capped arabinan compositions of formulas I-VIII, described herein, and methods of making the compositions.

7 Claims, No Drawings

SYNTHESIS OF MONOVALENT AND POLYVALENT ARABINANS AND MANNOSE-CAPPED ARABINANS OF THE PROTECTIVE CELL-WALL COAT OF MYCOBACTERIUM TUBERCULOSIS

PRIORITY STATEMENT

This application claims the benefit, under 35 U.S.C. §119 (e), of U.S. Provisional Application No. 60/772,837, filed Feb. 13, 2006, the entire contents of which are incorporated by reference herein.

STATEMENT OF GOVERNMENT SUPPORT

This invention was made in the course of research sponsored by the National Science Foundation (NSF Grant No. CHE 0236946). The U.S. Government has certain rights in this invention.

FIELD OF THE INVENTION

The present invention concerns arabinans and mannose-capped arabinans, compositions thereof, and methods of making the compositions.

BACKGROUND OF THE INVENTION

Tuberculosis is a leading cause of morbidity and mortality worldwide with more than 8 million new cases per year and approximately 2 million deaths (World Health Organization. Tuberculosis. Fact Sheet No 104, 2004). In addition, approximately 1.86 billion people, a third of the world's population, are infected (Dye et al. *JAMA* 1999; 282:677-86). Tuberculosis is also a major cause of morbidity and mortality among children with an estimated annual death of 400,000 children in the developing countries (Kochi A. *Tubercle* 1992; 72:1-6). Infection acquired during childhood can serve as a reservoir for future illness, resulting in active disease during adolescence and adulthood.

The treatment of tuberculosis is complex, requiring the use of multiple medications for prolonged periods of time, in order to avoid the development of resistance. However, the demands of such regimens often result in poor compliance, and this has led to the emergence of multiple drug resistant (MDR) strains.

The dissemination of MDR tuberculosis in the population has the potential for high morbidity and mortality. Furthermore, tuberculosis is one of the main causes of death in AIDS patients, and so the AIDS epidemic coupled with the advent of MDR tuberculosis, pose a formidable threat to overcrowded populations centered in prisons, homeless shelters and such at-risk communities. However, since tuberculosis is air-borne, no segment of the world's population can be thoroughly insulated from it.

Directly observed therapy programs, established to address many of the difficulties associated with the care of infection and disease caused by *Mycobacterium tuberculosis*, were shown to be effective in certain areas of the world (Zumla et al. *Trans R Soc Trop Med Hyg* 1999; 93:113-7). However, such programs are costly and logistically complex (Id.) and may not be feasible in many parts of the world, particularly for underserved populations. Bacille Camette-Guérin (BCG), the only available vaccine against tuberculosis (TB) (Guerin C. The history of BCG. In: Rosenthal SR ed. Boston: Little, Brown & Co., 1957:48-53), was shown to prevent disseminated disease in young children but has not been effective in preventing pulmonary TB (Colditz et al., *JAMA* 1994; 271:698-702), which is the main form of TB. Furthermore, BCG is losing its efficacy against MDR strains. Considering the overwhelming problem of TB, the difficulties associated with its treatment, and the new potentially harmful prospects, there is an urgent need to develop more effective strategies for the prevention of TB.

SUMMARY OF THE INVENTION

The present invention relates to the field of complex glycans or lipoarabinomannan (LAM) compositions associated with *Mycobacterium* cell. More particularly, the present invention concerns the novel compounds, branched arabinans capped at the non-reducing end with mannose units, as well as procedures for making and using the arabinans and mannose-capped arabinans. These branched arabinans comprise the mannose-capped arabinan domain of the lipoarabinomannan structural component of the *Mycobacteria* cell wall. The mannose-capped arabinan domain has been identified as the most potent immunomodulatory factor of *Mycobacterium tuberculosis* (Glatman-Freedman et al., *J. Clin. Microbiol.* 2004; 42: 3225-3231; Hamasur et al., *Vaccine* 2003; 21:4081-93). Thus, the arabinans and mannose-capped arabinans and their subunits can be used for screening of compounds useful in the treatment of diseases caused by *Mycobacteria* (Stewart et al., *Nature Reviews Microbiology* 2003; 3: 97), as well as for eliciting an immune response, for enhancement of an immune response, as a vaccine, a vaccine adjuvant and as a potential drug candidate itself for treatment of such diseases as tuberculosis, leprosy, cancer, and asthma.

Accordingly, a first aspect of the invention is a compound of formula I:

I wherein n is an integer from 1 to 20; and
X is an attachment group;
or a salt thereof.

A second aspect of the present invention is a compound of formula II:

II wherein m and n are each independently an integer from 1 to 20; and
X is an attachment group;
or a salt thereof.
A third aspect of the present invention is a compound of formula III:
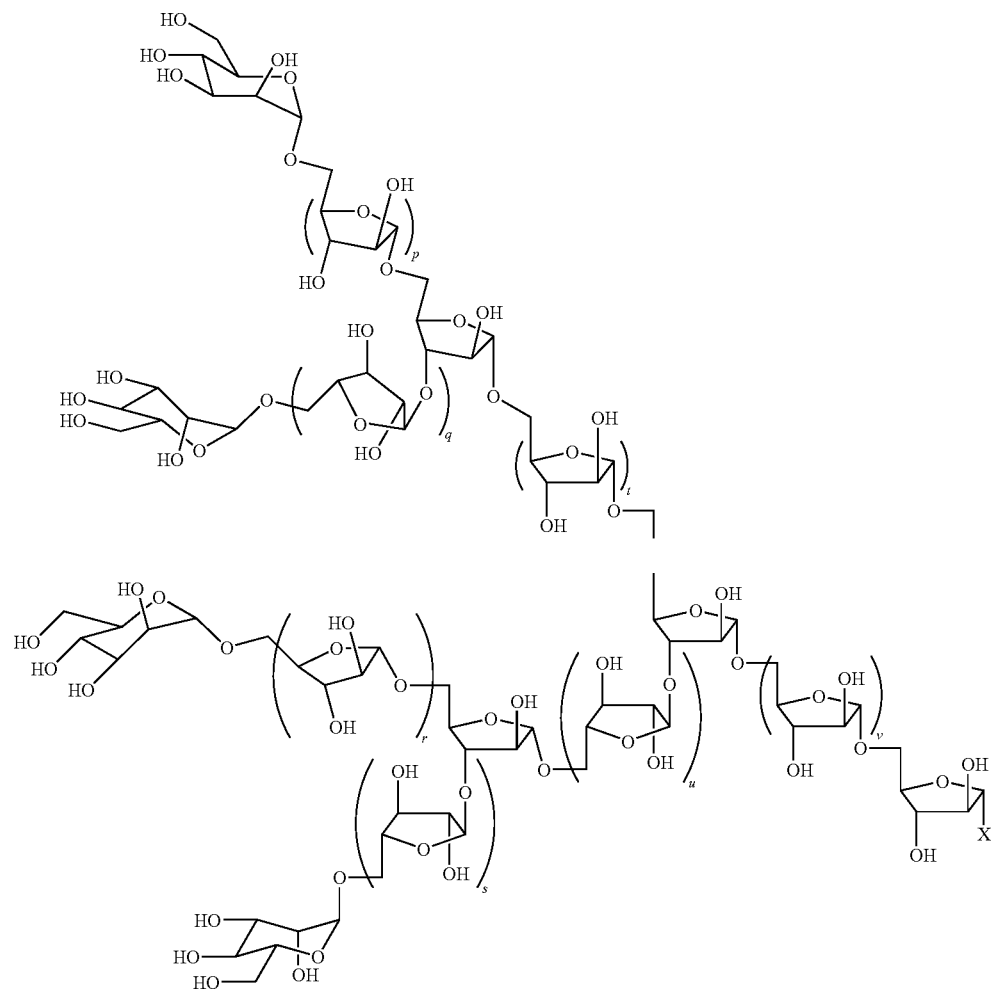
III
wherein p, q, r, s, t, u, and v are each independently an integer from 1 to 20; and
X is an attachment group;
or a salt thereof.

A fourth aspect of the present invention is a compound of formula IV:
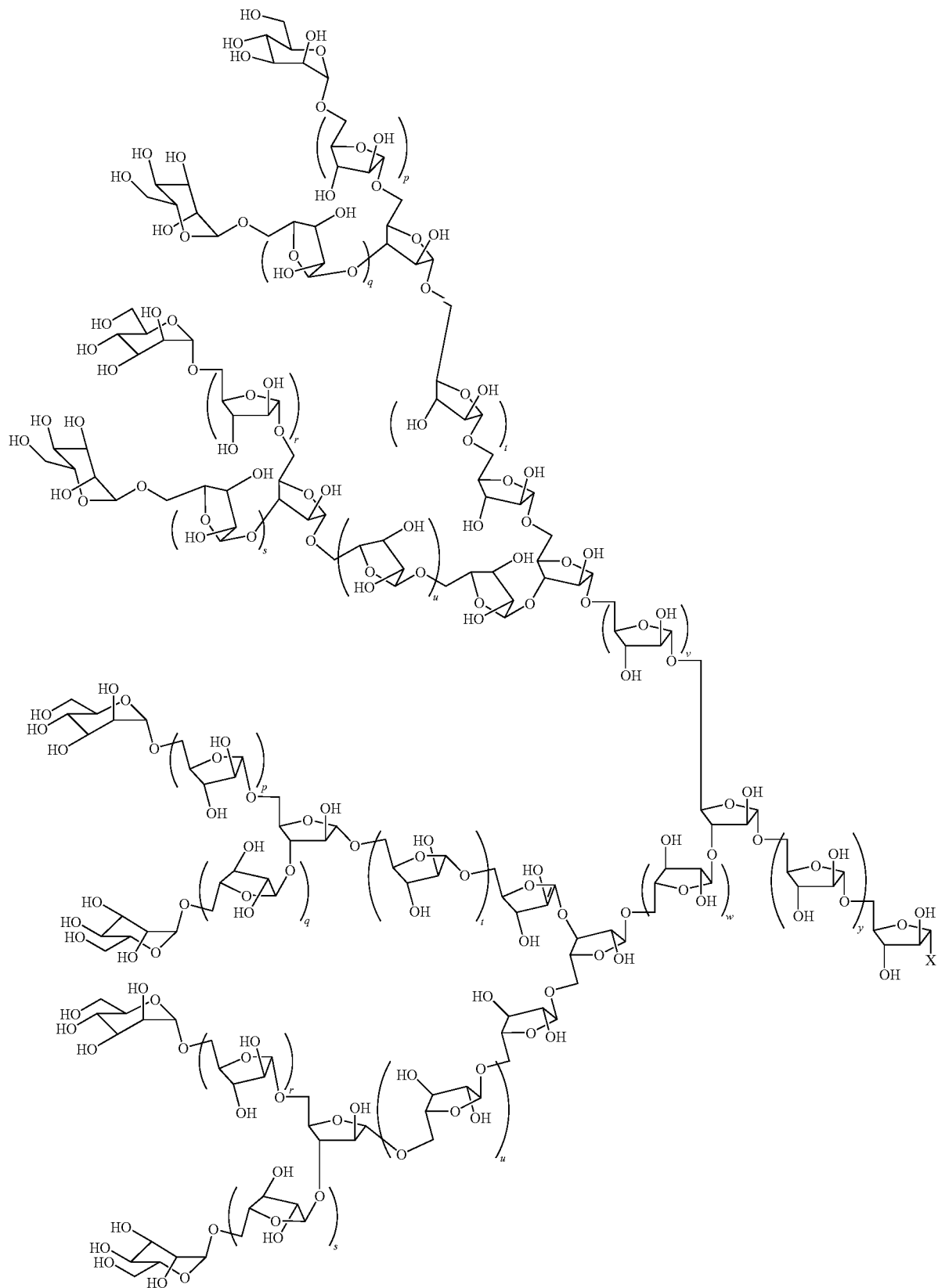

wherein each p, q, r, s, t, u, v, w and y are each independently an integer from 1 to 20; and X is an attachment group;

or a salt thereof.

A fifth aspect of the invention is a compound of formula V:

A sixth aspect of the invention is a compound of formula VI:

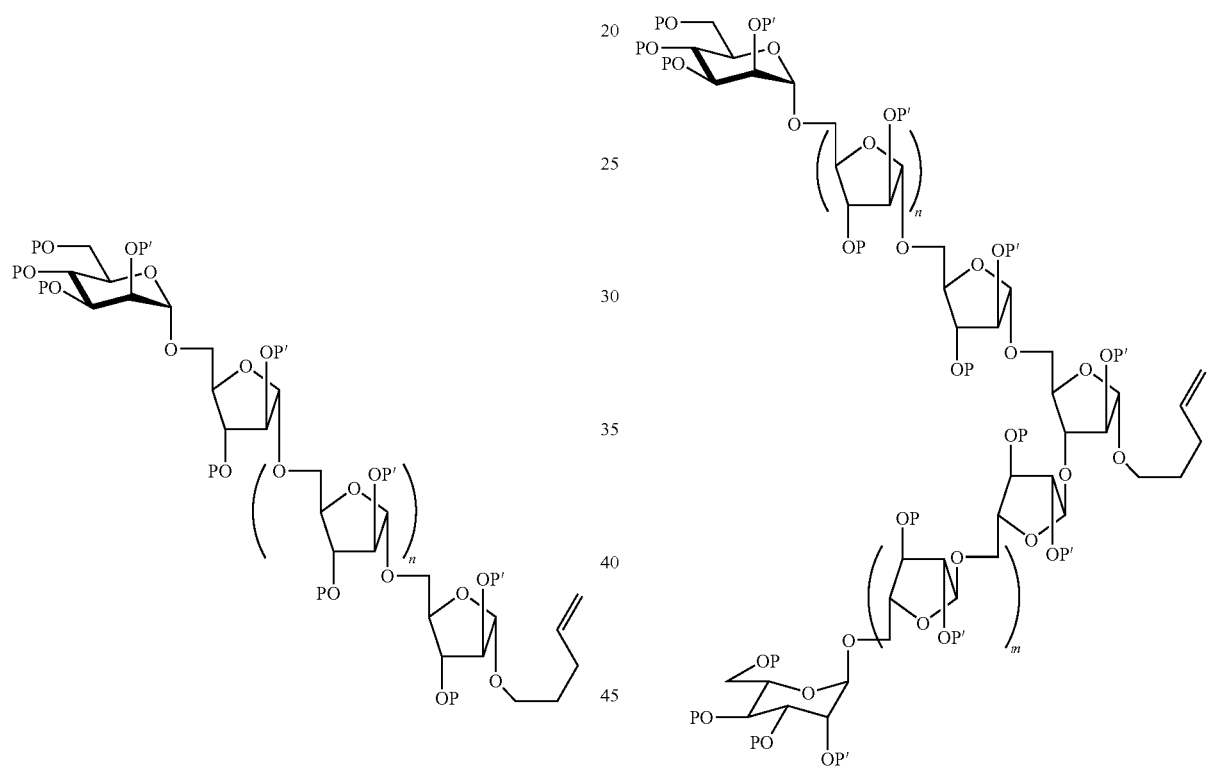

wherein P and P' are hydroxyl protecting groups and n is an integer from 1 to 20.

wherein P and P' are hydroxyl protecting groups and n and m are each independently an integer from 1 to 20.

A seventh aspect of the invention is a compound of formula VII:
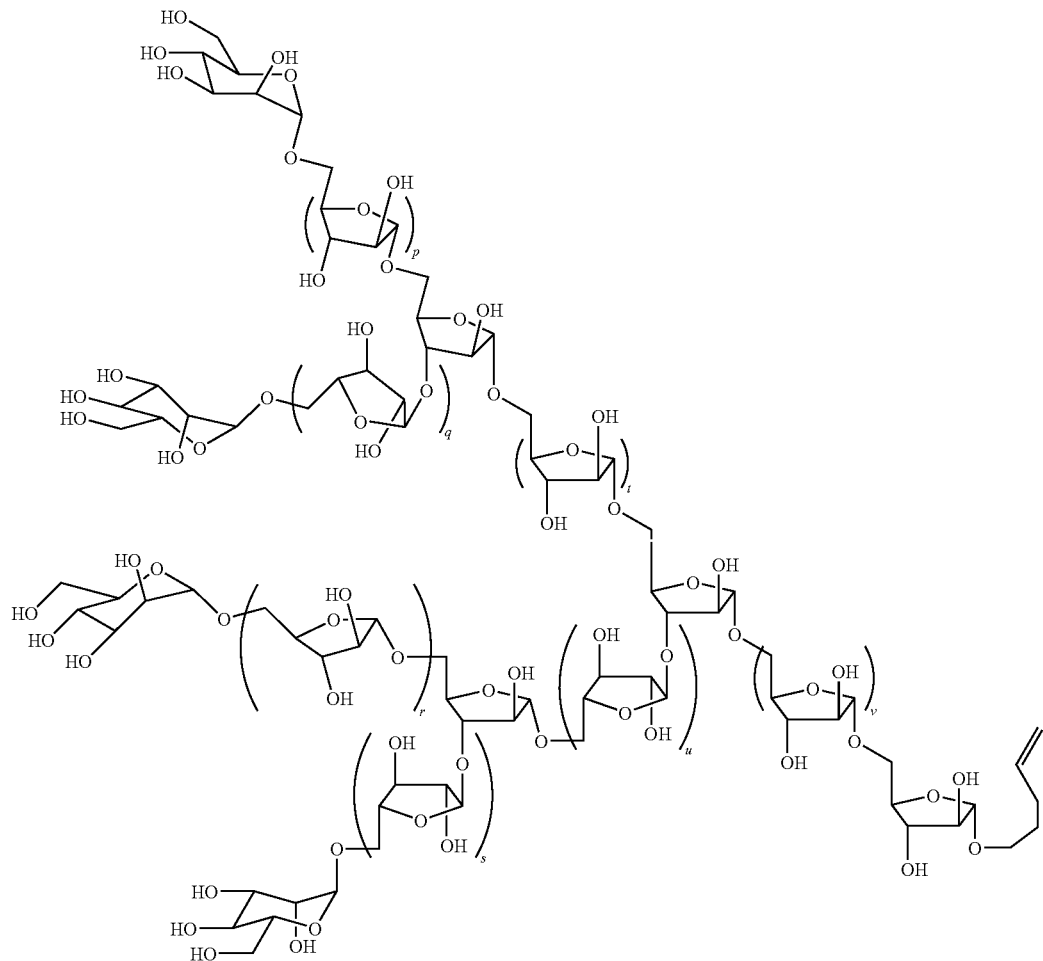
wherein p, q, r, s, t, u, and v are each independently an integer from 1 to 20.
An eighth aspect of the invention is a compound of formula VIII:
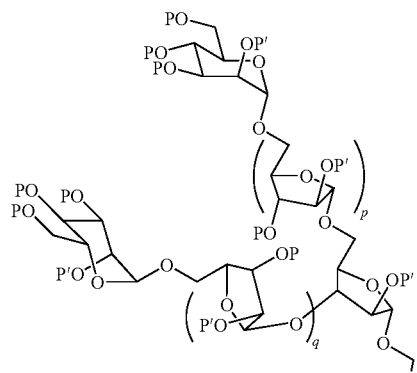

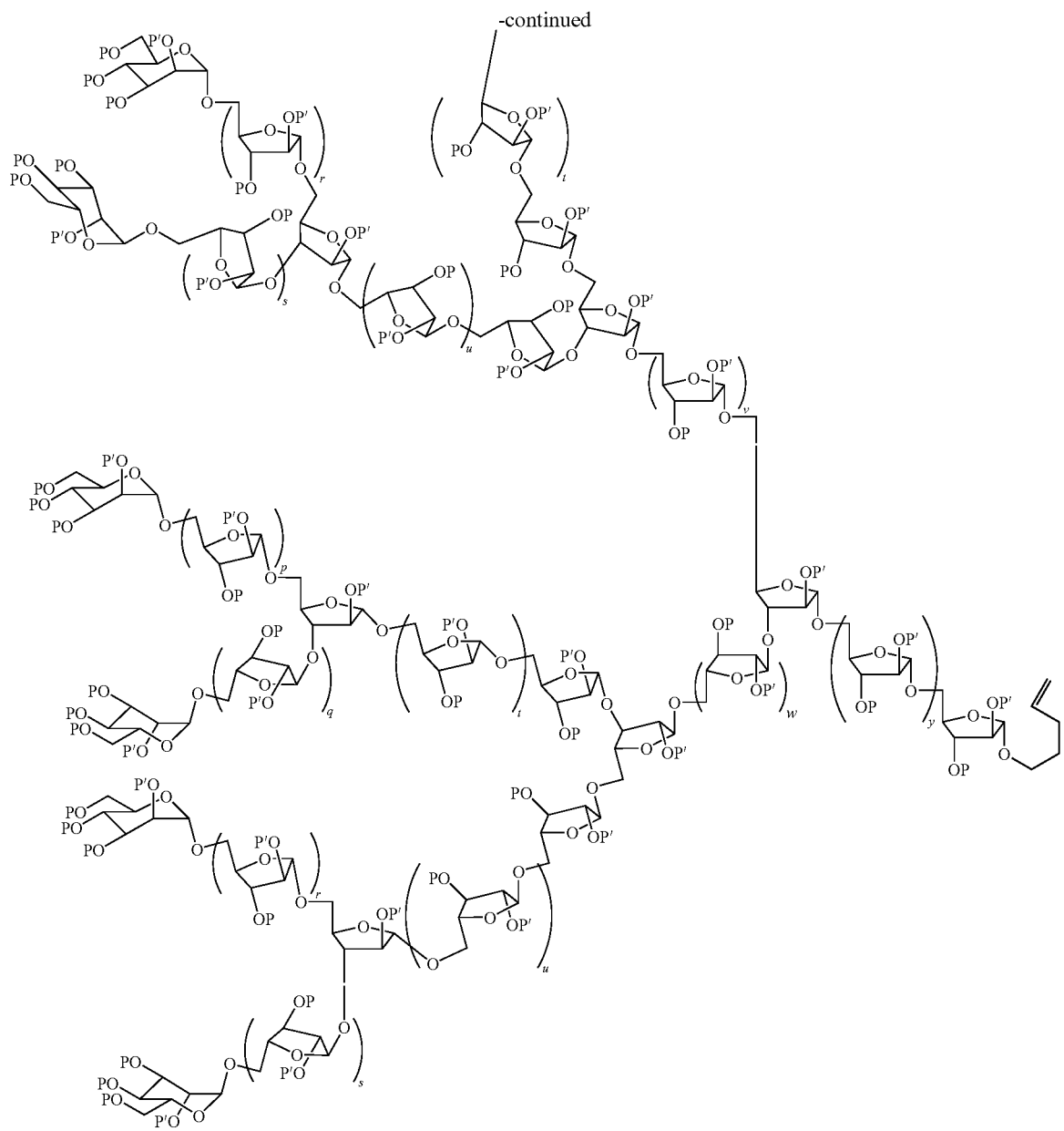
-continued wherein P and P' are hydroxyl protecting groups and each p, q, r, s, t, u, v, w and y are each independently an integer from 1 to 20.

Further aspects of the invention comprise methods of making the compounds of the invention. Accordingly, one aspect of the invention is a method of making a compound of formula V, precursor to the compound of formula I. A further aspect of the invention is a method of making a compound of formula VI, precursor to the compound of formula II. An additional aspect of the invention is a method of making a compound of formula VII, precursor to the compound of formula III. A still further aspect of the invention is a method of making a compound of formula VIII, precursor to the compound of formula IV.

DETAILED DESCRIPTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise. As used herein, the term "and/or" includes any and all combinations of one or more of the associated listed items.

All publications, patent applications, patents and other references cited herein are incorporated by reference in their entireties for the teachings relevant to the sentence and/or paragraph in which the reference is presented.

The cell surface of *Mycobacterium tuberculosis* is covered with a dense protective coat of organic compounds. Of these, the complex oligosaccharide known as lipoarabinomannan (LAM) is now recognized as the seat in the bacterium's ability to survive, renew itself and fend off external agents including therapeutic drugs. The drawing of LAM, shown in Scheme 1, displays the various domains.

Scheme 1 Lipoarabinomannan (LAM) of Mycobacterium tuberculosis

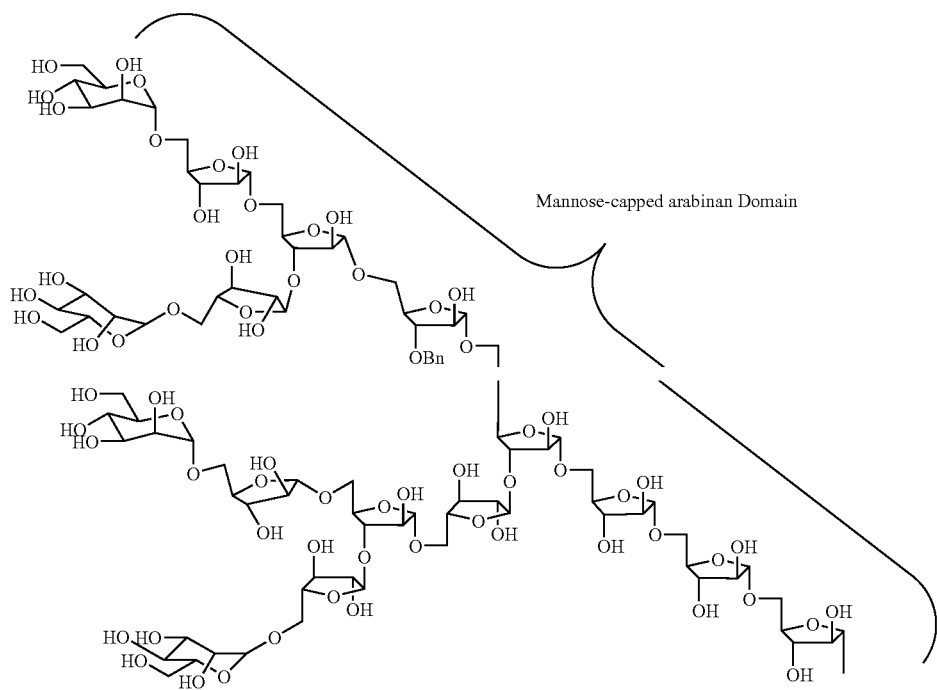

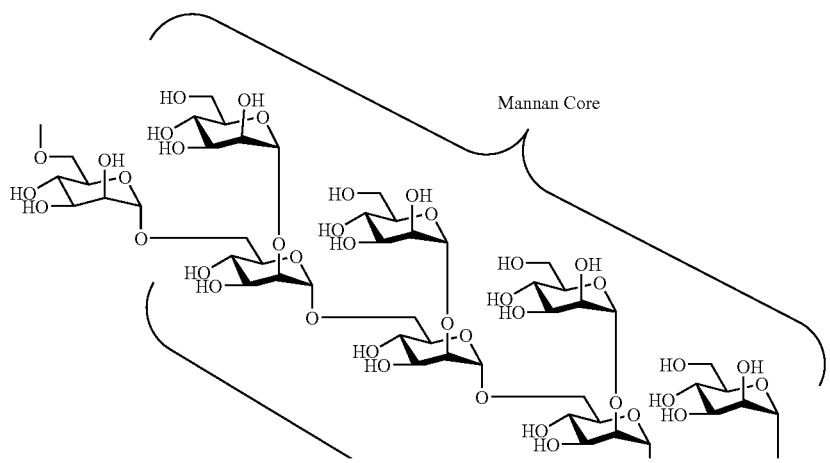

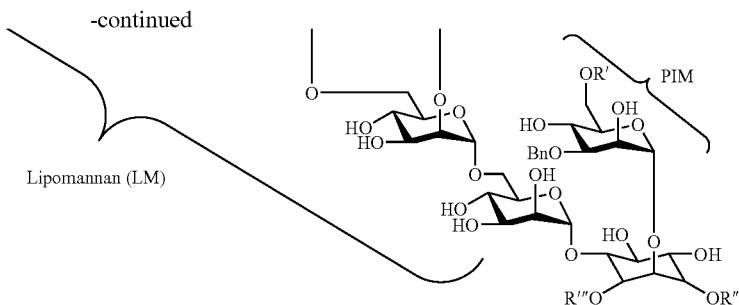

Lipomannan (LM)

wherein R' and R'' are fatty acyl groups and R''' is PO(OH) diacylglycerol.

The role of antibodies against tuberculosis had been discounted for many decades (Glatman-Freedman A and Casadevall A. *Clin. Microbiol. Rev.* 1998; 11:514-32). However, scientists at Albert Einstein College of Medicine have demonstrated that a monoclonal antibody to the mannose-capped arabinan domain was protective in a model of infection (Singh M and O'Hagan D. *Nature Biotechnology* 1999; 17:1075-81). In addition, arabinomannan conjugate vaccine candidates were found to be immunogenic and modified the course of infection to the benefit of the host (Glatman-Freedman et al., *J. Clin. Microbiol.* 2004; 42, 3225-3231; Hamasur et al., *Vaccine* 2003; 21:4081-93). These results are very encouraging considering that some of the most successful vaccines developed in recent years are polysaccharide vaccines, which work by eliciting protective immune responses.

Multivalent presentation is an important requirement for biologically active oligosaccharides (Kiessling et al. *Multivalency in Protein-Carbohydrate Recognition*. In: Fraser-Reid et al. eds. Berlin: Springer, 2001:1817-1861.) and so strategies for achieving multivalency are essential requirements of biologically important carbohydrate constructs. The representation in Scheme 1 shows that LAM is also a glycolipid, being composed of a carbohydrate (glyco), water-soluble (or hydrophilic) moiety, and fatty acid (lipid) residues that confer hydrophobic (or lipophilic) characteristics. Such glycolipids are known to be capable of supramolecular assembly, in which the hydrophilic "ends" cluster together. The result is a circular array, with the lipophilic "tails" all pointing inwards, and the hydrophilic "ends" on the circumference. The "mannose caps" which festoon the non-reducing end of the compound in scheme 1 (LAM) are major virulence factors, (Riviere et al. *J. Mol. Biol.* 2004; 344:907-18; Brennan, P. (2003) *Tuberculosis* 1:1) are engaged in intracellular signaling, and may be the earliest line of the host's defense against pulmonary infections.

The present invention describes novel compounds that comprise the subunits of LAM and procedures for the synthesis of these subunits, referred to as mannose-capped arabinan subunits. Compounds of formulas I-VIII are subunits of the complex glycans, or lipoarabinomannans, that are structural components of the *Mycobacteria* cell wall (Riviere et al. *J. Mol. Biol.* 2004; 344:907-18). The compounds of formulas I-VIII as described herein may be useful for eliciting an immune response, for enhancing an immune response, as a vaccine, as a vaccine adjuvant, to screen for compounds useful in the treatment of diseases caused by pathogenic *Mycobacterium* species and as a potential drug candidate itself for treatment of diseases including but not limited to, tuberculosis, leprosy, cancer, and asthma.

1. Definitions.

"Acyl" as used herein means a —C(O)R radical, where R is a suitable substituent such as alkyl, alkenyl, aryl, etc., which may be substituted or unsubstituted (for example, an acetyl group, a propionyl group, a butyroyl group, a benzoyl group, or an alkylbenzoyl group).

"Alkyl," as used herein, refers to a straight or branched chain hydrocarbon, preferably containing from 2 to 20 carbon atoms. Representative examples of alkyl include, but are not limited to, methyl, ethyl, isopropyl, phenyl, benzyl, n-propyl, iso-propyl, n-butyl, sec-butyl, iso-butyl, tert-butyl, n-pentyl, isopentyl, neopentyl, n-hexyl, 3-methylhexyl, n-heptyl, n-octyl, n-nonyl, n-decyl, and the like.

"Aryl" or "aromatic ring moiety" as used herein refers to an aromatic substituent which may be a single ring or multiple rings which are fused together, linked covalently or linked to a common group such as an ethylene or methylene moiety. The aromatic rings may each contain heteroatoms and hence "aryl" encompasses "heteroaryl" as used herein. An aryl can be a substituted or unsubstituted aryl unless otherwise indicated and hence the aryl moieties may be optionally substituted with halogen atoms, or other groups such as nitro, carboxyl, alkoxy, phenoxy and the like. Additionally, the aryl radicals may be attached to other moieties at any position on the aryl radical, which would otherwise be occupied by a hydrogen atom (such as, for example, 2-pyridyl, 3-pyridyl and 4-pyridyl).

"Alkyl aryl" as used herein means an alkyl as defined herein substituted with one or more aryl groups as defined herein.

"Aryl alkyl" as used herein means an aryl as defined herein substituted with one or more alkyl groups as defined herein.

"Attachment group" as used herein refers to a functional group, suitable for coupling a molecule to another molecule or to a substrate, and having a protected or unprotected reactive site or group on the group. Examples include but are not limited to COOH, NH$_2$, SH, biotin, diacylglyceryl, phosphatidyl diacyl glyceryl. carboxylic acid, alcohol, thiol, selenol or tellurol group, or a phosphono (e.g. dihydroxyphosphoryl), alkenyl (e.g., ethenyl) and alkynyl (e.g., ethynyl) group. Examples of surface attachment groups (with the reactive site or group in unprotected form) include but are not limited to: 4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl)phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl, 2-tellurylethyl, 3-tellurylpropyl, 2-(4-tellurylphenyl)ethynyl, 4-(2-(4-tellurylphenyl)ethynyl)phenyl, 4-tellurylmethylphenyl, 4-(2-tellurylethyl)phenyl, 4-(3-tellurylpropyl)phenyl, 4-(2-(4-tellurylmethylphenyl)ethynyl)phenyl; 4-(dihydroxyphosphoryl)phenyl, (dihydroxyphosphoryl)methyl, 2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl)methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto)phosphoryl)methyl]phenyl, 4-[2-(hydroxy(mercapto)phosphoryl)ethyl]phenyl, 4-[2-[4-(hydroxy(mercapto)phosphoryl)methylphenyl]ethynyl]phenyl; 4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl; 4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl; 4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl, 4-(4,4,5,5-tetramethyl-1,3,2-dioxaborolan-2-yl)phenyl; formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl; 4-(bromomethyl)phenyl, 2-bromoethyl; etc. See, e.g., U.S. Patent Application Publication No. 20050277770.

"Armed" as used herein refers to carbohydrate donors including, but not restricted to, n-pentenyl glycosides, equipped with O-alkyl, O-benzyl etc at C2.

"Disarmed" refers to carbohydrate donors including, but not restricted to, n-pentenyl glycosides, equipped with halide, O-acyl, azido, or other electron-withdrawing-groups of any type at C2.

"Hydroxyl protecting group" as used herein refers to any derivative of a hydroxyl group known in the an which can be used to mask the hydroxyl group during a chemical transformation and later removed under conditions resulting in the hydroxyl group being uncovered without other undesired effects on the remainder of the molecule containing the hydroxyl group. Many esters, acetals, ketals and silyl ethers are suitable protecting groups. Representative esters include acetyl, propionyl, pivaloyl and benzoyl esters. Representative ethers include allyl, benzyl, tetrahydropyranyl, ethoxyethyl, methoxymethyl, and benzyloxymethyl ethers. Representative acetals and ketals include acetonide, ketal groups derived from cyclic ketones such as cyclohexanone, from benzaldehyde or from p-O-methoxybenzaldehyde. Representative silyl ethers include trimethylsilyl, t-butyldimethylsilyl, and t-butyldiphenylsilyl ethers. See, e.g., U.S. Pat. Nos. 5,703,059, 7,015,200 and RE39,464.

*Mycobacterium* species of the invention include, but are not limited to, *Mycobacterium tuberculosis, M. avium, M intracellulare, M. kansasii, M. malmoense, M. simiae, M. szulgai, M. xenopi, M. scrofulaceum, M. abscessus, M. chelonae, M. haemophilum, M. vacae, M. aurum, M. ulcerans, M. fortuitum, M. marinum, M. immunogenum, M. neoaurum, M. bovis, M. africanum, M. austroafricanum, M. smegmatis, M. canariasense, M. komossense, M. murale, M. parascrofulaceum, M. bohemicum, M. hassiacum and M. mucogenicum, M. celatum, M. xenopi, M. palustre, M. terrae, M. conspicuum, M. genavense, M. doricum, M. heckeshornense, M. botniense, M. genavense, M. asiaticum, M. intermedium, M. kubicae, M. lentiflavum, M. palustre, M. intracellulare, M. tusciae, M. branderi, M. canettii, M. microti, M. heidelbergense, M. malmoense, M. lacus, M. shottsii, M. triplex, M. elephantis, M. hassiacum, M. novocastrense, M. alvei, M. septicum, M. peregrinum, M. novocastrense, M. brumae, M. fallax, M. triviale, M. confluentis, M. wolinskyi, M. goodii, M. smegmatis, M. holsaticum, M. mageritense, M. hodleri, M. mucogenicum, M. senegalense, M. frederiksbergense, M. chlorophenolicum, M. cookii, M. hiberniae, M. hodleri, M. madagascariense, M. flavescens, M. holsaticum, M. vanbaalenii, M. leprae, M. visibilis, M. avium* subsp. *paratuberculosis* (*M. paratuberculosis*), *M. avium* subsp. *silvaticum, M. avium* subsp. *hominissuis, M. bovis* subsp. *caprae*, and *M. interjectum*.

2. Compounds. Four of the compounds of this invention are represented by formulas I, II, III and IV in Scheme 2:

SCHEME 2

A Linear, monovalent mannose-capped arabinan

I

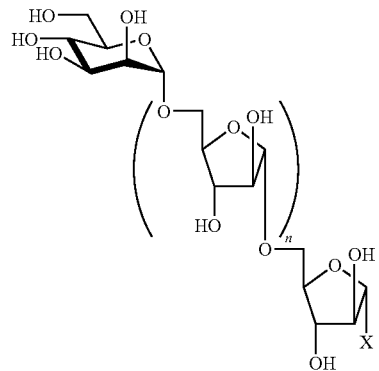

Branched, divalent mannose-capped arabinan

II

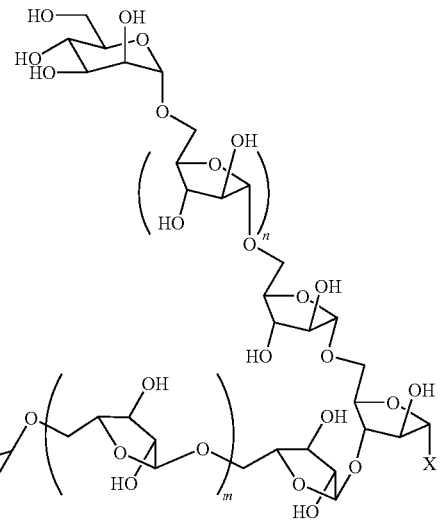

wherein:
n = 1, 2, 3 etc
o = 1, 2, 3 etc $$X = \begin{bmatrix} \text{a) } OCH_2(CH_2)_oCH_2SH \\ \text{b) } OCH_2(CH_2)_oCHCH_2OCOR' \\ \quad\quad\quad\quad\quad\quad | \\ \quad\quad\quad\quad\quad OCOR' \\ \text{c) } OCH_2(CH_2)_oCH_2NH_2 \\ \text{d) } OCH_2(CH_2)_oCOOH \\ \text{e) } OCH_2(CH_2)_oCH_2OPhospho\text{-}diacylglyceryl \\ \text{f) } OCH_2(CH_2)_oCH_2 NH_2\text{-Biotin} \end{bmatrix}$$

wherein:
n = 1, 2, 3 etc
m = 1, 2, 3 etc
o = 1, 2, 3 etc $$X = \begin{bmatrix} \text{a) } OCH_2(CH_2)_oCH_2SH \\ \text{b) } OCH_2(CH_2)_oCHCH_2OCOR' \\ \quad\quad\quad\quad\quad\quad | \\ \quad\quad\quad\quad\quad OCOR' \\ \text{c) } OCH_2(CH_2)_oCH_2NH_2 \\ \text{d) } OCH_2(CH_2)_oCOOH \\ \text{e) } OCH_2(CH_2)_oCH_2OPhospho\text{-}diacylglyceryl \\ \text{f) } OCH_2(CH_2)_oCH_2 NH_2\text{-Biotin} \end{bmatrix}$$

Branched Multivalent mannose-capped Arabinans

III

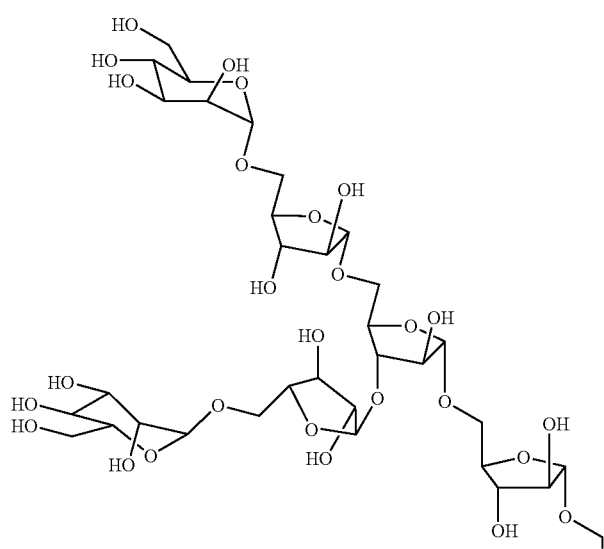

-continued
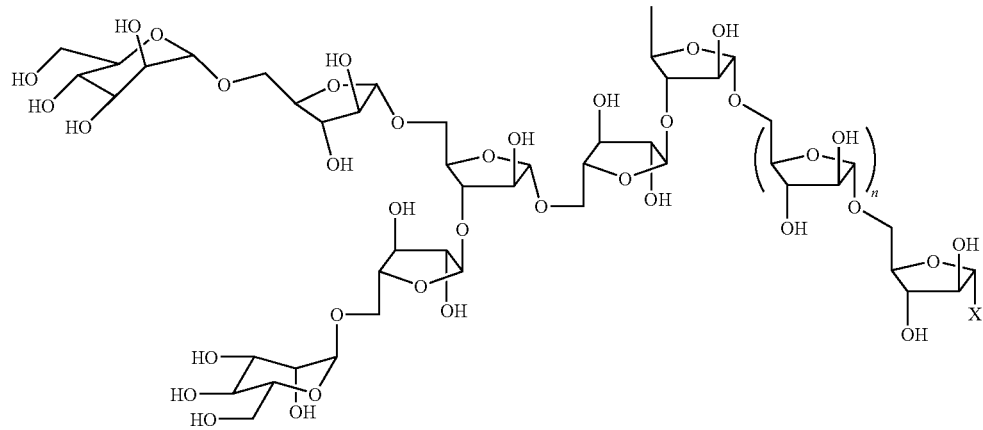
wherein:
n = 1, 2, 3 etc
o = 1, 2, 3 etc
$$X = \begin{bmatrix} a) \ OCH_2(CH_2)_oCH_2SH \\ b) \ OCH_2(CH_2)_oCHCH_2OCOR' \\ \quad\quad\quad\quad\quad | \\ \quad\quad\quad\quad\quad OCOR' \\ c) \ OCH_2(CH_2)_oCH_2NH_2 \\ d) \ OCH_2(CH_2)_oCOOH \\ e) \ OCH_2(CH_2)_oCH_2OPhospho\text{-}diacylglyceryl \\ f) \ OCH_2(CH_2)_oCH_2\ NH_2\text{-Biotin} \end{bmatrix}$$
Dendritic mannose-capped Arabinan Glycolipids
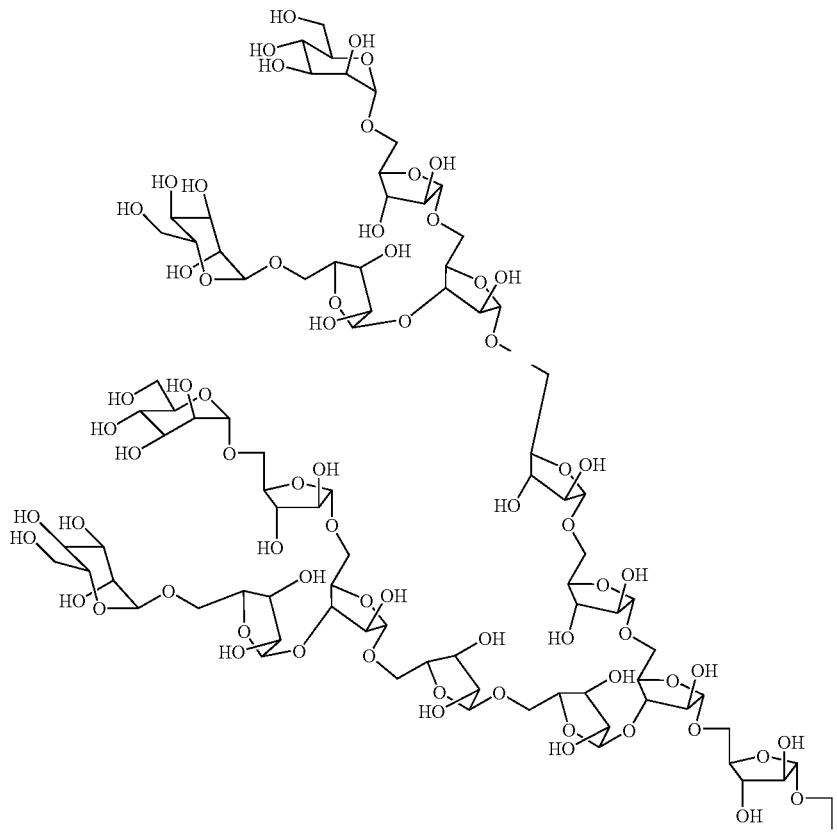
IV -continued

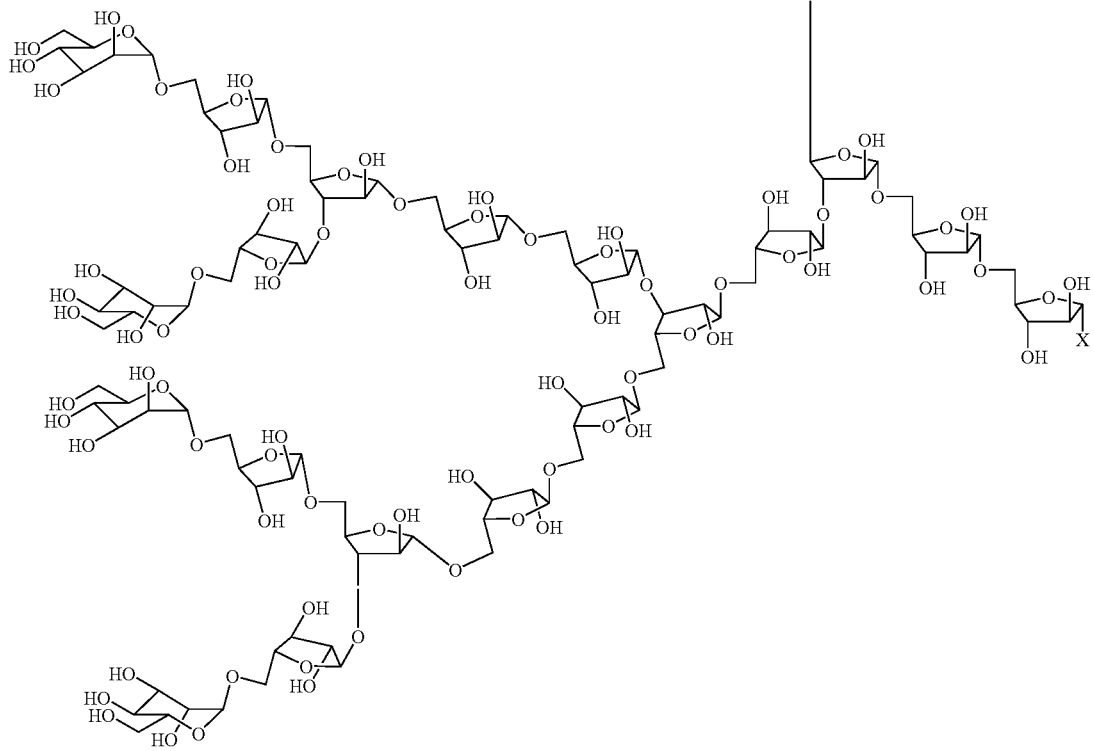

wherein:
n = 1, 2, 3 etc
o = 1, 2, 3 etc $$X = \begin{bmatrix} \text{a) } OCH_2(CH_2)_oCH_2SH \\ \text{b) } OCH_2(CH_2)_oCHCH_2OCOR' \\ \qquad\qquad\qquad\quad | \\ \qquad\qquad\qquad\ OCOR' \\ \text{c) } OCH_2(CH_2)_oCH_2NH_2 \\ \text{d) } OCH_2(CH_2)_oCOOH \\ \text{e) } OCH_2(CH_2)_oCH_2OPhospho\text{-} \\ \quad\text{diacylglyceryl} \\ \text{f) } OCH_2(CH_2)_oCH_2\ NH_2\text{-Biotin} \end{bmatrix}$$

In one embodiment, a compound of the invention is a compound of formula I:

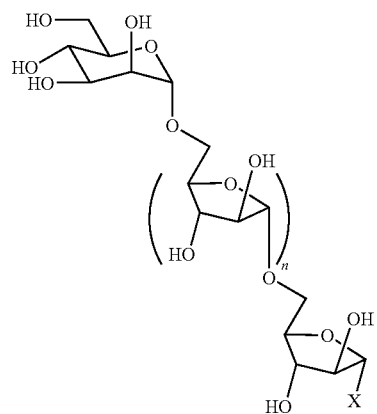

I wherein n is an integer from 1 to 20; and X is an attachment group; or a salt thereof.

The compound of formula I is a linear, monovalent arabinan bearing a mannose cap at the non-reducing end. The monovalent arabinans of formula I can be of any length. Thus, n is 1, 2, 3, or greater. In other embodiments of the invention n is 20 or less. Thus, n is 1, 2, 3, 4, 5, 6, 7, 8, 9, 10, 11, 12, 13, 14, 15, 16, 17, 18, 19, or 20. In additional embodiments of the present invention, n is an integer in a range from about 1-20, 1-15, 1-12, 1-10, 1-8, 1-5, 1-3 and the like.

At the reducing end of the compound of formula I, there is a glycosidically linked O-alkyl unit of any length terminating in an attachment group, X. X can be an attachment group of any type that allows bonding between the carbohydrate reducing end and another structure and includes, but is not limited to, COOH, $NH_2$, SH, biotin, diacylglyceryl, phosphatidyl diacyl glyceryl and other attachment or coupling groups. Thus, in some embodiments X includes, but is not limited to, a) $OCH_2(CH_2)_oCH_2SH$,
b) $OCH_2(CH_2)_oCHCH_2OCOR'$
   $\quad\quad\quad\quad\;\; |$
   $\quad\quad\quad\quad\; OCOR'$,
c) $OCH_2(CH_2)_oCOOH$,
d) $OCH_2(CH_2)_oCH_2NH_2$,
e) $OCH_2(CH_2)_oCH_2OPhosphodiacylglyceryl$, and
f) $OCH_2(CH_2)_oCH_2\ NH_2$-Biotin.

The alkyl unit of attachment groups a) through f) can be of any length. Thus, o is 1, 2, 3, or greater. In other embodiments of the invention o is 20 or less. Thus, o is 1, 2, 3, 4, 5, 6, 7, 8, 9, 10, 11, 12, 13, 14, 15, 16, 17, 18, 19, or 20. In further embodiments of the present invention, o is an integer in a range from about 1-20, 1-15, 1-12, 1-10, 1-8, 1-5, 1-3 and the like. R' is any carboxylic ester wherein the carboxylic ester comprises alkyl, aryl, alkyl aryl, or aryl alkyl groups that include, but are not limited to, methyl, ethyl, n-propyl, iso-propyl, n-butyl, phenyl, benzyl and combinations thereof.

A second aspect of the present invention is a compound of formula II,

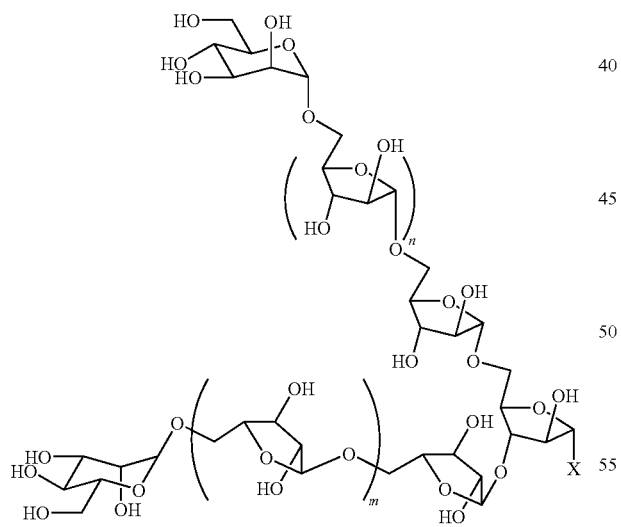

II wherein m and n are each independently an integer from 1 to 20; and X is an attachment group; or a salt thereof.

The compound of formula II is a divalent branched arabinan, capped at the non-reducing end with mannose units. The divalent branched arabinans of formula II can be of any length. Thus, n and m are 1, 2, 3, or greater. In other embodiments of the invention n is 20 or less. Thus, n is 1, 2, 3, 4, 5, 6, 7, 8, 9, 10, 11, 12, 13, 14, 15, 16, 17, 18, 19, or 20. In further embodiments of the present invention, n is an integer in a range from about 1-20, 1-15, 1-12, 1-10, 1-8, 1-5, 1-3 and the like. In still further embodiments, m is 1, 2, 3, 4, 5, 6, 7, 8, 9, 10, 11, 12, 13, 14, 15, 16, 17, 18, 19, or 20. In additional embodiments of the present invention, m is an integer in a range from about 1-20, 1-15, 1-12, 1-10, 1-8, 1-5, 1-3 and the like.

At the reducing end of the compound of formula II, there is a glycosidically linked O-alkyl unit of any length terminating in an attachment group, X. X can be an attachment group of any type that allows bonding between the carbohydrate reducing end and another structure and includes, but is not limited to, COOH, $NH_2$, SH, biotin, diacylglyceryl, and phosphatidyl diacyl glyceryl and other attachment or coupling groups. Thus, in some embodiments X includes, but is not limited to, a) $OCH_2(CH_2)_oCH_2SH$,
b) $OCH_2(CH_2)_oCHCH_2OCOR'$
   $\quad\quad\quad\quad\;\; |$
   $\quad\quad\quad\quad\; OCOR'$,
c) $OCH_2(CH_2)_oCOOH$,
d) $OCH_2(CH_2)_oCH_2NH_2$,
e) $OCH_2(CH_2)_oCH_2OPhosphodiacylglyceryl$, and
f) $OCH_2(CH_2)_oCH_2\ NH_2$-Biotin.

The alkyl unit of attachment groups a) through f) can be of any length. Thus, o is 1, 2, 3, or greater. In other embodiments of the invention o is 20 or less. Thus, o is 1, 2, 3, 4, 5, 6, 7, 8, 9, 10, 11, 12, 13, 14, 15, 16, 17, 18, 19, or 20. In further embodiments of the present invention, o is an integer in a range from about 1-20, 1-15, 1-12, 1-10, 1-8, 1-5, 1-3 and the like. R' is any carboxylic ester wherein the carboxylic ester comprises alkyl, aryl, alkyl aryl, or aryl alkyl groups that include, but are not limited to, methyl, ethyl, n-propyl, iso-propyl, n-butyl, phenyl, benzyl and combinations thereof.

A further embodiment of the present invention is a compound of formula III,

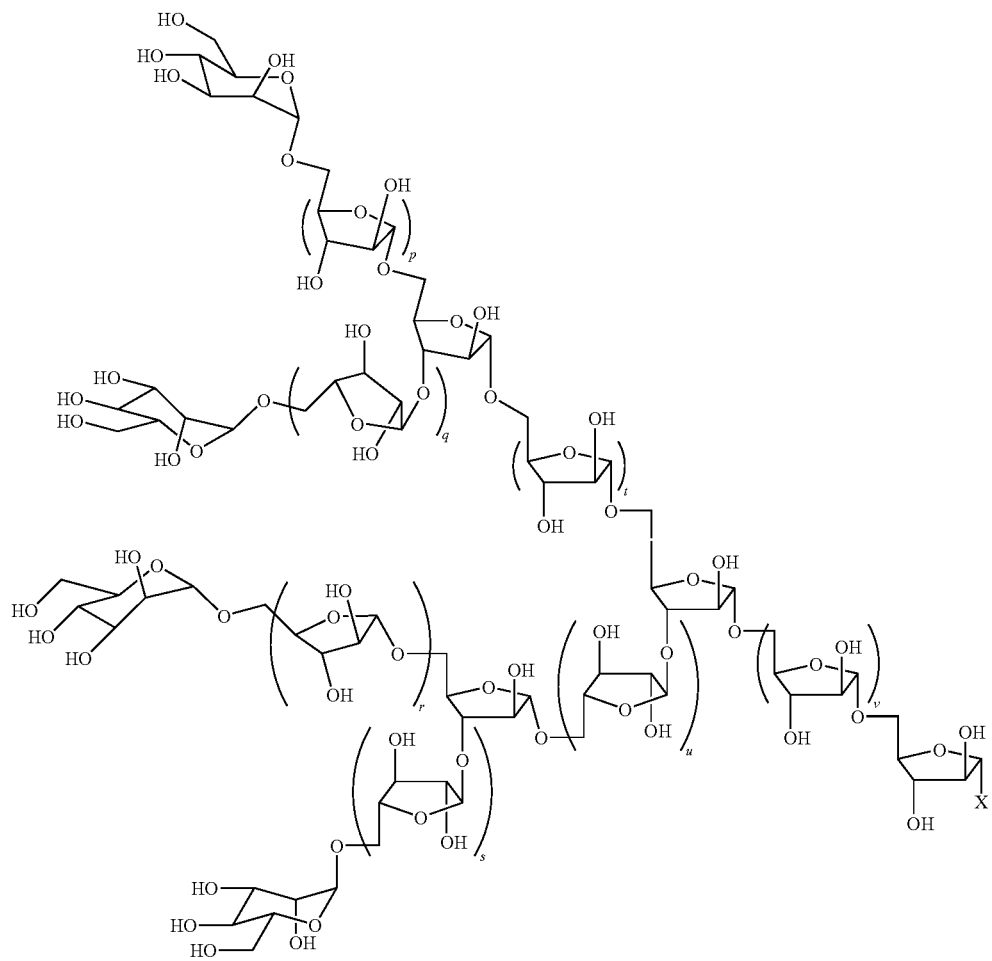

III wherein p, q, r, s, t, u, and v are each independently an integer from 1 to 20; and X is an attachment group; or a salt thereof.

The compound of formula III is a divalent branched arabinan, capped at the non-reducing end with mannose units. The divalent branched arabinans of formula III can be of any length. Thus, p, q, r, s, t, u, and v are each independently 1, 2, 3, or greater. In other embodiments of the invention p, q, r, s, t, u, and v are each independently 20 or less. Thus, p, q, r, s, t, u, and v are each independently 1, 2, 3, 4, 5, 6, 7, 8, 9, 10, 11, 12, 13, 14, 15, 16, 17, 18, 19, or 20. In further embodiments of the present invention, p, q, r, s, t, u, and v are each independently an integer in a range from about 1-20, 1-15, 1-12, 1-10, 1-8, 1-5, 1-3 and the like.

At the reducing end of the compound of formula III, there is a glycosidically linked O-alkyl unit of any length terminating in an attachment group, X. X can be an attachment group of any type that allows bonding between the carbohydrate reducing end and another structure and includes, but is not limited to, COOH, $NH_2$, SH, biotin, diacylglyceryl, phosphatidyl diacyl glyceryl and other attachment or coupling groups. Thus, in some embodiments X includes, but is not limited to, a) $OCH_2(CH_2)_oCH_2SH$,
b) $OCH_2(CH_2)_oCHCH_2OCOR'$
   |
   $OCOR'$,
c) $OCH_2(CH_2)_oCOOH$,
d) $OCH_2(CH_2)_oCH_2NH_2$,
e) $OCH_2(CH_2)_oCH_2OPhosphodiacylglyceryl$, and
f) $OCH_2(CH_2)_oCH_2 NH_2$-Biotin.

The alkyl unit of attachment groups a) through f) can be of any length. Thus, o is 1, 2, 3, or greater. In other embodiments of the invention o is 20 or less. Thus, o is 1, 2, 3, 4, 5, 6, 7, 8, 9, 10, 11, 12, 13, 14, 15, 16, 17, 18, 19, 20, and combinations thereof. In further embodiments of the present invention, o is an integer in a range from about 1-20, 1-15, 1-12, 1-10, 1-8, 1-5, 1-3 and the like. R' is any carboxylic ester wherein the carboxylic ester comprises alkyl, aryl, alkyl aryl, or aryl alkyl groups that include, but are not limited to, methyl, ethyl, n-propyl, isopropyl, n-butyl, phenyl, benzyl and combinations thereof.

Additional embodiments of the present invention include a compound of formula IV:
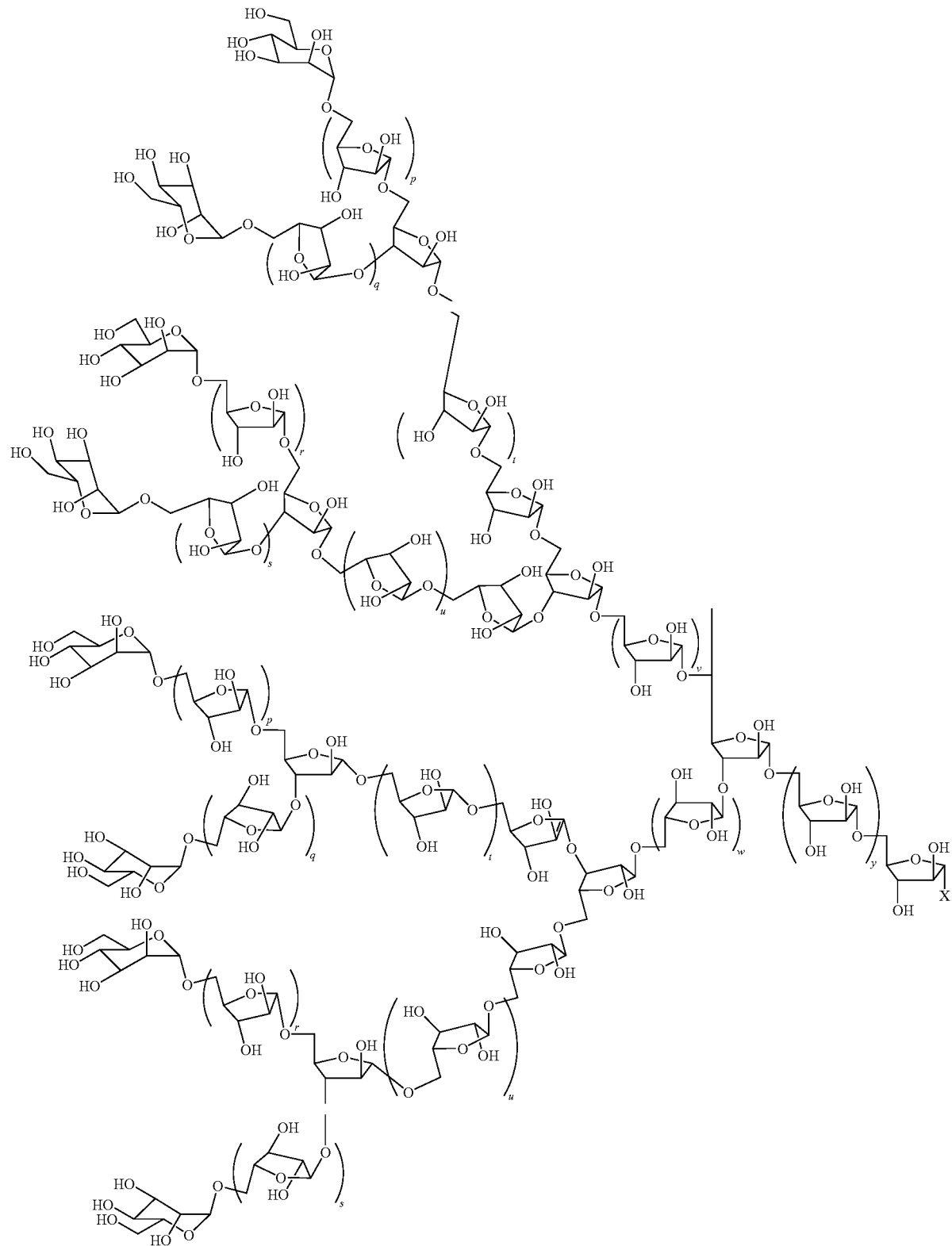

wherein each p, q, r, s, t, u, v, w and y is each independently an integer from 1 to 20; and X is an attachment group;

or a salt thereof.

The compound of formula IV is a dendritic branched arabinan, capped at the non-reducing end with mannose units. The branched arabinan can be of any length. Thus, each p, q, r, s, t, u, v, w and y is each independently 1, 2, 3, or greater. In other embodiments of the invention, each p, q, r, s, t, u, v, w and y is each independently 20 or less. Accordingly, each p, q, r, s, t, u, v and y is each independently 1, 2, 3, 4, 5, 6, 7, 8, 9, 10, 11, 12, 13, 14, 15, 16, 17, 18, 19, or 20. In further embodiments of the present invention, each p, q, r, s, t, u, V, w and y is each independently an integer in a range from about 1-20, 1-15, 1-12, 1-10, 1-8, 1-5, 1-3 and the like.

At the reducing end of the compound of formula IV, there is a glycosidically linked O-alkyl unit of any length terminating in an attachment group, X. X can be an attachment group of any type that allows bonding between the carbohydrate reducing end and another structure and includes, but is not limited to, COOH, $NH_2$, SH, biotin, diacylglyceryl, phosphatidyl diacyl glyceryl and other attachment or coupling groups. Thus, in some embodiments X includes, but is not limited to, a) $OCH_2(CH_2)_oCH_2SH$,
b) $OCH_2(CH_2)_oCHCH_2OCOR'$
      |
      $OCOR'$,
c) $OCH_2(CH_2)_oCOOH$,
d) $OCH_2(CH_2)_oCH_2NH_2$,
e) $OCH_2(CH_2)_oCH_2OPhosphodiacylglyceryl$, and
f) $OCH_2(CH_2)_oCH_2 NH_2$-Biotin.

The alkyl unit of attachment groups a) through f) can be of any length. Thus, o is 1, 2, 3, or greater. In other embodiments of the invention o is 20 or less. Thus, o is 1, 2, 3, 4, 5, 6, 7, 8, 9, 10, 11, 12, 13, 14, 15, 16, 17, 18, 19, or 20. In further embodiments of the present invention, o is an integer in a range from about 1-20, 1-15, 1-12, 1-10, 1-8, 1-5, 1-3 and the like. R' is any carboxylic ester wherein the carboxylic ester comprises alkyl, aryl, alkyl aryl, or aryl alkyl groups that include, but are not limited to, methyl, ethyl, n-propyl, isopropyl, n-butyl, phenyl, benzyl and combinations thereof.

A further aspect of the present invention includes a compound of formula V:

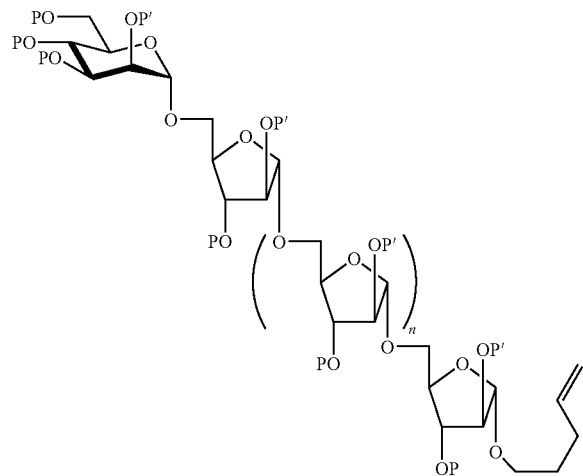

wherein P and P' are hydroxyl protecting groups and n is an integer from 1 to 20.

The compound of formula V is a monovalent arabinan and a precursor to the compound of formula I. Similar to the compound of formula I, the compound of formula V can be of any length. Thus, n is 1, 2, 3, or greater. In other embodiments, n is 20 or less. Accordingly, n is 1, 2, 3, 4, 5, 6, 7, 8, 9, 10, 11, 12, 13, 14, 15, 16, 17, 18, 19, or 20. In further embodiments of the present invention, n is an integer in a range from about 1-20, 1-15, 1-12, 1-10, 1-8, 1-5, 1-3 and the like. P and P' are any hydroxyl protecting group. In some embodiments of the invention, P is Bn and P' is Bz.

An additional aspect of the invention is a compound of formula VI:

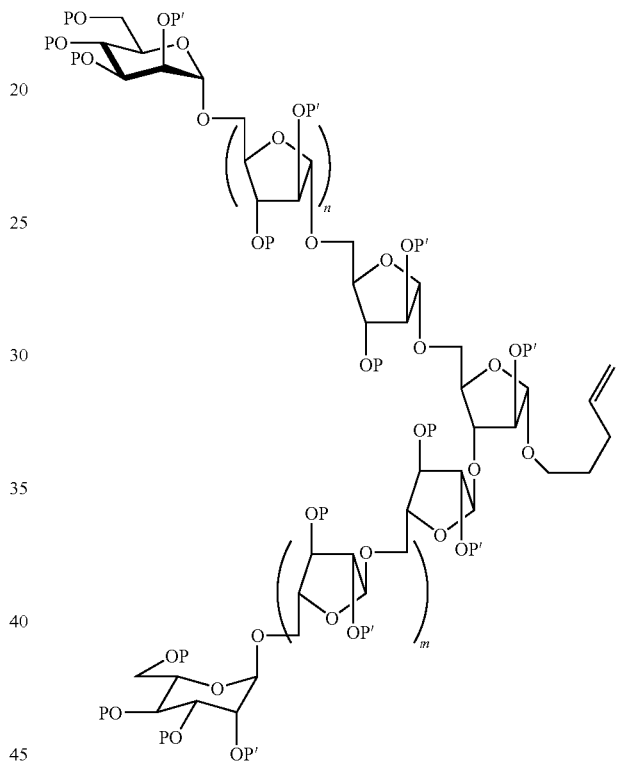

wherein P and P' are hydroxyl protecting groups and m and n are each independently an integer from 1 to 20.

The compound of formula VI is a divalent arabinan and a precursor to the compound of formula II. The compound of formula VI can be of any length. Thus, n and m are 1, 2, 3, or greater. In other embodiments of the invention n and/or m are 20 or less. Thus, n is 1, 2, 3, 4, 5, 6, 7, 8, 9, 10, 11, 12, 13, 14, 15, 16, 17, 18, 19, or 20. In further embodiments of the present invention, n is an integer in a range from about 1-20, 1-15, 1-12, 1-10, 1-8, 1-5, 1-3 and the like. In some other embodiments, m is 1, 2, 3, 4, 5, 6, 7, 8, 9, 10, 11, 12, 13, 14, 15, 16, 17, 18, 19, or 20. In still other embodiments of the present invention, m is an integer in a range from about 1-20, 1-15, 1-12, 1-10, 1-8, 1-5, 1-3 and the like. P and P' are any hydroxyl protecting group. In some embodiments of the invention, P is Bn and P' is Bz.

A further embodiment of the invention is a compound of formula VII:

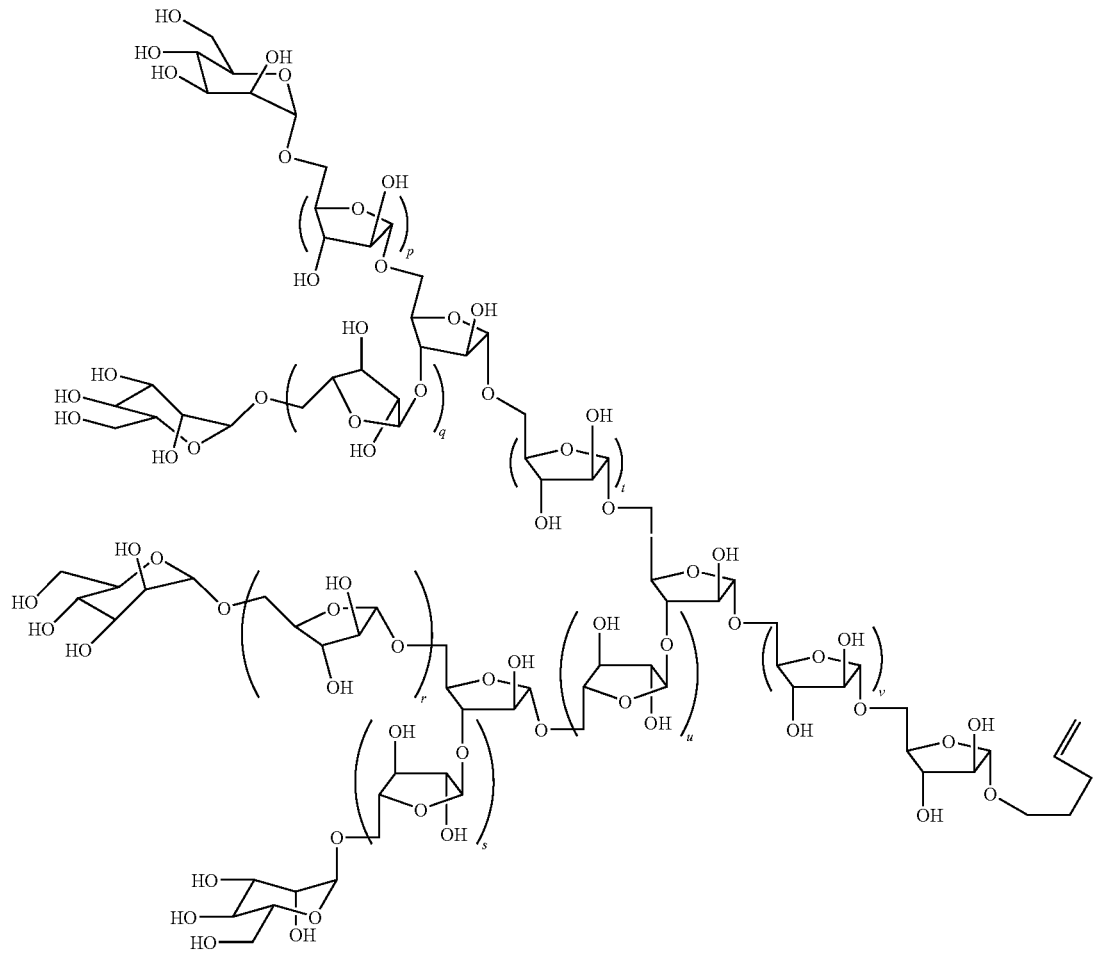

wherein p, q, r, s, t, u, and v are each independently an integer from 1 to 20.

The compound of formula VII is a multivalent branched arabinan and a precursor to the compound of formula III. The compound of formula VII can be of any length. Thus, p, q, r, s, t, u, and v are each independently 1, 2, 3, or greater. In other embodiments of the invention p, q, r, s, t, u, and v are each independently 20 or less. Accordingly, p, q, r, s, t, u, and v are each independently 1, 2, 3, 4, 5, 6, 7, 8, 9, 10, 11, 12, 13, 14, 15, 16, 17, 18, 19, or 20. In further embodiments of the present invention, p, q, r, s, t, u, and v are each independently an integer in a range from about 1-20, 1-15, 1-12, 1-10, 1-8, 1-5, 1-3 and the like.

A further aspect of the invention is a compound of formula VIII:
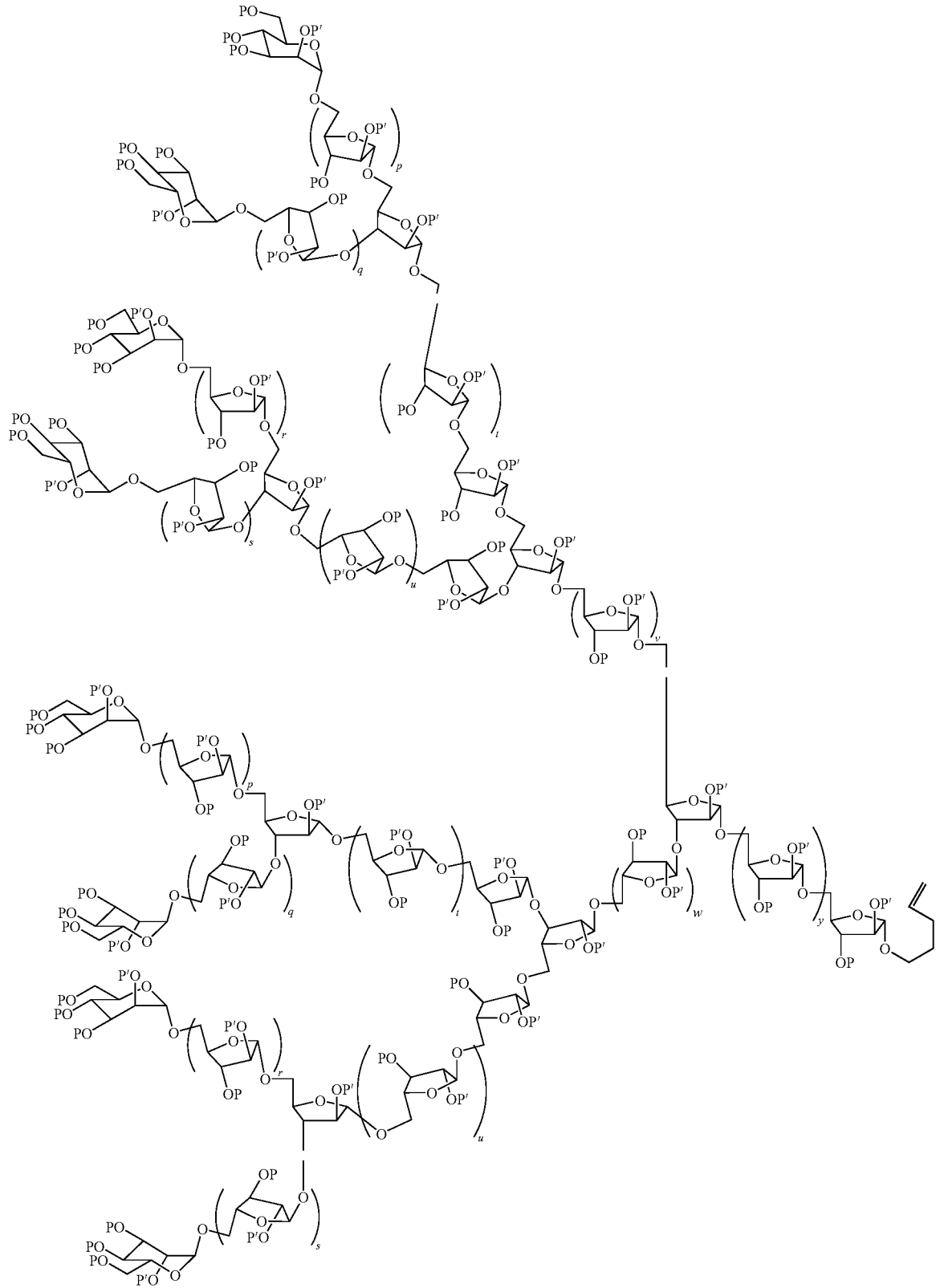

wherein P and P' are hydroxyl protecting groups and each p, q, r, s, t, U, v, W and y is each independently an integer from 1 to 20.

The compound of formula VIII is a dendritic branched arabinan and a precursor to the compound of formula IV. Similar to the compound of formula IV, the branched arabinan of formula VIII can be of any length. Thus, each p, q, r, 5, t, U, v, W and y is each independently 1, 2, 3, or greater. In other embodiments of the invention each p, q, r, s, t, u, v and y is each independently 20 or less. Accordingly, each p, q, r, s, t, u, v, w and y is each independently 1,2,3,4, 5, 6, 7, 8, 9, 10, 11, 12, 13, 14, 15, 16, 17, 18, 19, or 20. In further embodiments of the present invention, each p, q, r, s, t, u, v, w and y is each independently an integer in a range from about 1-20, 1-15, 1-12, 1-10, 1-8, 1-5, 1-3 and the like. P and P' are any hydroxyl protecting group. In some embodiments of the invention, P is Bn and P' is Bz.

Methods of Making. The present invention describes procedures for synthesis of the arabinan and mannose-capped arabinan domains of the LAM (Scheme 1). The main problem facing the arabinan domain of LAM comes from difficulty working with furanose sugar derivatives. These are known to be much more labile than their pyranose counterparts. Thus, there are not many methods of making, and of using furanosides. The present invention overcomes these problems by using a simplified approach involving n-pentenyl furanosyl orthoesters of arabinose.

The mannose-capped arabinans of formulas I, II, III and IV are subunits or synthetic constructs of lipoarabinomannan which are known to be immunogenic and are able to modify the course of infection to the benefit of the host (Glatman-Freedman et al. *J. Clin. Microbiol.* 2004; 42, 3225-3231; Hamasur B, Haile M, Pawlowski A et al. *Vaccine* 2003; 21:4081-93; Riviere et al. *J. Mol. Biol.* 2004; 344:907-18). Further, the compounds of formulas V, VI, VII and VIII are precursors in the synthesis of the compounds of formulas I, II, III and IV, respectively.

Some of the materials used in the synthesis of compounds of formulas I-VIII are prepared as shown in Scheme 3.

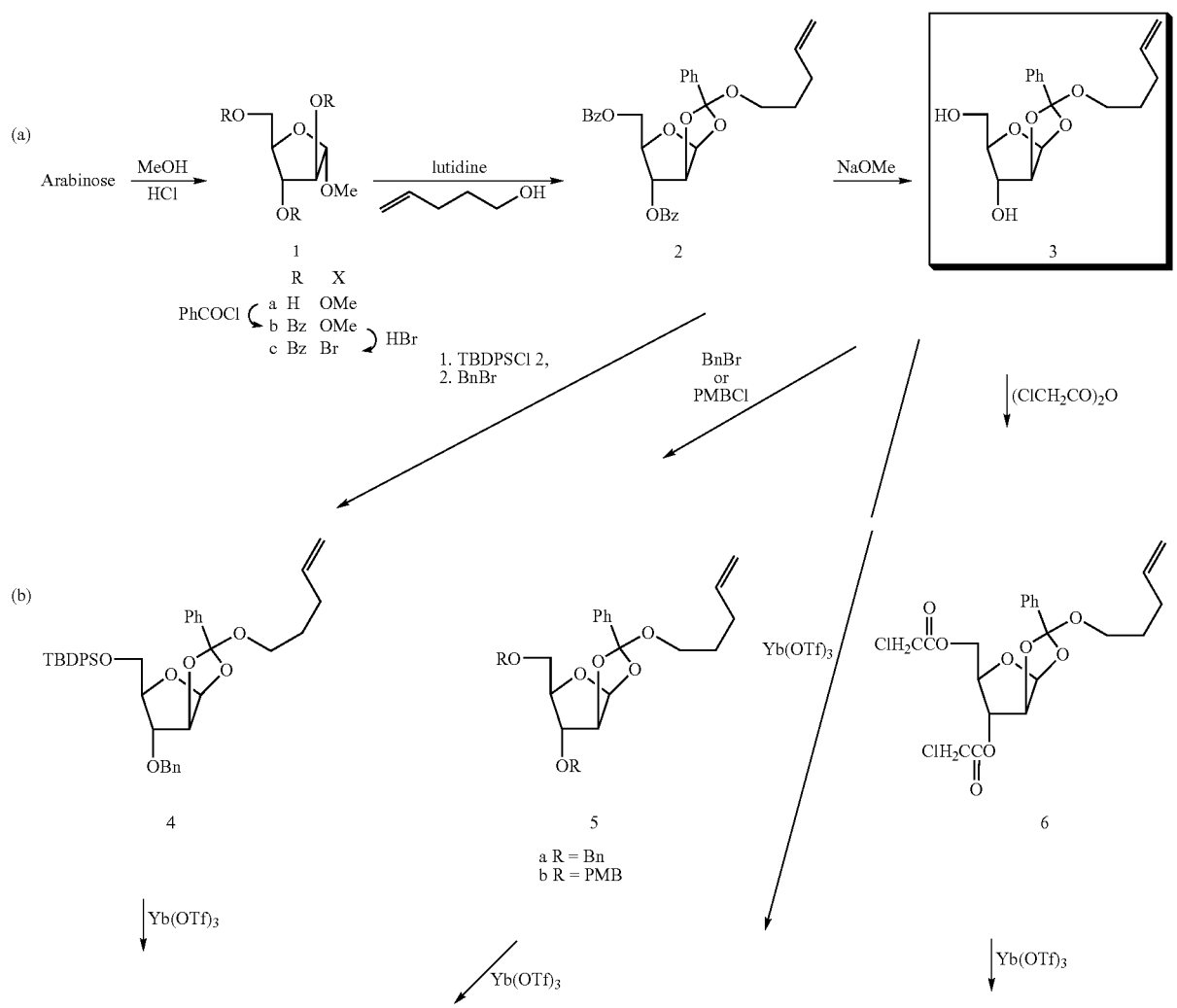

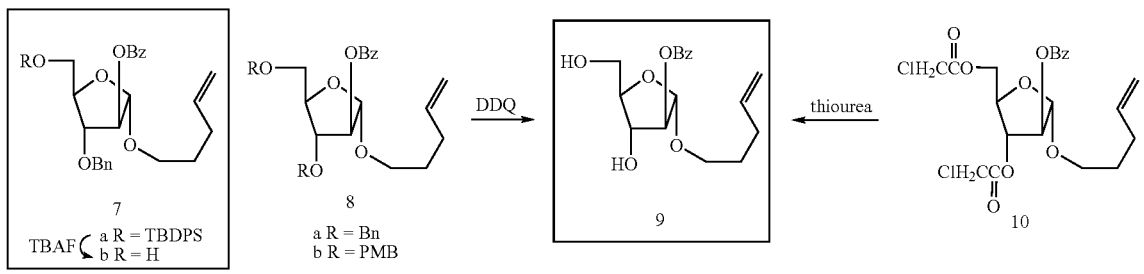

Methyl arabinofuranoside, 1a, is available commercially; but can also be prepared by treating arabinose with methanolic hydrogen chloride as indicated in Scheme 3a, according to a published procedure (Ness R K, and Fletcher, H G, Jr. *J. Amer. Chem. Soc.* 1958, 80: 2007-2010). Exhaustive treatment with benzoyl chloride followed by treatment with HBr afforded the glycosyl bromide 1c. Standard treatment with lutidine in the presence of pent-4-enol (n-pentenyl alcohol) gave orthoester 2. Alternatively, the orthoester 2 can also be provided by treatment of the glycosyl bromide 1c with collidine or any hindered pyridine also in the presence of pent-4-enol. The orthoester diol, 3 was obtained from the orthoester 2 by saponification. The variously protected analogs, 4, 5 and 6, in Scheme 3b were then obtained by routine use of the indicated reagents.

Rearrangement of 4, 5 or 6 to the corresponding n-pentenyl furanosides 7, 8 or 10, respectively, occurred upon treatment of the orthoesters with Ytterbium (III) triflate ($Yb(OTf)_3$) (Jayaprakash, K N and Fraser-Reid, B., *Synlett,* 2004 301-305). Of special interest for the work ahead, are the structures with one and two free-OHs, 7b and 9, respectively. A number of different routes to achieve compound 9 are presented in the embodiment of the invention set forth in Scheme 3. In some embodiments of the invention, the direct rearrangement of 3→9 is used.

Compounds of Formula I

Precursors to compounds of formula I may be obtained from precursor 15 (Formula V). In one embodiment of the present invention, precursor 15 can be prepared as shown in Scheme 4.

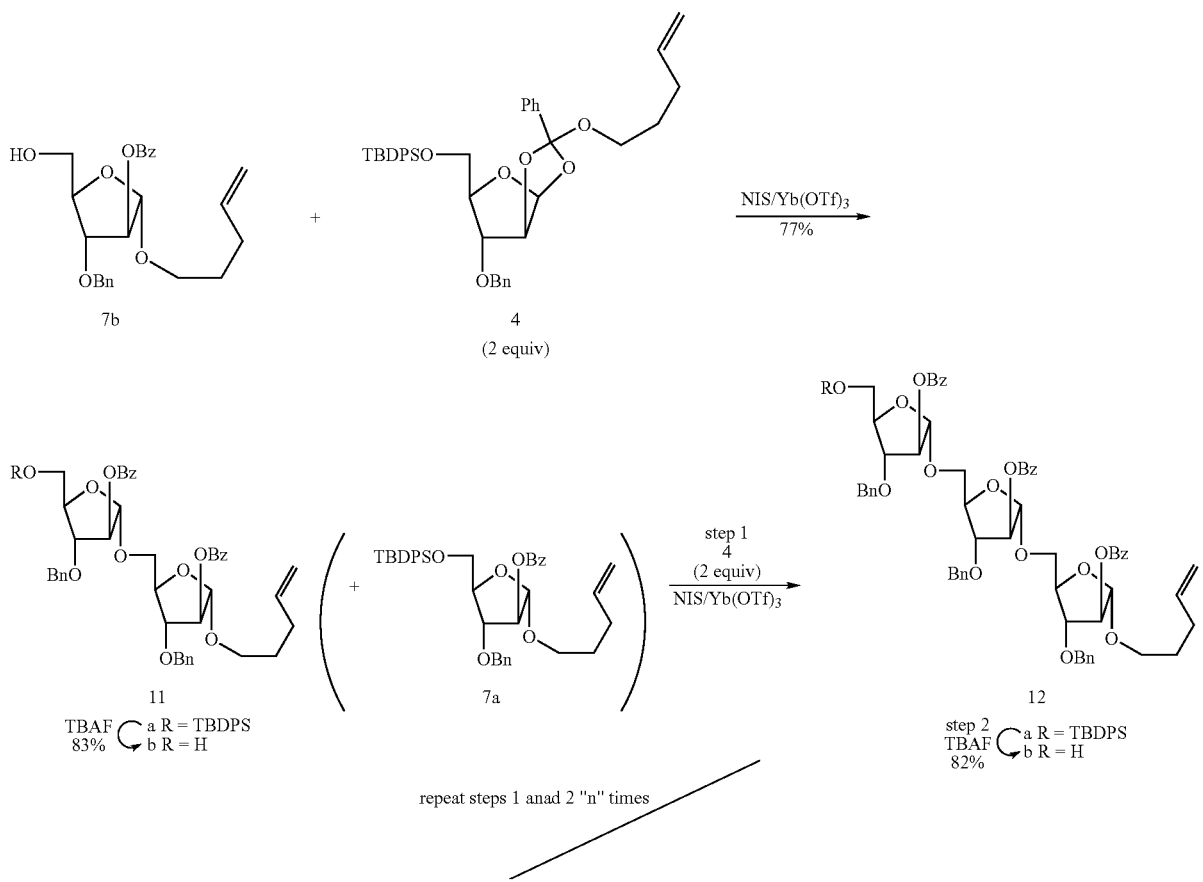

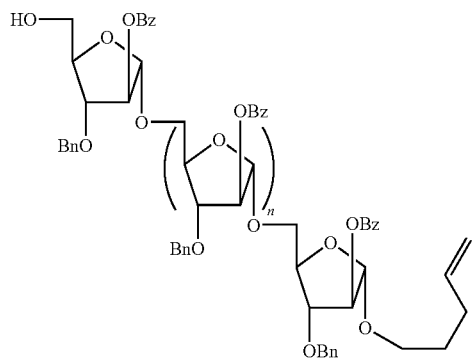

13

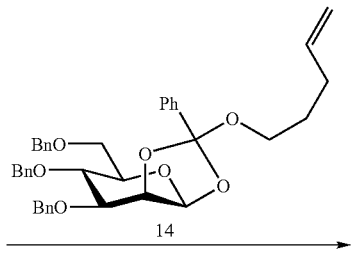

14

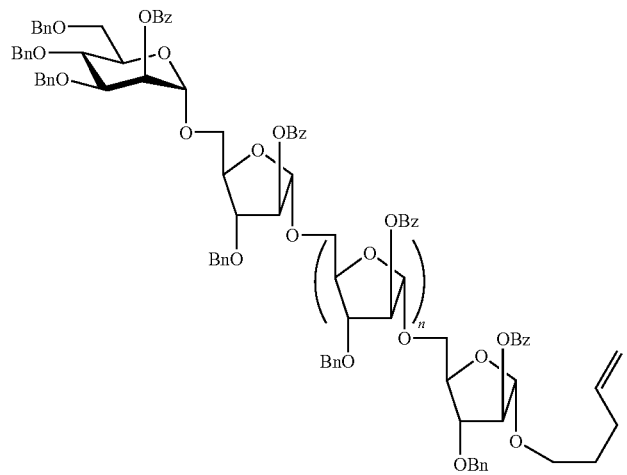

15 (Precursor to I)

In the embodiment shown in Scheme 4, the n-pentenyl glycoside (NPG) acceptor 7b was treated with 2 equivalents of n-penteny orthoester (NPOE) 4 under catalysis by Ytterbium (III) triflate in the presence of N-iodosuccinimide ((Yb(OTf)$_3$/NIS). In other embodiments, catalysis by Ytterbium (III) triflate is carried out in the presence of N-bromosuccinimide (NBS), bromine, a divalent mercury salt, or any like oxidizing agent. Diarabinan 11a was produced in 77% yield, and readily separated from NPG 7a (which had come from the excess NPOE 4). Iterating the last two steps, in which the yields were upheld, gave trisaccharide 12b. Finally, the free-OH group of 13 can be capped with the mannosyl orthoester 14 to afford the desired precursor formula V (15) required for compounds of formula I.

As described previously, the compounds of formula V (precursor to formula I) can be of any length. Thus, in some embodiments, further iterations can be carried out as needed to obtain 13, with n being any number required. Thus, n is 1, 2, 3, or greater. In other embodiments n is 20 or less. Accordingly, n is 1, 2, 3, 4, 5, 6, 7, 8, 9, 10, 11, 12, 13, 14, 15, 16, 17, 18, 19, or 20. In additional embodiments of the present invention, n is an integer in a range from about 1-20, 1-15, 1-12, 1-10, 1-8, 1-5, 1-3 and the like.

In the embodiment presented in Scheme 4, the hydroxyl protecting groups are presented as benzyl and benzoate protecting groups. In other embodiments, the protecting groups can be any other hydroxyl protecting groups that can be removed selectively from one another and are stable to the conditions for the various coupling reactions, but can be cleaved at the end under mild conditions that do not affect the fragile arabinoside linkages.

Compounds of Formula II.

Compositions of formula II may be obtained from precursor 19. Precursor 19 can be prepared according to one embodiment of the present invention, which is presented in Scheme 5.

SCHEME 5
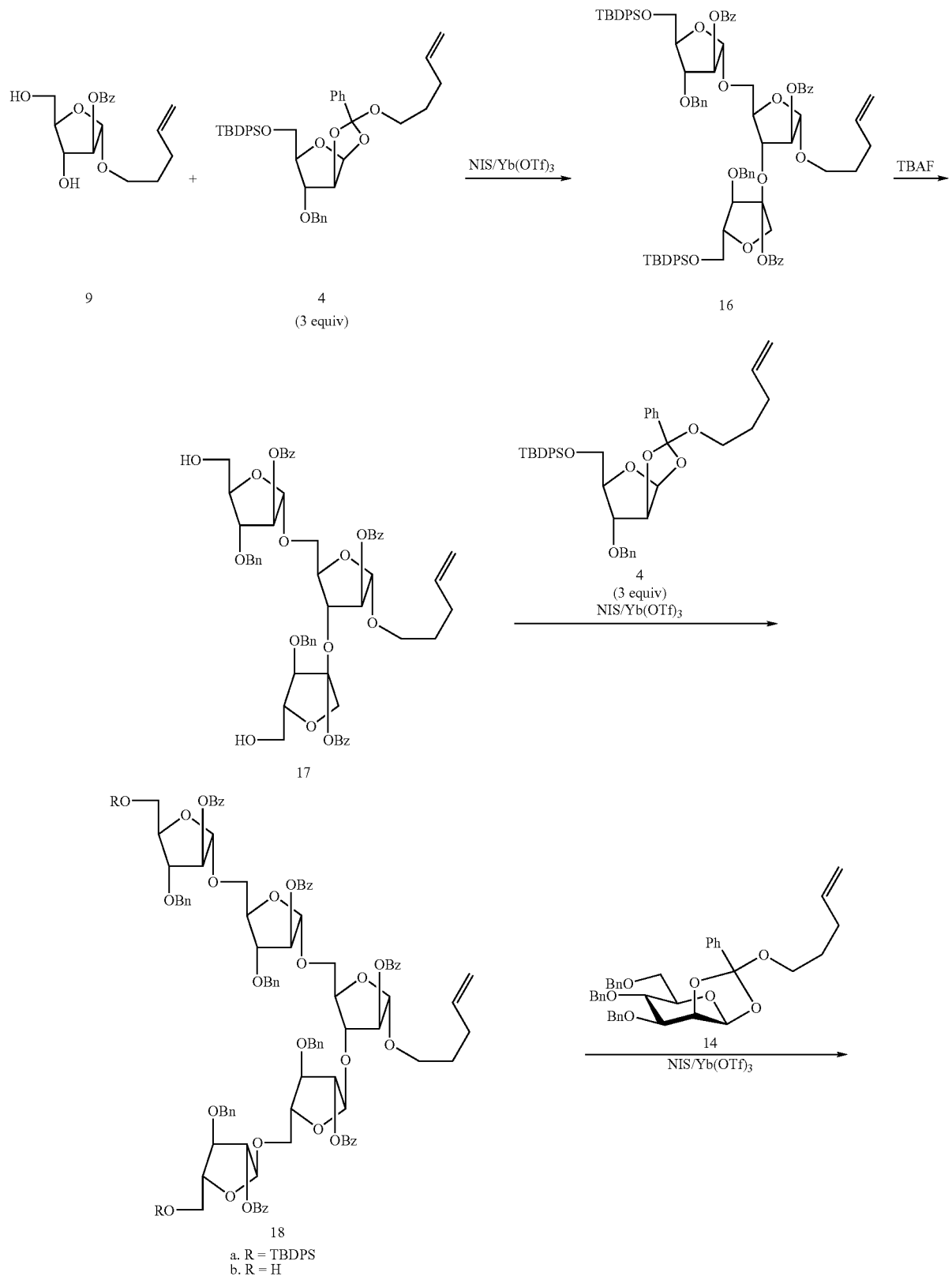

-continued

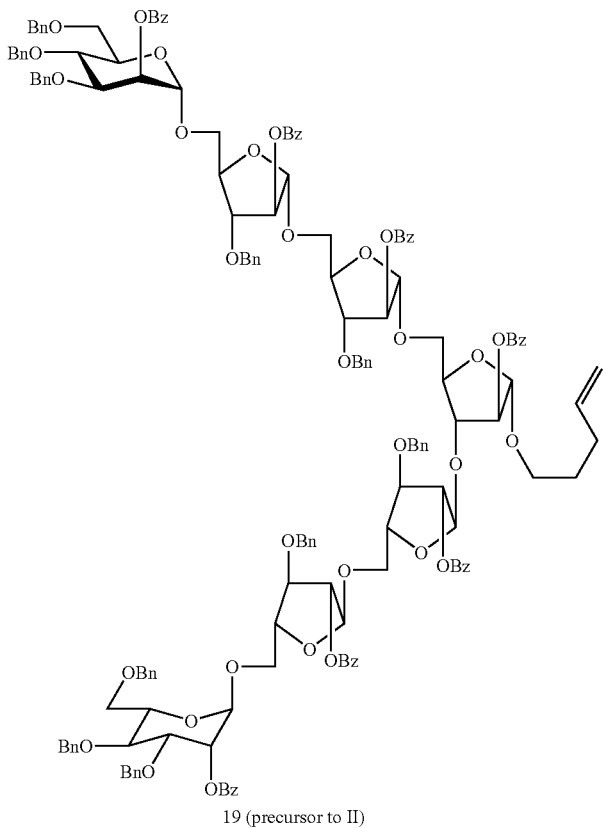

19 (precursor to II)

For compounds of formula II the starting material is the diol 9. Both hydroxyl groups were glycosylated with the orthoester 4, affording the branched trisaccharide 16. Cleavage of the silyl groups of 16 freed the two primary hydroxyls in 17, and double glycosidation with the donor, 4, gave 18a. Desilylation afforded the pentasaccharide diol 18b. Capping with the mannose orthoester 14, then gives one embodiment of a compound of formula VI (19) and a precursor to compounds of formula II.

As described previously, the compounds of formula VI can be of any length. Accordingly, in some embodiments of the present invention, the number of glycosylation reactions can be varied to produce compounds similar to the embodiments presented in Scheme 5, above, but having a greater or lesser number of arabinose groups.

In the embodiments presented in Scheme 5, the hydroxyl protecting groups are presented as benzyl and benzoate protecting groups. In other embodiments, the protecting groups can be any other hydroxyl protecting groups that can be removed selectively from one another and be stable to the conditions for the various coupling reactions, but can be cleaved at the end under mild conditions that do not affect the fragile arabinoside linkages.

Scheme 5 shows one embodiment of the invention in which formation of compounds 16, 18 and 19 is carried out using Ytterbium (III) triflate in the presence of N-iodosuccinimide (Yb(OTf)$_3$/NIS). In further embodiments, catalysis by Ytterbium (III) triflate is carried out in the presence of N-bromosuccinimide (NBS), bromine, a divalent mercury salt, and/or any like oxidizing agent.

Compounds of Formula III.

An additional embodiment of the invention is presented in Scheme 6. Compositions of formula III may be obtained from precursor 24, which can be prepared as indicated in Scheme 6.

SCHEME 6
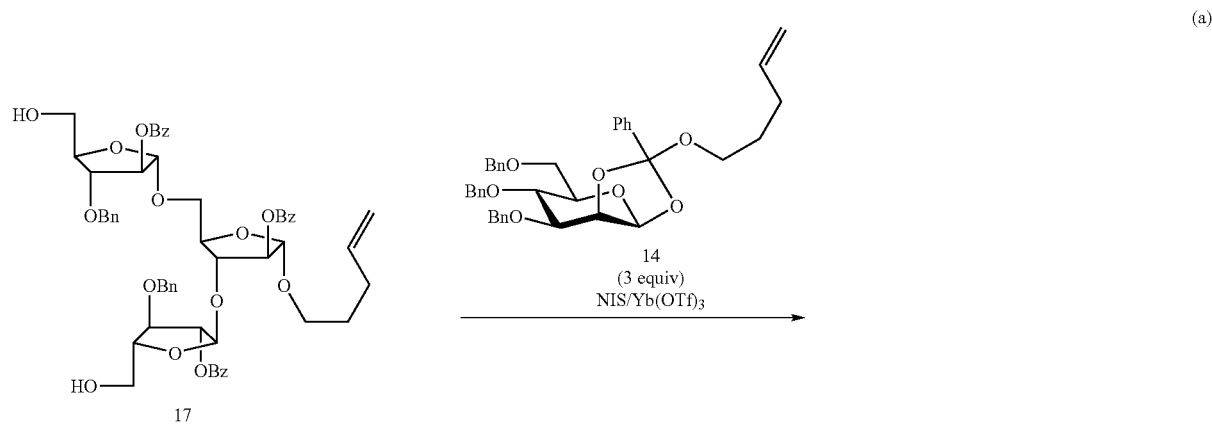
(a)
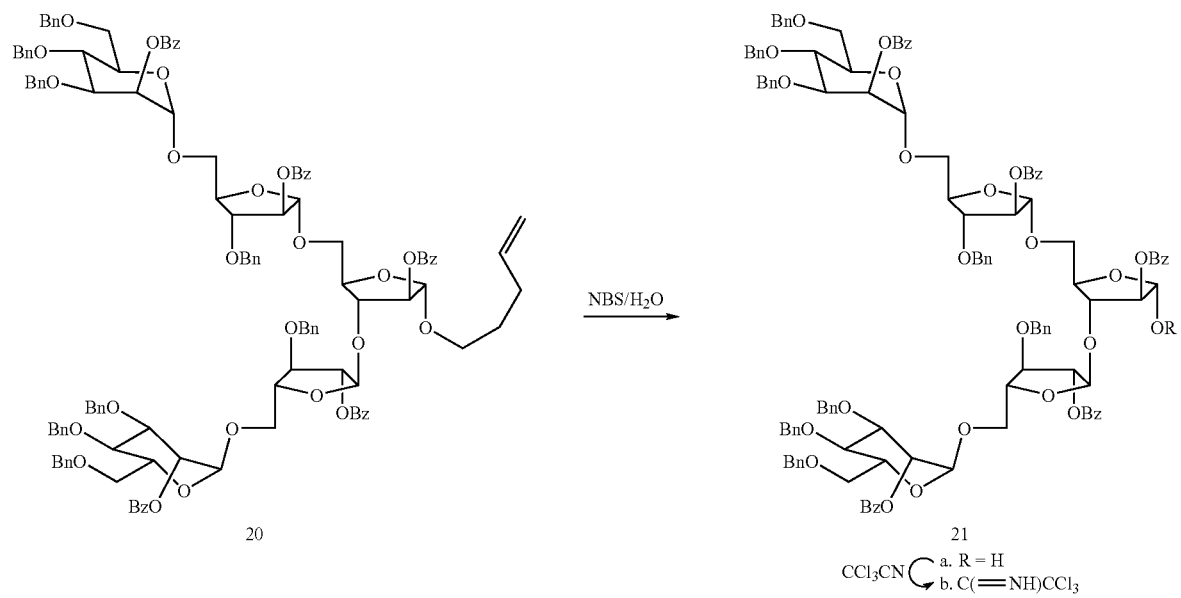
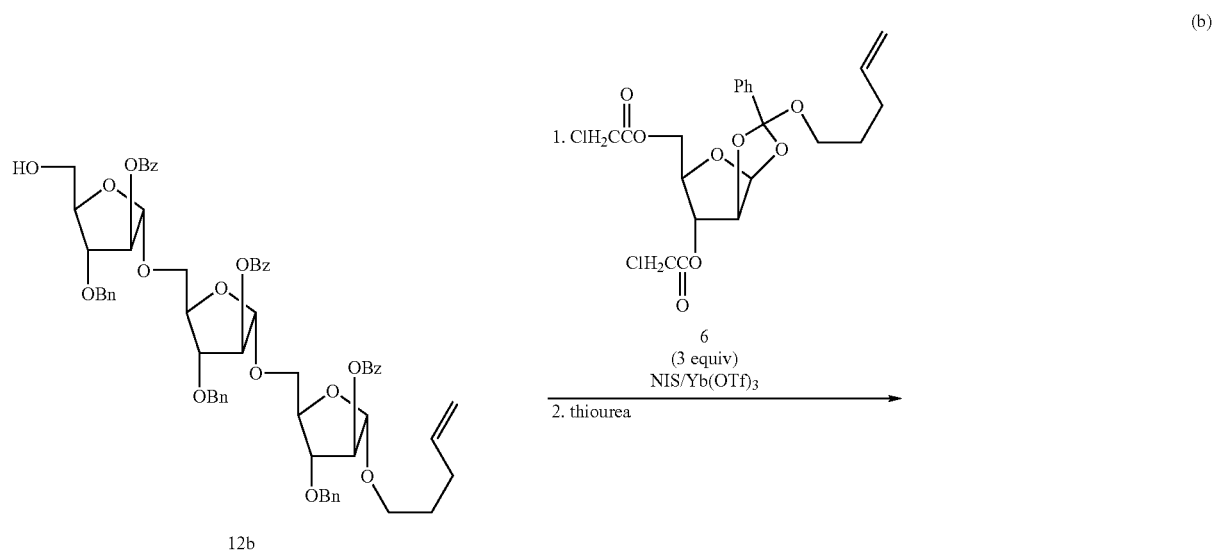
(b)

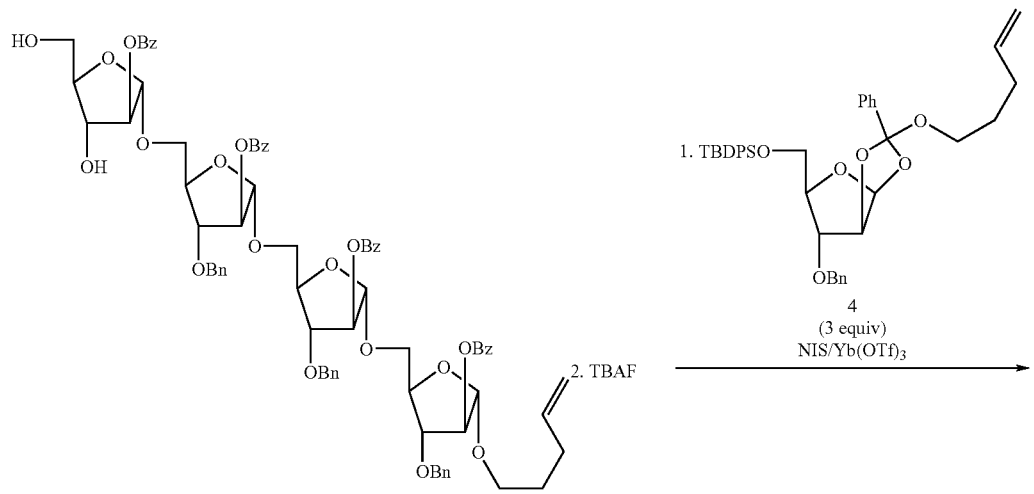
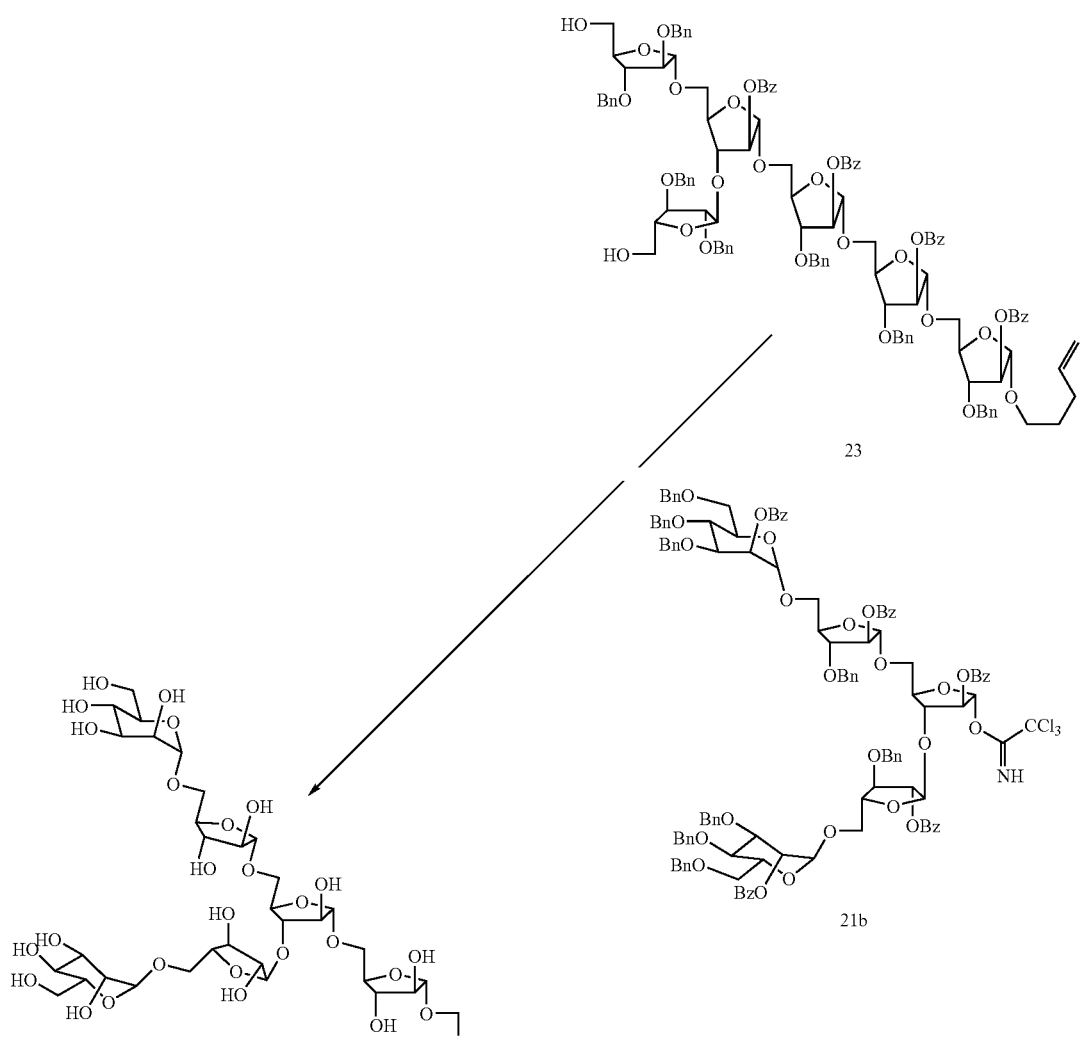

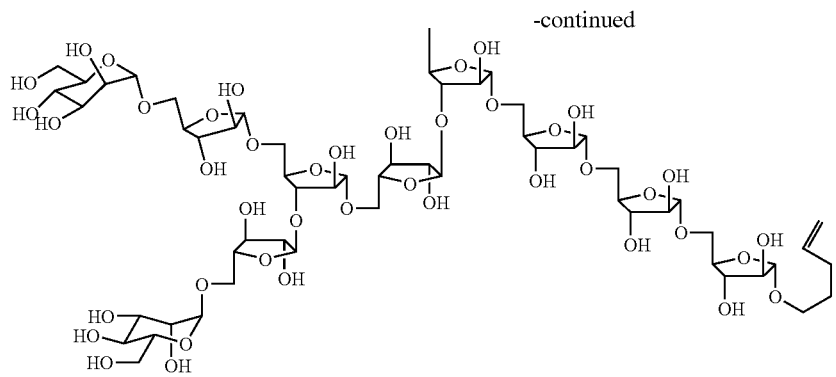

24 (Precursor to III)

The trisaccharide 17 prepared as shown in Scheme 5, was capped with the mannose orthoester 14 to a give the pentasaccharide 20. The pentenyl glycosidic linkage was cleaved by oxidative hydrolysis to give 21a. The anomeric hydroxyl was condensed with trichloroacetonitrile to give the trichloroacetimidate 21b (Scheme 6a). In additional embodiments, prior to capping with the mannose orthoester 14, compound 17 can first be further glycosylated as previously described (Scheme 5) to produce arabinan compounds with a greater or lesser number of arabinan groups as compared to compound 17. Thus, in one embodiment, a compound such as compound 19 can be used in Scheme 6a, wherein n and/or m are 1, 2, 3, or greater. In other embodiments of the invention, n and/or m are 20 or less. Thus, n and m are each independently 1, 2, 3, 4, 5, 6, 7, 8, 9, 10, 11, 12, 13, 14, 15, 16, 17, 18, 19, or 20. In further embodiments of the present invention, n and/or m are each independently an integer in a range from about 1-20, 1-15, 1-12, 1-10, 1-8, 1-5, 1-3 and the like.

In Scheme 6, part (b), the trisaccharide 12b, as prepared in Scheme 4, was reacted with orthoester 6, and the product was dechloroacetylated, which gave the tetrasaccharide diol 22. The dechloroacylation or deacylation was carried out with thiourea. In other embodiments, the dechloroacylation or deacylation is carried out with thiosemicarbizide. Both hydroxyl groups of 22 were glycosidated with orthoester 4, and the product desilylated giving diol hexasaccharide 23. Compound 23 is then glycosidated with excess trichloroacetimidate 21b to afford the 16-mer 24, which is one embodiment of the compound of formula VII and a precursor to the compound of formula III.

As described previously, the compounds of formula VII can be of any length. Accordingly, in additional embodiments of the invention, the number of glycosylation reactions can be varied to produce compounds corresponding to the embodiments presented in Scheme 6 but with a greater or lesser number of arabinan groups; thus, providing additional embodiments of the invention and additional precursors to formula III.

In the embodiment presented in Scheme 6, the hydroxyl protecting groups are presented as benzyl and benzoate protecting groups. In other embodiments, the protecting groups can be any other hydroxyl protecting groups that can be removed selectively from one another, be stable to the conditions for the various coupling reactions, but can be cleaved at the end under mild conditions that do not affect the fragile arabinoside linkages.

Scheme 6 shows one embodiment of the invention in which reactions with Ytterbium (III) triflate are carried out in the presence of N-iodosuccinimide (Yb(OTf)$_3$/NIS). In further embodiments, catalysis by Ytterbium (III) triflate is carried out in the presence of NBS, bromine, a divalent mercury salt, and/or any like oxidizing agent.

Compounds of Formula IV.

The basic procedure for making the dendrimer precursor to formula IV, the compound of formula VIII, or compound 27, follows the chemistry used in Scheme 6. This is presented in two further embodiments of the present invention shown in Scheme 7 and Scheme 8.

SCHEME 7

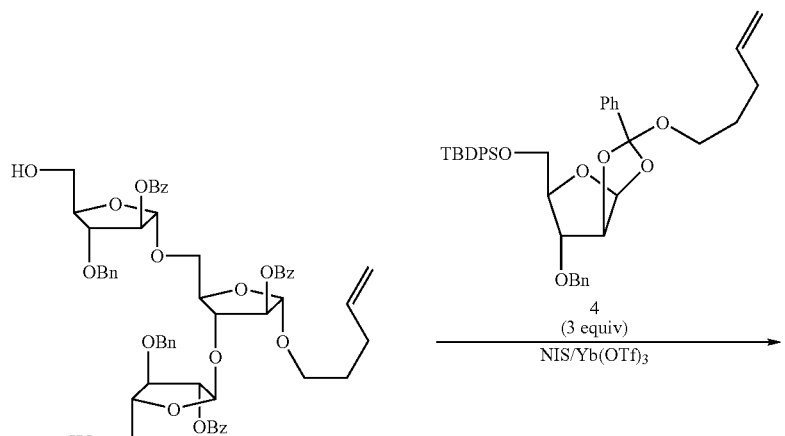

-continued
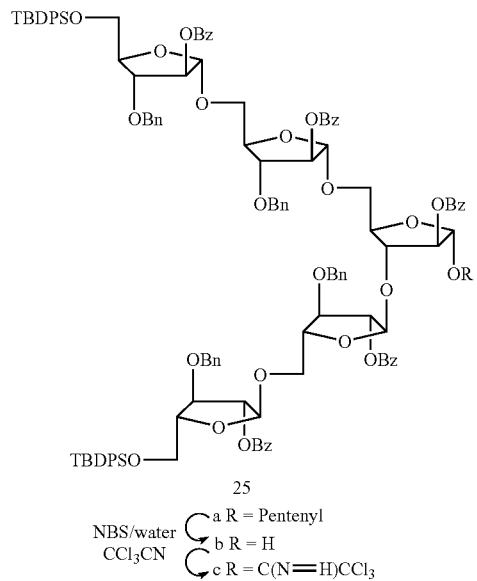
25
NBS/water
CCl₃CN
  a R = Pentenyl
  b R = H
  c R = C(N=H)CCl₃
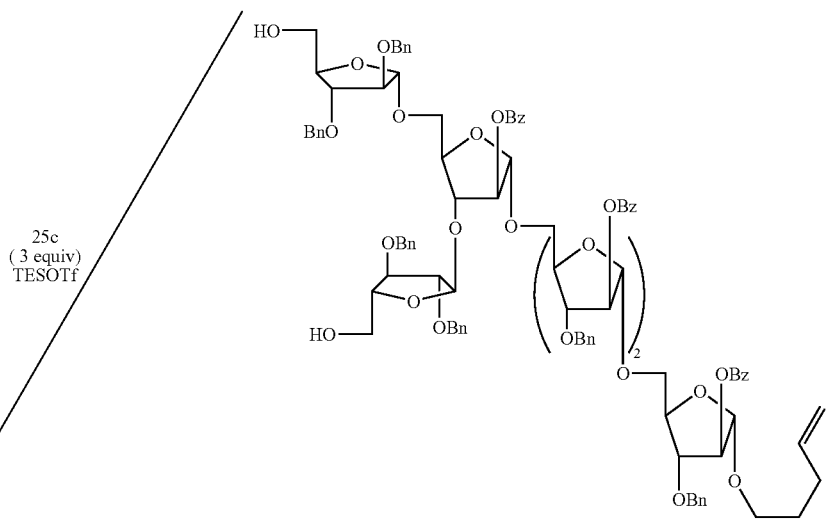
23
25c
(3 equiv)
TESOTf
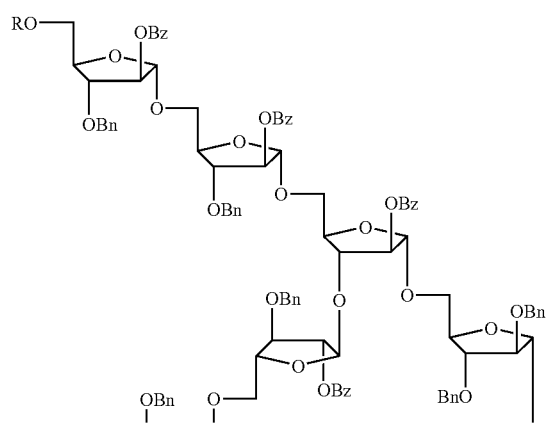

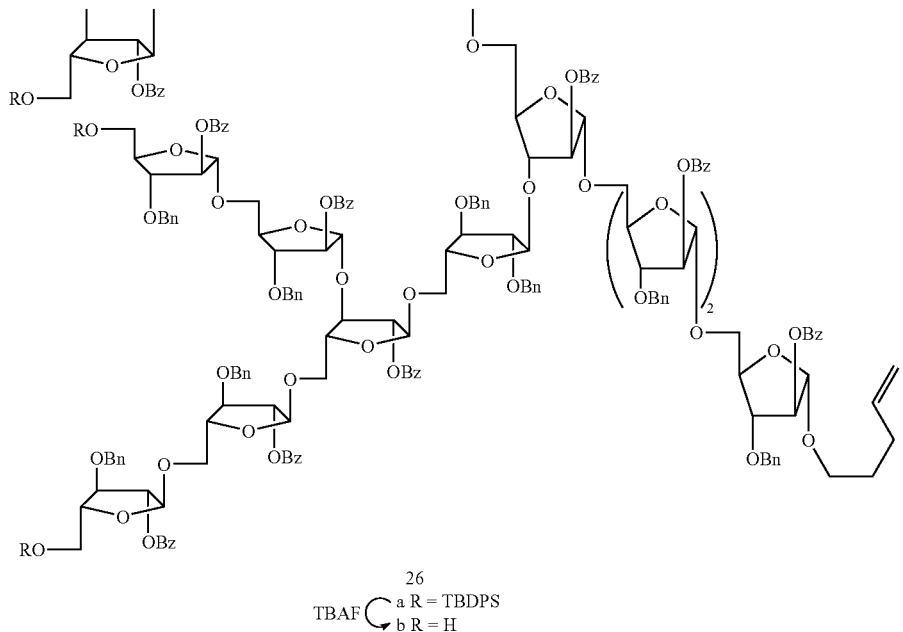

In the embodiment presented in Scheme 7, the trisaccharide 17 was capped with the arabinose orthoester 4 to a give the pentaarabinan 25a. The pentenyl glycosidic linkage of compound 25a was cleaved by oxidative hydrolysis to give 25b, the anomeric hydroxyl, which was condensed with trichloroacetonitrile to give the trichloroacetimidate 25c.

As shown in Scheme 7, the primary hydroxyls of hexasaccharide diol 23 are then glycosidated with excess trichloroacetimidate 25c using Yb(OTf)$_3$ to afford the 16-mer 26a, and after desilylation, 26b. In other embodiments, the glycosylation of compound 23 is carried out using TESOTF. The tetraol (26b) can now serve as the acceptor for the previously prepared mannose-capped trichloroacetimidate donor, pentasaccharide 21b, as shown in the embodiment of the invention presented in Scheme 8.

SCHEME 8

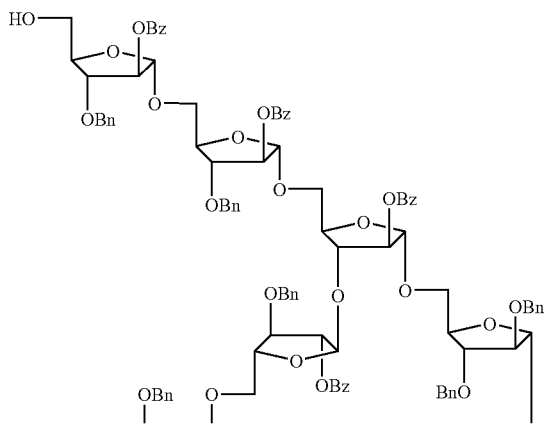

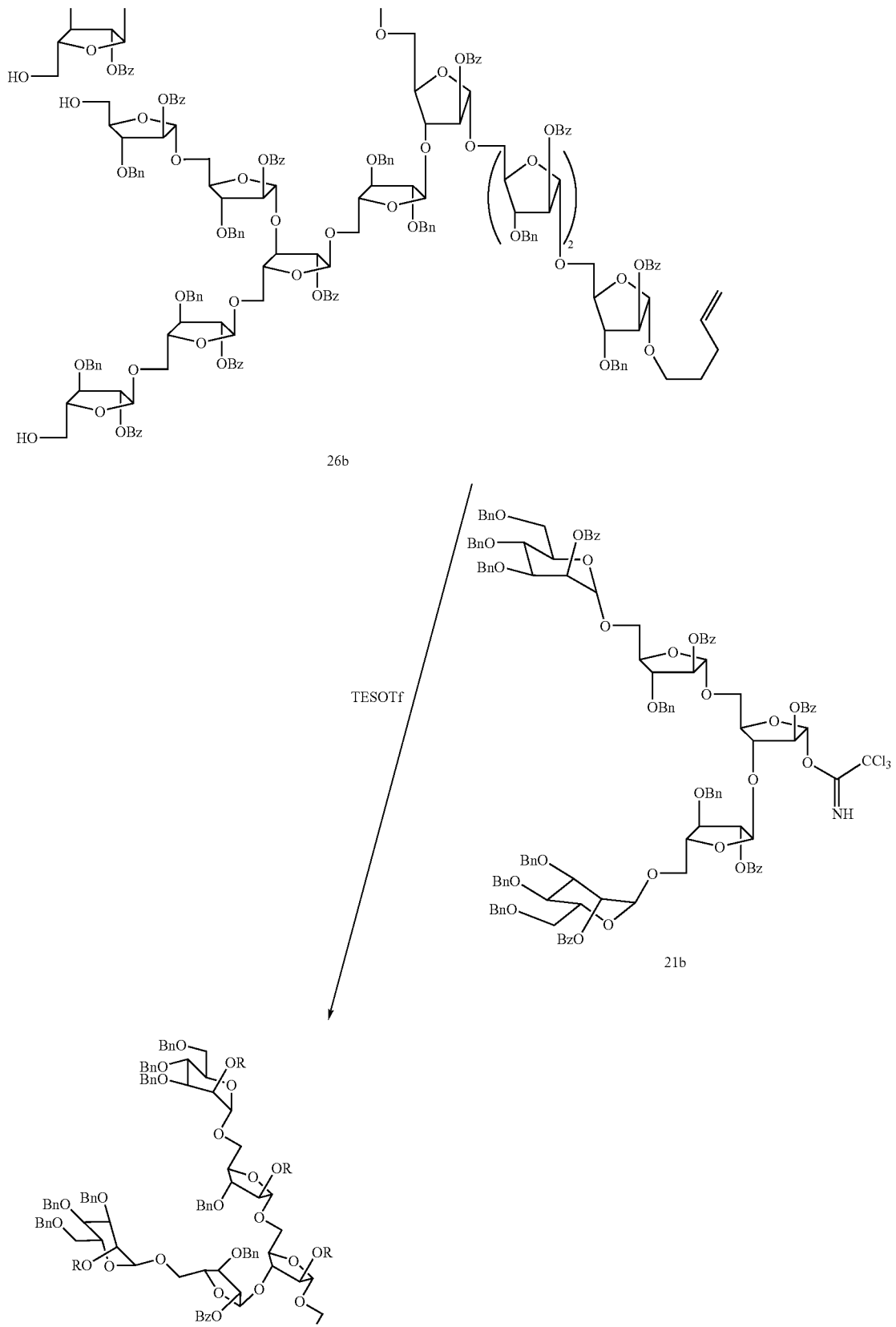

-continued

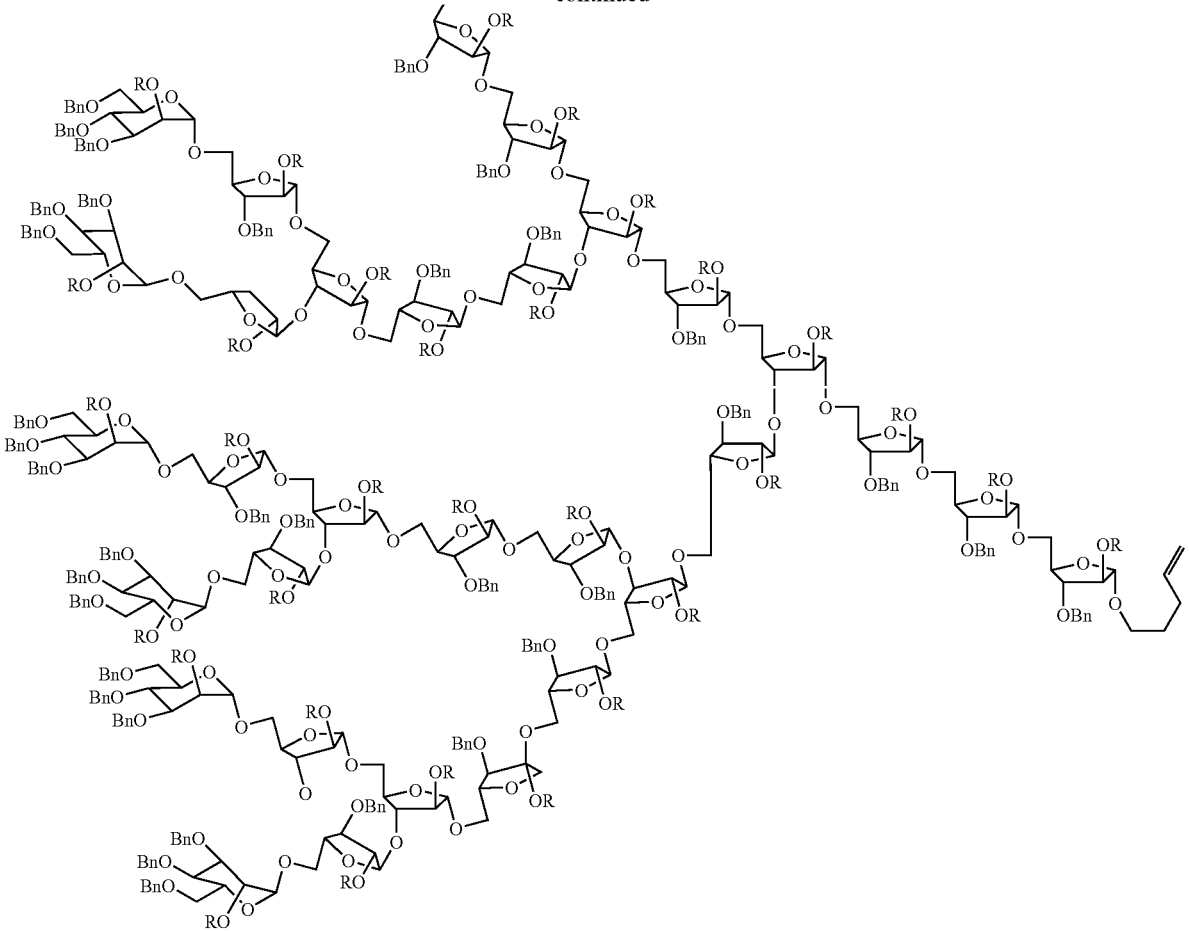

27 (precursor to IV)

R = Bz

The result of reacting compound 26b with compound 21b was the 36-mer 27 which is a compound of formula VIII and a precursor to IV.

As described previously, the compounds of formula VIII can be of any length. Accordingly, in additional embodiments of the invention, the number of glycosylation reactions can be varied to produce compounds corresponding to the various intermediates shown in Schemes 7 and 8, but with a greater or lesser number of arabinan groups; thus, providing additional embodiments of the invention and additional precursors to formula IV.

In the embodiments presented in Scheme 7 and 8, the hydroxyl protecting groups are presented as benzyl and benzoate protecting groups. In other embodiments, the protecting groups can be any other hydroxyl protecting group that can be removed selectively from one another, be stable to the conditions for the various coupling reactions, but can be cleaved at the end under mild conditions that do not affect the fragile arabinoside linkages.

Conversion of Compounds of Formula V, VI, VII, and VIII (Precursors 15, 19, 24 and 27) into Compounds of Formula I, II, II and IV, Respectively (Scheme 9)

In some embodiments of the present invention, the compounds of formula V, VI, VII, and VIII (precursors 15, 19, 24 and 27) each have several benzoate esters, and terminate at the reducing ends with n-pentenyl groups. Thus, the compounds of formula V, VI, VII, and VIII (precursors 15, 19, 24 and 27) are collectively represented by structure 28a in Scheme 9.

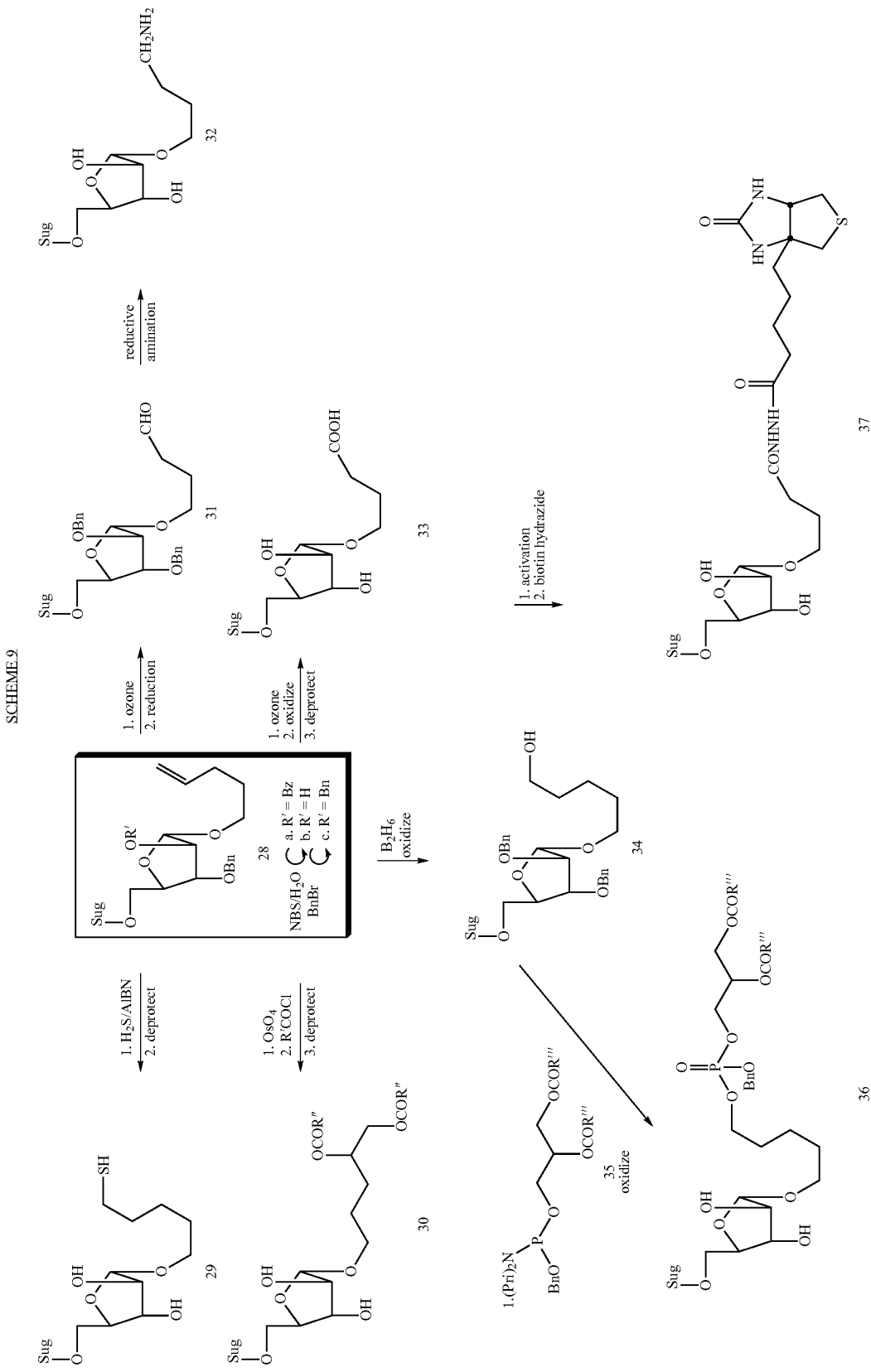

"Sug" in Scheme 9 refers to any of the compounds of formulas V, VI, VII and VIII. Thus, compound 28 represents the benzoate esters of the precursor compounds of formulas V, VI, VII and VIII. The R" and R'" of Scheme 9 are aliphatic alkyl groups of any type.

In order to convert compounds of formulas V-VIII (precursors) to compounds of formula I-IV, all benzoate groups are removed by saponification with sodium methoxide or a similar base, to give free-OH groups, as in 28b. The free hydroxyl groups are then benzylated, as in 28c. Free-radical reaction of 28b with hydrogen sulfide ($H_2S$) and azobisisobutyl nitrile (AIBN) followed by cleavage of the benzyl protecting groups gives 29. Dihydroxylation of 28b and acylation of the resulting hydroxyl groups is carried out using acylating agents of any type, including, but not limited to, acetic anhydride, and benzoyl chloride and the like. Acylation is followed by cleavage of the benzyl protecting groups giving diester 30. Ozonolysis of 28b followed by reduction gives aldehyde 31, and reductive amination along with cleavage of the benzyl protecting groups gives amine 32. Ozonolysis and oxidation of 28b followed by cleavage of the benzyl protecting groups gives carboxylic acid 33. Hydroboration of 28a followed by oxidation gives primary alcohol 34. The primary alcohol 34 is treated with phosphoamidite 35, followed by cleavage of the benzyl protecting groups, giving phosphodiester 36. Activation of carboxylic acid 33 followed by reaction with biotin hydrazide gives the biotinylated compounds 37.

The length of the reducing end O-glycosidic alkyl chains can be varied by applying the Grubbs' reaction to alkene 28c, and/or the Witting reaction to the aldehyde 31 as summarized in the embodiments presented in Scheme 10.

include, but are not limited to, methyl, ethyl, n-propyl, isopropyl, n-butyl, phenyl, benzyl and combinations thereof.

The resulting chain-lengthened alkene 38 is then processed as indicated in Scheme 10 to give the compounds of Formulas I, II, III and IV. "Sug" in Scheme 10 refers to any and all of the compounds of formulas V, VI, VII and VIII.

The present invention is explained in greater detail in the following non-limiting Examples.

EXAMPLES

Example 1

Preparation of Compound 2

To a solution of 2,3,5-tri-O-benzoyl-α-D-arabinofuranosyl bromide 1c [14] (5.0 g, 9.5 mmol) in $CH_2Cl_2$ (50 mL) were added lutidine (2.2 g, 21 mmol), n-pentenyl alcohol (1.63 g, 19 mmol) and $Bu_4NI$ (2 g). The solution was refluxed under Ar for 72 h. Water was added to the mixture and the aqueous phase was extracted with $CH_2Cl_2$ (50 mL). The organic phase was dried ($Na_2SO_4$) and evaporated. The residue was purified by column chromatography (Hexane: EtOAc; 6:1) to give product 2 (3.5 g, 70%) as isomers (3:1) $^1$H NMR (300 MHz, $CDCl_3$) δ 7.34-8.06 (m, 15H, Ar—H), 6.35 (d, J=3.0 Hz, 1H), 5.76 (m, 1H), 5.53 (s, 1H), 4.92-5.10 (m, 3H), 4.76-4.78 (t, J=3.6, 3.6 Hz, 1H), 4.61-4.64 (t, J=5.4, 5.4 Hz, 1H), 4.26 (d, J=5.7 Hz, 1H0, 4.14-4.18 (dd, J=3.3, J=10.2 Hz, 1H), 3.29-3.44 (m, 2H), 2.04-2.13 (m, 2H), 1.57-1.69 (m, 2H). $^{13}$C NMR (75 MHz, $CDCl_3$) δ: 166.1, 165.5, 133.9, 133.3, 130.1, 129.9, 129.9, 128.8, 128.7, 128.7, 128.6, 128.6,

SCHEME 10

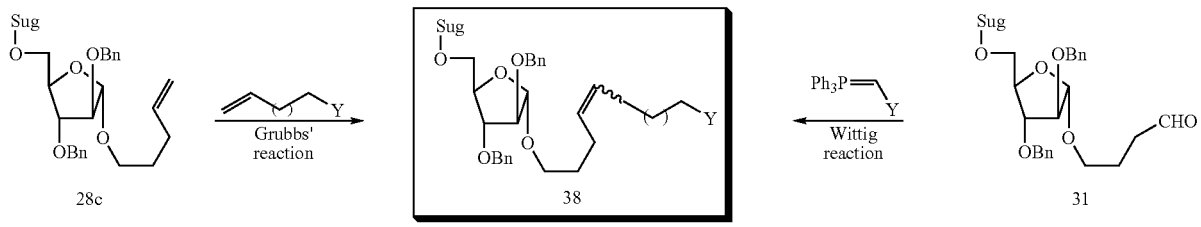

wherein Y an attachment group. In some embodiments, the attachment group Y is selected from the group consisting of:

a) $OCH_2(CH_2)_oCH_2SH$,
b) $OCH_2(CH_2)_oCHCH_2OCOR'$
      |
      $OCOR'$,
c) $OCH_2(CH_2)_oCOOH$,
d) $OCH_2(CH_2)_oCH_2NH_2$,
e) $OCH_2(CH_2)_oCH_2OPhosphodiacylglyceryl$, and
f) $OCH_2(CH_2)_oCH_2\ NH_2$-Biotin.

The alkyl unit of attachment groups a) through t) can be of any length. Thus, o is 1, 2, 3, or greater. In other embodiments of the invention o is 20 or less. Thus, o is 1, 2, 3, 4, 5, 6, 7, 8, 9, 10, 11, 12, 13, 14, 15, 16, 17, 18, 19, or 20. In further embodiments of the present invention, o is an integer in a range from about 1-20, 1-15, 1-12, 1-10, 1-8, 1-5, 1-3 and the like. R' is any carboxylic ester wherein the carboxylic ester comprises alkyl, aryl, alkyl aryl, or aryl alkyl groups that 128.6, 126.5, 126.3, 115.2, 106.6, 85.0, 84.3, 77.9, 64.0, 63.3, 30.4, 28.8. MS MALDI: Calcd for $C_{31}H_{36}O_8$ 530.19, Found 553.1 ($M+Na^+$).

Example 2

Preparation of Compound 3

Compound 2 (3.5 g, 6.6 mmol) was dissolved in a solution of $CH_2Cl_2$/MeOH (1:1, 20 mL) and NaOMe (25% in MeOH, 5 mL) was added and the mixture was stirred at r.t. for 2 h. The solvent was evaporated. The residue was diluted with $CH_2Cl_2$ (50 mL) and was washed with $H_2O$ (20 mL). The organic phase was dried and was evaporated. The residue was purified by column chromatography (Hexane:EtOAc 2:1→1:1) to give compound 3 as one isomer (1.5 g, 75%). $^1$H NMR (300 MHz, $CDCl_3$) δ: 8.00 (m, 1H), 7.32-7.61 (m, 4H), 6.08 (d, J=0.9 Hz, 1H), 5.73-5.88 (m, 1H, —CH═$CH_2$), 4.94-5.07 (m, 2H), 4.67-4.68 (m, 1H), 4.38-4.47 (m, 1H), 3.63-4.17 (m, 3H), 2.08-2.17 (m, 2H), 1.61-1.74 (m, 2H). $^{13}$C NMR (75 MHz, $CDCl_3$) δ: 129.9, 129.9, 129.6, 128.7, 128.6, 128.2, 125.9, 115.1, 103.9, 84.0, 83.8, 77.2, 68.6, 62.6, 32.0, 30.3; MS MALDI: Calcd for $C_{17}H_{22}O_6$ 322.1 Found 344.8 (M+Na$^+$).

Example 3

Preparation of Compound 4

To a solution of compound 3 (600 mg, 1.93 mmol) in $CH_2Cl_2$ (20 mL) DMAP (100 mg), triethylamine (2 mL) was added TBDPSiCl (638 mg, 2.32 mmol). The mixture was stirred at r.t. until completion (TLC), and the solvent was evaporated. The residue was purified by column chromatography (Hexane:EtOAc 2:1) to give TBDPS protected compound (666 mg, 62%). $^1$H NMR (300 MHz, CDCl$_3$) δ: 7.15-7.70 (m, 15H), 6.14 (d, J=3.9 Hz, 1H), 5.66-5.79 (m, 1H, —CH=CH$_2$), 4.89-4.99 (m, 2H), 4.79 (d, J=4.5 Hz, 1H), 4.39 (s, 1H), 4.06-4.14 (m, 1H), 3.51-3.56 (dd, J=5.4 Hz, J=10.2 Hz, 1H), 3.43 (t, J=9.3, 9.3 Hz, 1H), 3.19-3.33 (m, 2H), 2.01-2.09 (m, 2H), 1.55-1.64 (m, 2H), 0.95 (s, 9H). $^{13}$C NMR (75 MHz, CDCl$_3$) δ: 138.1, 135.5, 135.5, 134.9, 129.8, 129.7, 129.2, 128.2, 127.9, 127.8, 127.7, 126.3, 122.7, 115.0, 106.2, 89.2, 87.2, 76.1, 63.9, 63.0, 46.1, 30.5, 28.9, 27.1, 19.5.

To a solution of TBDPS protected compound (600 mg, 1.07 mmol) in DMF (5 mL) at 0° C. was added NaH (64 mg, 1.61 mmol) and the mixture was stirred for 5-10 min. BnBr (165 mL, 1.39 mmol) was added dropwise and the mixture was stirred until completion (TLC). Water (5 mL) was added to quench the reaction. The aqueous phase was extracted by ether (2×50 mL). The organic phase was washed with water (25 mL) and was dried. The solvent was evaporated and the residue was purified by column chromatography (Hexane: EtOAc 10:1) to give compound 4 (560 mg, 80%). $^1$H NMR (300 MHz, CDCl$_3$) δ 7.13-7.48 (m, 20H, Ar—H), 6.15 (d, J=4.2 Hz, 1H), 5.65-5.79 (m, 1H, —CH=CH$_2$), 4.89-4.99 (m, 3H), 4.58 (s, 2H), 4.28-4.33 (m, 1H), 4.17 (s, 1H), 3.54 (dd, J=5.4 Hz, J=9.9 Hz, 1H), 3.40 (t, J=9.9, 9.9 Hz, 1H), 3.19-3.35 (m, 2H), 2.01-2.09 (m, 2H), 1.55-1.64 (m, 2H), 0.9 (s, 9H). $^{13}$C NMR (75 MHz, CDCl$_3$) δ 138.0, 137.3, 136.3, 135.4, 135.4, 133.3, 133.2, 129.7, 129.6, 129.2, 128.6, 128.1, 128.0, 127.7, 127.7, 127.7, 126.2, 122.6, 115.0, 106.4, 86.8, 85.3, 82.8, 71.7, 63.8, 62.9. 30.4, 28.9, 27.0, 19.4. MS MALDI: Calcd for $C_{40}H_{46}O_6Si$ 650.3, Found 672.9 (M+Na$^+$).

Example 4

Preparation of Compound 5

To a solution of diol 3 (950 mg, 3.06 mmol) in DMF (10 mL) at 0° C. was added NaH (490 mg, 12.1 mmol), and the mixture was stirred for 5 min. BnBr (1.1 mL, 9.2 mmol) was added. The mixture was stirred until the diol 3 had been consumed (TLC). Water (2 mL) was added to quench the reaction. The mixture was diluted with ether (2×20 mL). The organic phase was washed with water and was dried. The solvent was evaporated, and the residue was purified by column chromatography to give 5 (1.14 g, 78%). $^1$H-NMR (400 MHz, CDCl$_3$), δ 7.56 (m, 2 h), 7.24-7.35 (M, 11 h), 7.16-7.14 (M, 2 h), 6.18 (d, J=4.4 Hz, 1H), 5.73 (m, 1H, —CH=CH$_2$), 4.92-4.99 (m, 2H), 4.56 (s, 2H), 4.37 (d, J=7.6 Hz, 1H), 4.31 (d, J=12 Hz, 1H), 4.21 (d, J=12 Hz, 1H), 3.99 (d, J=1.6 Hz, 1H), 3.18-3.38 (m, 3H), 3.18 (dd, J=7.6 Hz, 10 Hz, 1H), 2.04-2.09 (m, 2H), 1.57-1.65 (m, 2H). $^{13}$C NMR (100 MHz, CDCl$_3$) δ 138.0, 138.0, 137.2, 136.84, 129.3, 128.6, 128.4, 128.2, 128.0, 127.9, 127.7, 127.7, 126.4, 122.8, 115.0, 106.3, 85.2, 84.8, 82.8, 73.2, 71.6, 70.0, 62.8, 30.3, 28.7; MS MALDI: Calcd for $C_{31}H_{34}O_6$ 502.2, Found 525.2 (M+Na$^+$).

Example 5

Preparation of Compound 6

To a solution of 3 (645 mg, 2.08 mmol), pyridine. (1 mL) and DMAP (50 mg) in $CH_2Cl_2$ (10 mL) at −10° C. was added $(ClAc)_2O$ (1.07 g, 6.24 mmol). The mixture was stirred for 30 min at −10° C. until completion (TLC). Water (2 mL) was added to quench the reaction. The aqueous phase was extracted with $CH_2Cl_2$ (2×10 mL). The organic phase was dried ($Na_2SO_4$) and was evaporated. The residue was purified by column chromatography (Hexane: EtOAc: Et$_3$N, 4:1:0.1) to give compound 6 (706 mg, 73%). $^1$H NMR (300 MHz, CDCl$_3$) δ 7.48-7.52 (m, 2H), 7.27-7.31 (m, 3H), 6.12 (d, J=6.0 Hz, 1H), 5.58-5.71 (m, 1H), 5.11-5.12 (d, J=0.6 Hz, 1H), 4.90-4.92 (m, 1H), 4.86 (s, 1H), 4.83 (m, 1H), 4.24 (t, J=7.2, 7.2 Hz, 1H), 4.00 (s, 1H), 3.96 (d, J=6.9 Hz, 1H), 3.89 (d, J=1.8 Hz, 1H), 3.20 (m, 2H), 1.97 (m, 1H), 3.89 (d, J=1.8 Hz, 1H), 3.20 (m, 2H), 1.97 (m, 1H), 1.52 (m, 2H). $^{13}$C NMR (75 MHz, CDCl$_3$) δ 166.7, 166.2, 137.8, 135.5, 129.7, 128.4, 128.6, 126.1, 123.1, 115.0, 106.3, 84.3, 83.4, 78.7, 64.5, 32.2, 40.7, 40.6, 30.3, 28.7. MS (MALDI) for $C_{21}H_{24}Cl_2O_8$ Calcd. 474.0, Found 473.0 (M−H$^+$).

Example 6

Preparation of Compound 7a

Compound 4 (500 mg, 0.77 mmol) was dissolved in $CH_2Cl_2$ (5 mL). The solution was cooled to 0° C. and TBDP-SOTf (30 µL) was added. The mixture was stirred for 1 h or until completion (TLC). Triethylamine (1 mL) was added to quench the reaction. The solvent was evaporated and the residue was purified by column chromatography (Hexane: EtOAc, 5:1) to give compound 7a (450 mg, 90%). $^1$H NMR (300 MHz, CDCl$_3$) δ: 7.95 (m, 2H), 7.49-7.67 (m, 3H), 7.16-7.38 (m, 10H), 5.74-5.87 (m, 1H, —CH=CH$_2$), 5.40 (d, J=1.2 Hz, 1H), 5.15 (s, 1H), 4.91-5.05 (m, 2H), 4.79 (d, J=12 Hz, 1H), 4.56 (d, J=12 Hz, 1H), 4.26 (m, 1H), 4.14 (m, 1H), 3.84 (d, J=4.2 Hz, 2H), 3.76 (m, 1H), 3.49 (m, 1H), 2.21-2.19 (m, 2H), 1.69-1.78 (m, 2H), 1.01 (s, 9H). $^{13}$C NMR (75 MHz, CDCl$_3$) δ: 165.5, (C=O), 138.2, 137.8, 135.7, 135.7, 133.4, 133.3, 129.8, 129.7, 128.5, 128.4, 128.0, 127.7, 127.7, 114.9, 106.2, 83.5, 83.3, 82.4, 72.4, 66.9, 63.5, 30.5, 28.9, 27.0, 19.6. MS MALDI: Calcd for $C_{40}H_{46}O_6Si$ 650.3, Found 673.3 (M+Na$^+$).

Example 7

Preparation of Compound 7b

A solution of compound 7a (450 mg, 0.69 mmol), acetic acid (229 mg, 3.82 mmol) and TBAF (1M, 3.82 mL, 2.82 mmol) in THF (10 mL) was stirred at r.t. overnight. The solvent was evaporated and the residue was purified by column chromatography (Hexane: EtOAc, 3:1) to give compound 7b (234 mg, 82%). $^1$H NMR (300 MHz, CDCl$_3$) δ: 7.97-8.00 (m, 2H), 7.67-7.70 (m, 1H), 7.50-7.54 (m, 1H), 7.18-7.41 (m, 6H), 5.72-5.85 (m, 1H, —CH=CH$_2$), 5.36 (d, J=1.5 Hz, 1H), 5.10 (s, 1H), 4.92-5.04 (m, 2H), 4.77 (d, J=11.7 Hz, 1H), 4.56 (d, J=11.7 Hz, 1H), 4.20-4.24 (m, 1H), 4.04-4.06 (m, 1H), 3.82 (dd, J=2.7 Hz, J=12 Hz, 1H), 3.70-3.73 (m, 1H), 3.62-3.68 (m, 1H), 3.41-3.48 (m, 1H), 2.10-2.17 (m, 2H), 1.0-1.75 (m, 2H). $^{13}$C NMR (75 MHz, CDCl$_3$) δ: 165.4, 138.1, 137.6, 134.8, 133.4, 129.7, 128.5, 128.4, 127.8, 127.6, 114.9, 106.2, 83.1, 82.5, 82.2, 72.5, 66.9, 62.0, 30.4, 28.8, 26.7. MS MALDI: Calcd for $C_{24}H_{28}O_6$ 412.1, Found 435.1 (M+Na$^+$).

Example 8

Preparation of Compound 8

To a solution of 5 (850 mg, 137 mmol) in $CH_2Cl_2$ (5 mL) at 0° C. was added TBDPSOTf (10 μL). The solution was stirred until completion (TLC). The reaction was quenched by adding triethylamine (0.5 mL). The solvent was evaporated and the residue was purified to give compound 8 (773 mg, 91%). $^1$H NMR (400 MHz, $CDCl_3$), δ 7.97 (d, J=7.6 Hz, 2H)(, 7.55 (t, J=6.8 Hz, 6.8 Hz, 1H), 7.22-7.39 (m, 12H), 5.81 (m, 1H, —CH=$CH_2$), 5.38 (d, J=1.2 Hz, 1H), 5.17 (s, 1H), 5.01 (dd, J=1.6 Hz, 17.2 Hz, 1H), 4.95 (dd, J=0.8 Hz, 10 Hz), 4.78 (d, J=12 Hz, 1H), 4.49-4.59 (m, 3H), 4.33 (m, 1H), 4.02 (d, J=6 Hz, 1H), 3.77 (m, 1H), 3.66 (m, 1H), 3.59 (m, 1H), 3.49 (m, 1H), 2.15 (m, 2H), 1.73 (m, 1H). $^{13}$C NMR (100 MHz, $CDCl_3$) δ 165.6, 138.3, 138.1, 137.8, 133.4, 129.9, 129.6, 128.6, 128.5, 128.4, 128.0, 127.9, 127.8, 127.7, 115.0, 106.2, 83.5, 82.1, 82.4, 73.5, 72.3, 69.5, 66.9, 30.4, 28.8. MS MALDI: Calcd for $C_{31}H_{34}O_6$ 502.2, Found 524.7 ($M+Na^+$).

Example 9

Preparation of Compound 9

Compound 9 was prepared by rearrangement of 6 (Lu, J and Fraser-Reid, B, *Chem. Commun.* 2005, 862-864) to give 10 as described above for 4→7a, or 5→8. This was followed by de-chloroacylation using thiourea in methylene chloride. $^1$H NMR (300 MHz, $CDCl_3$) δ 6.95-7.96 (m, 5H), 5.76 (m, 1H), 4.92-5.18 (m, 4H), 3.74-4.21 (m, 6H), 3.47 (m, 1H), 3.23 (m, 1H), 2.09 (m, 2H), 1.69 (m, 2H). $^{13}$C NMR (75 MHz, $CDCl_3$) δ 166.51, 137.91, 133.54, 129.73, 129.04, 128.47, 115.01, 105.40, 85.96, 84.07, 76.40, 67.25, 61.92, 30.33, 28.72.

Example 10

Preparation of Compound 11a

Compound 7b (220 mg, 0.53 mmol) was dried by codistillation with toluene and was dissolved in $CH_2Cl_2$ (10 mL). The solution was cooled to 0° C. Under Ar, NIS (453 mg, 2.12 mmol) was added followed by $Yb(OTf)_3$ (99 mg, 0.16 mmol). Compound 4 (1.03 g, 1.6 mmol) in $CH_2Cl_2$ (5 mL) was added dropwise until the acceptor 7b was consumed. $Na_2S_2O_3$ solution (10 mL) was added to quench the reaction. The aqueous phase was extracted by $CH_2Cl_2$ (2×10 mL). The organic phase was dried and evaporated. The residue was purified by column chromatography to give compound 11a (398 mg, 77%). $^1$H NMR (300 MHz, $CDCl_3$) δ: 7.12-8.04 (m, 30H), 5.72-5.86 (m, 1H, —CH=$CH_2$), 5.45 (s, 1H), 5.41 (s, 1H), 5.29 (s, 1H), 5.15 (s, 1H), 4.92-5.03 (m, 2H), 4.79 (d, J=12 Hz, 1H), 4.62 (t, J=11.4 Hz, 2H), 4.45 (d, J=12.3 Hz, 1H), 4.36 (m, 1H), 4.09-4.20 (m, 3H), 3.93 (dd, J=3.9, 11.4 Hz, 1H), 3.77 (m, 4H), 3.75 (m, 1H), 2.11-2.18 (m, 2H), 1.67-1.76 (m, 2H), 0.98 (s, 9H). $^{13}$C NMR (75 MHz, $CDCl_3$) δ: 165.4, 165.2, 138.2, 137.7, 137.7, 135.6, 133.3, 133.2, 129.8, 129.7, 129.7, 129.6, 129.5, 128.5, 128.4, 128.3, 128.3, 127.8, 127.7, 127.7, 127.6, 114.9, 106.2, 106.1, 83.9, 83.5, 83.1, 82.3, 82.1, 81.6, 72.5, 72.1, 66.9, 65.6, 63.2, 30.4, 28.8, 27.0, 19.5. MS MALDI: Calcd for $C_{59}H_{64}O_{11}Si$ 976.4, Found 998.9 ($M+Na^+$).

Example 11

Preparation of Compound 11b

Compound 11a (290 mg, 0.30 mmol) was desilylated, procedure as described for compound 7b, to give compound 11b (182 mg, 83%). $^1$H NMR (300 MHz, $CDCl_3$) δ: 7.08-7.94 (m, 20H), 5.64-5.77 (m, 1H, —CH=$CH_2$), 5.29 (s, 2H), 5.17 (s, 1H), 5.05 (s, 1H), 4.82-4.95 (m, 2H), 44.72 (d, J=11.7 Hz, 1H), 4.53 (m, 2H), 4.39 (d, J=12.3 Hz, 1H), 4.25 (m, 1H), 4.05 (m, 1H), 3.99 (m, 1H), 3.89 (d, J=5.4 Hz, 1H), 3.83 (dd, J=3.9 Hz, 11.1 Hz, 1H), 3.67 (m, 3H), 3.47 (dd, J=4.2 Hz, J=12.3 Hz, 1H), 3.39 (m, 1H), 2.01-2.89 (m, 2H), 1.58-1.67 (m, 2H). $^{13}$C NMR (75 MHz, $CDCl_3$) δ: 165.49, 165.20 (C=O), 138.2, 137.9, 137.6, 133.5, 133.5, 129.8, 129.7, 129.5, 129.4, 128.5, 128.4, 127.9, 127.8, 127.8, 127.7, 114.9, 106.3, 106.1, 83.5, 83.4, 83.0, 82.2, 81.9, 81.6, 72.5, 72.3, 67.0, 65.8, 62.0, 30.5, 28.8. MS MALDI: Calcd for $C_{43}H_{46}O_{11}$ 738.30, Found 761.3 ($M+Na^+$).

Example 12

Preparation of Compound 12a

Compound 11b (182 mg, 0.25 mmol) was coupled with compound 4 under standard glycosylation conditions (Jayaprakash, K N and Fraser-Reid, B., *Synlett*, 2004 301-305; Lu, J and Fraser-Reid, B, *Chem. Commun.* 2005, 862-864) to give compound 12a (222 mg, 69%). $^1$H NMR (300 MHz, $CDCl_3$) δ: 7.09-8.04 (m, 40H), 5.73-5.86 (m, 1H —CH=$CH_2$), 5.43 (d, J=0.9 Hz, 1H), 5.39 (s, 2H), 5.28 (s, 1H), 5.25 (s, 1H), 5.13 (s, 11H), 4.95 (m, 2H), 4.79 (d, J=12.3 Hz, 1H), 4.63 (dd, J=3.3 Hz, J=12 Hz, 1H), 4.99 (d, J=15.3 Hz, 11H), 4.43 (m, 1H), 4.32 (m, 1H), 4.12 (m, 5H), 3.92 (dd, J=4.2 Hz, J=11.4 Hz, 1H), 3.84 (dd, J=3.9 Hz, J=11.4 Hz, 1H), 3.74 (m, 6H), 3.47 (m, 1H), 2.10-2.18 (m, 2H), 1.67-1.76 (m, 2H), 0.97 (s, 9H). $^{13}$C NMR (75 MHz, $CDCl_3$) δ: 165.5, 165.3, 165.2 (C=O), 138.2, 137.9, 137.9, 137.9, 137.7, 135.6, 135.6, 133.3, 133.3, 129.9, 129.8, 129.7, 129.7, 129.6, 128.5, 128.5, 128.4, 128.3, 127.9, 127.7, 127.7, 127.6, 127.6, 114.9, 106.2, 106.1, 83.9, 83.4, 83.1, 82.3, 82.2, 82.0, 81.7, 72.5, 72.3, 72.1, 67.0, 65.8, 65.4, 63.2, 30.5, 28.9, 27.0, 19.5.

Example 13

Preparation of Compound 12b

Compound 12a (220 mg, 0.17 mmol) was desilylated to give compound 12b (147 mg, 82%) according to the procedure as described for compound 7b. $^1$H NMR (300 MHz, $CDCl_3$) δ: 7.17-8.03 (m, 30H, Ar—H), 5.73-5.86 (m, 1H, —CH=$CH_2$) 5.42 (d, J=11.4 Hz, 2H), 5.34 (s, 1H), 5.28 (s, 1H), 5.22 (s, 1H), 5.13 (s, 1H), 4.95 (m, 2H), 4.76 (d, J=11.7 Hz, 1H), 4.62 (t, J=11.7, 11.7 Hz, 2H), 452 (d, J=9 Hz, 1H), 4.42 (m, 2H), 4.32 (m, 1H), 3.47-4.22 (m, 13H), 2.10-2.18 (m, 2H), 1.67-1.76 (m, 2H). $^{13}$C NMR (75 MHz, $CDCl_3$) δ: 165.5, 165.3, 165.2 (C=O), 138.2, 137.9, 137.9, 137.6, 133.5, 129.8, 127.7, 129.5, 129.5, 129.4, 128.5, 128.4, 128.4, 128.3, 217.9, 127.8, 127.7, 127.7, 127.6, 114.9, 106.3, 106.2, 107.1, 83.5, 83.5, 83.4, 83.0, 82.3, 82.1, 81.9, 81.6, 72.5, 72.3, 67.0, 65.9, 65.7, 62.0, 30.5, 28.9. MS MALDI: Calcd for $C_{62}H_{64}O_{16}$ 1064.4 Found 1087.7 ($M+Na^+$).

Example 14

Preparation of Compound 13

Compound 12b (147 mg, 0.138 mmol) was coupled with 4 to give compound 13 (178 mg, 79%) according to the procedure as described for compound 7a. $^1$H NMR (300 MHz, CDCl$_3$) δ: 7.06-8.03 (m, 50H, Ar—H), 5.73-5.86 (m, 1H), 5.12-5.43 (m, 7H), 4.90-5.04 (m, 2H), 4.79 (d, J=12 Hz, 1H), 4.36-4.64 (m, 9H), 4.5-4.20 (m, 6H), 3.61-3.95 (m, 10H), 3.42-3.51 (m, 1H), 2.10-2.17 (m, 2H), 1.66-1.76 (m, 2H), 0.96 (s, 9H). $^{13}$C NMR (75 MHz, CDCl$_3$) δ: 165.5, 165.3, 165.2, 165.2 (C=O), 138.3, 137.9, 137.9, 137.7, 153.6, 133.3, 129.9, 129.8, 129.8, 129.6, 129.5, 128.5, 128.5, 128.4, 128.3, 128.3, 127.9, 127.8, 127.7, 127.7, 127.6, 127.6, 114.9, 106.2, 106.1, 83.9, 83.4, 83.3, 82.3, 82.2, 82.0, 81.9, 81.7, 72.5, 72.3, 72.2, 72.1, 67.0, 65.8, 65.6, 65.4, 63.2, 30.5, 28.9, 26.9, 19.5. MS MALDI: Calcd for C$_{97}$H$_{100}$O$_{21}$Si 1628.6, Found 1652.8 (M+Na$^+$)

Example 15

Preparation of Compound 15 (Formula V)

Compound 13 was coupled to donor 14 to give compound 15 according to the same procedure as described for compound 11a.

Example 16

Preparation of Compound 17

Acceptor 9 was coupled with excess (e.g. 3 equivalents) of donor 4 to give compound 16 (using the same strategy as described above in Example 10), which underwent desilylation to give compound 17 (using the same strategy as described above in Example 7). $^1$H NMR (300 MHz, CDCl$_3$) δ 7.95-8.02 (m, 6H), 7.16-7.58 (m, 29H), 5.79 (m, 1H), 5.19-5.53 (m, 6H), 4.81-5.10 (m, 3H), 4.21-4.67 (m, 7H), 3.39-4.04 (m, 10H), 2.14 (m, 2H), 1.73 (m, 2H). $^{13}$C NMR (75 MHz, CDCl$_3$) δ 165.70, 165.28, 165.25, 138.27, 137.66, 137.51, 133.54, 133.48, 133.35, 129.93, 129.82, 128.60, 128.55, 128.53, 128.49, 127.95, 127.91, 127.88, 127.81, 115.03, 106.01, 105.93, 105.70, 83.93, 83.60, 83.35, 83.06, 81.94, 81.82, 81.21, 80.18, 72.51, 72.23, 66.93, 65.01, 62.96, 62.82, 30.50, 28.88.

Example 17

Preparation of Compound 18

Compound 18 was prepared from compound 17 according to the same procedure as described for compound 16. $^1$H NMR (300 MHz, CDCl$_3$) δ 7.86-8.01 (m, 10H), 7.08-7.59 (m, 55H), 5.77 (m, 1H), 5.12-5.48 (m, 10H), 4.32-5.04 (m, 14H), 3.96-4.20 (m, 7H), 3.62-3.91 (m, 10H), 3.45 (m, 1H), 2.12 (m, 2H), 1.70 (m, 2H), 0.93 (s, 9H), 0.92 (s, 9H). $^{13}$C NMR (75 MHz, CDCl$_3$) δ 165.62, 165.37, 165.29, 165.22, 1655.19, 138.36, 138.09, 138.01, 137.85, 135.64, 133.32, 133.23, 129.98, 129.93, 129.87, 129.70, 129.58, 128.51, 128.45, 128.34, 128.29, 127.83, 127.74, 127.56, 127.50, 114.95, 106.37, 106.18, 105.93, 105.56, 83.93, 83.90, 83.31, 82.99, 82.86, 82.51, 82.02, 81.62, 80.49, 72.41, 72.28, 72.02, 66.82, 65.95, 65.25, 63.12, 30.49, 28.91, 27.01, 19.53.

Example 18

Preparation of Compound 19 (Formula VI)

Compound 19 was prepared by double glycosylation of compound 18 with donor 14, according to the same procedure as described as compound 15.

Example 19

Preparation of Compound 20

Compound 17 was double glycosylated with donor 14 (using the same strategy as used above for preparation of compound 19) to give compound 20. $^1$H NMR (300 MHz, CDCl$_3$) δ 7.79-8.06 (m, 10H), 7.07-7.51 (m, 55H), 5.78 (m, 1H), 5.16-5.58 (m, 9H), 4.29-5.04 (m, 22H), 3.43-4.17 (m, 22H), 2.14 (m, 2H), 1.72 (m, 2H). $^{13}$C NMR (75 MHz, CDCl$_3$) δ 165.66, 165.48, 165.41, 165.29, 138.51, 138.45, 138.32, 138.00, 137.69, 137.60, 133.52, 133.31, 133.17, 133.10, 130.02, 129.94, 129.86, 129.47, 128.68, 128.46, 128.42, 128.31, 128.25, 128.15, 128.05, 127.79, 127.84, 127.57, 114.99, 106.35, 105.96, 105.45, 100.32, 98.42, 83.20, 82.73, 81.99, 81.64, 80.58, 78.62, 75.35, 74.21, 73.58, 72.45, 72.26, 71.96, 71.56, 68.98, 68.80, 66.88, 66.35, 30.48, 28.88.

Example 20

Preparation of Compounds 21a and 21b

To a solution of compound 20 in CH$_3$CN containing approximately 10% water was added NBS (about 3 molar excess). The mixture was stirred at r.t. for 1 h or until completion (TLC). Aqueous Na$_2$S$_2$O$_3$ solution (10%) was added to quench the reaction. The aqueous phase was extracted with CH$_2$Cl$_2$, and the organic phase was dried and evaporated. The residue was purified by column chromatography to give compound 21a. This material was mixed with a generous excess (approximately 5 fold) of Cl$_3$CCN in CH$_2$Cl$_2$ at 0° C., and DBU (2 drops) was added. The solution was stirred at 0° C. for 1 h or until completion (TLC). Aqueous NH$_4$Cl solution was added. The aqueous phase was extracted with CH$_2$Cl$_2$. The organic phase was dried and was evaporated. The residue was purified by column chromatography (Hexane: EtOAc: Et$_3$N 3:1:0.1) to give compound 21b, which was used immediately.

Example 21

Preparation of Compound 22

Compound 12b (213 mg, 0.2 mmol) was coupled with donor 6 (210 mg, 0.44 mmol) to give tetrasaccharide which was subjected to de-acylation with thiourea to give compound 22. $^1$H NMR (300 MHz, CDCl$_3$) δ 7.93-8.02 (m, 8H), 7.18-7.53 (m, 2H), 5.78 (m, 1H), 5.12-5.49 (m, 7H), 4.75-5.03 (m, 4H), 4.31-4.66 (m, 7H), 3.46-4.18 (m, 16H), 2.12 (m, 2H), 1.71 (m, 2H). $^{13}$C NMR δ 166.61, 165.53, 165.29, 165.22, 138.26, 137.88, 137.56, 133.73, 133.52, 133.35, 129.85, 129.81, 129.54, 129.01, 128.60, 128.38, 128.34, 127.94, 127.91, 127.79, 127.72, 127.64, 114.91, 106.28, 106.22, 106.09, 105.32, 86.23, 84.19, 83.39, 83.13, 82.30, 82.13, 81.99, 81.92, 81.63, 76.48, 72.51, 72.29, 72.07, 66.97, 66.03, 65.74, 61.91, 30.47, 28.86.

Example 22

Preparation of Compound 23

Compound 22 was coupled with donor 4 followed by desilylation (using the same strategy as described above in Example 7) to give compound 23. $^1$H NMR (300 MHz, CDCl$_3$) δ 7.94-8.03 (m, 12H), 7.11-7.54 (m, 48H), 5.78 (m, 1H), 5.13-5.51 (m, 12H), 4.91-5.03 (m, 2H), 4.43-4.79 (m, 10H), 4.10-4.36 (m, 9H), 3.43-3.98 (m, 16H), 2.12 (m, 2H), 1.71 (m, 2H). $^{13}$C NMR (75 MHz, CDCl$_3$) δ 165.46, 165.42, 165.24, 165.19, 165.12, 164.96, 138.18, 137.79, 137.72, 137.43, 137.24, 165.12, 164.96, 138.18, 137.79, 137.72, 137.43, 137.34, 133.48, 133.35, 133.28, 1329.79, 129.70, 129.46, 129.39, 128.48, 128.34, 128.27, 127.86, 127.79, 127.76, 127.74, 127.71, 127.66, 127.59, 114.86, 106.75, 106.11, 105.98, 105.92, 105.53, 98.31, 83.74, 83.54, 83.40, 83.31, 83.28, 83.13, 82.84, 82.24, 82.12, 81.95, 81.89, 81.75, 81.65, 81.60, 81.44, 79.85, 72.42, 72.33, 72.20, 71.97, 67.34, 66.87, 65.62, 64.57, 62.70, 33.31, 30.39, 28.78, 23.59.

Example 23

Preparation of Compound 24 (Formula VII)

To a solution of acceptor 23 (0.028 mmol) and donor 21b (0.07 mmol) in Et$_2$O (5 mL) at r.t. was added TESOTf (5 μL). The mixture was stirred at r.t. for 20 min. Triethylamine (0.3 mL) was added to quench the reaction. The solvent was evaporated. The residue was purified by column chromatography (Hexane/EtOAc 1:1) to give compound 24 in 75% yield.

Example 24

Preparation of Compound 25a

Compound 25a was prepared according to the same procedure as described for compound 16. $^1$H NMR (300 MHz, CDCl$_3$) δ 7.86-8.01 (m, 10H), 7.08-7.59 (m, 55H), 5.77 (m, 1H), 5.12-5.48 (m, 10H), 4.32-5.04 (m, 14H), 3.96-4.20 (m, 7H), 3.62-3.91 (m, 10H), 3.45 (m, 1H), 2.12 (m, 2H), 1.70 (m, 2H), 0.93 (s, 9H), 0.92 (s, 9H). $^{13}$C NMR (75 MHz, CDCl$_3$) δ 165.62, 165.37, 165.29, 165.22, 1655.19, 138.36, 138.09, 138.01, 137.85, 135.64, 133.32, 133.23, 129.98, 129.93, 129.87, 129.70, 129.58, 128.51, 128.45, 128.34, 128.29, 127.83, 127.74, 127.56, 127.50, 114.95, 106.37, 106.18, 105.93, 105.56, 83.93, 83.90, 83.31, 82.99, 82.86, 82.51, 82.02, 81.62, 80.49, 72.41, 72.28, 72.02, 66.82, 65.95, 65.25, 63.12, 30.49, 28.91, 27.01, 19.53.

Example 25

Preparation of Compound 26a

Acceptor 23 (358 mg, 0.183 mmol) and donor 25c (1.09 g, 0.46 mmol) were dissolved in CH$_2$Cl$_2$ (2 mL). Molecular sieves and Yb(OTf)$_3$ (20 mg, 0.046 mmol) were added. The mixture was stirred under Argon at r.t. for 30 min. Et$_3$N (0.5 mL) was added to quench the reaction. The molecular sieves were filtered off. The solvent was evaporated. The residue was purified by column chromatography (EtOAc:Hexane 1:2) to give compound 26a (817 mg, 73%). $^1$H NMR (300 MHz, CDCl$_3$) δ 7.88-8.02 (m, 32H), 6.98-7.57 (m, 148H), 5.77 (m, 1H), 4.90-5.44 (m, 34H), 3.41-4.76 (m, 90H).

Example 25

Preparation of Compound 26b

Compound 26a was subjected to desilylation to give compound 26b (using the same strategy as described above in Example 7). $^1$H NMR (300 MHz, CDCl$_3$) δ 7.88-8.03 (m, 32H), 7.05-7.5_(m, 108H), 5.78 (m, 1H), 5.11-5.49 (m, 31H), 4.90-5.04 (m, 2H), 3.60-4.77 (m, 91H), 2.12 (m, 2H), 1.78 (m, 2H). $^{13}$C NMR (75 MHz, CDCl$_3$) δ 165.53, 165.31, 165.29, 165.27, 165.22, 165.14, 165.11, 165.07, 165.03, 165.00, 138.26, 137.90, 137.81, 137.60, 137.56, 133.45, 133.33, 133.29, 133.26, 133.18, 133.10, 133.05, 127.85, 129.70, 129.52, 129.45, 129.38, 128.51, 128.46, 128.38, 128.31, 128.25, 128.19, 127.89, 127.87, 127.82, 127.75, 127.69, 127.55, 127.34, 114.86, 106.40, 106.32, 106.23, 106.16, 106.10, 106.02, 105.92, 105.45, 105.36, 105.26, 98.41, 83.66, 83.48, 83.33, 82.88, 82.28, 81.96, 81.72, 72.48, 72.31, 72.11, 71.86, 67.44, 66.91, 65.67, 65.52, 61.97, 60.55, 33.38, 30.45, 28.83.

Example 26

Preparation of Compound 27

Acceptor 26b (94 mg, 0.0187 mmol) was coupled with Donor 21b (240 mg, 0.112 mmol) to give compound 27 (180 mg, 78%) according to the same procedure as described for compound 18. $^1$H NMR (300 MHz, CDCl$_3$) δ 7.90-8.02 (m, 72H), 7.02-7.49 (m, 333H), 5.78 (m, 1H), 5.02-5.57 (m, 68H), 4.88-4.97 (m, 13H), 3.42-4.78 (m, 237H), 2.12 (m, 2H), 1.70 (m, 2H). $^{13}$C NMR (75 MHz, CDCl$_3$) δ 165.58, 165.43, 165.36, 165.29, 165.25, 165.16, 165.08, 165.04, 138.61, 138.56, 138.49, 138.47, 138.32, 138.01, 137.95, 137.88, 137.86, 137.62, 133.49, 133.42, 133.33, 133.13, 133.05, 130.01, 129.90, 129.83, 129.70, 129.48, 128.69, 128.63, 128.56, 128.43, 128.39, 128.31, 128.26, 128.23, 128.05, 128.01, 127.96, 127.91, 127.85, 127.76, 127.62, 127.53, 127.50, 114.89, 106.51, 106.17, 105.16, 98.44, 83.40, 83.33, 83.07, 82.53, 82.42, 82.29, 82.09, 81.99, 81.88, 81.72, 79.99, 78.74, 78.64, 75.36, 75.30, 74.20, 74.11, 73.56, 73.52, 72.54, 72.47, 72.33, 72.22, 72.13, 71.99, 71.51, 69.01, 68.80, 68.72, 66.95, 66.26, 65.99, 65.71, 65.47, 30.50, 28.90.

Example 27

General Procedure for the Preparation of Compounds 28-38

Compound 28-38 were further functionalized according to standard procedures.

The foregoing is illustrative of the present invention, and is not to be construed as limiting thereof. The invention is defined by the following claims, with equivalents of the claims to be included therein.

That which is claimed is:
1. A compound of formula IV:
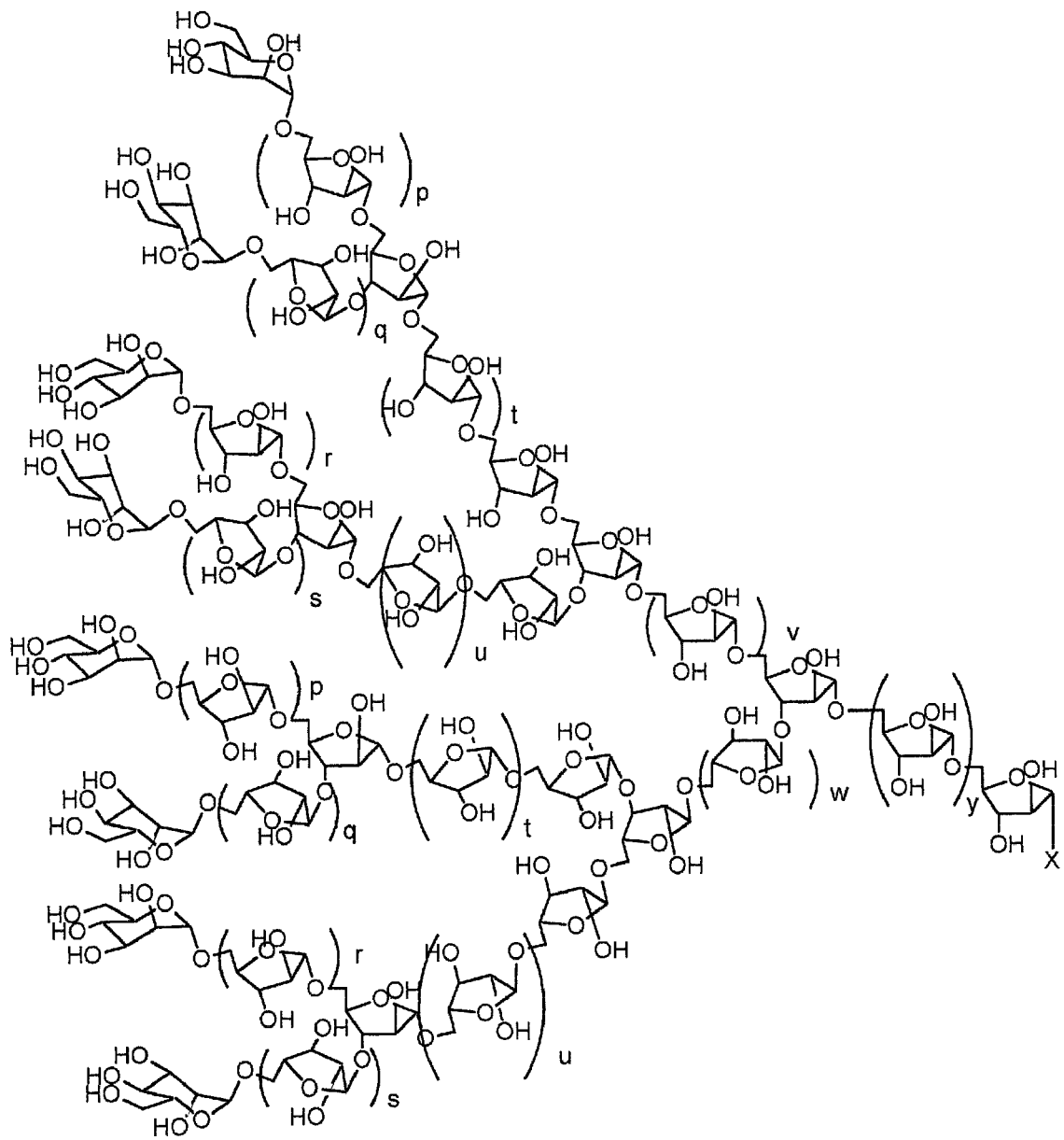
wherein each p, q, r, s, t, u, v, w, and y are each independently an integer from 1 to 20; and
X is a attachment group;
or a salt thereof 2. The compound of claim 1, wherein X is selected from the group consisting of:

a) $OCH_2(CH_2)_oCH_2SH$,
b) $OCH_2(CH_2)_oCHCH_2OCOR'$
                  |
                  $OCOR'$,
c) $OCH_2(CH_2)_oCOOH$,
d) $OCH_2(CH_2)_oCH_2NH_2$,
e) $OCH_2(CH_2)_oCH_2Ophosphodiacylglyceryl$, and
f) $OCH_2(CH_2)_oCH_2NH_2$-Biotin, wherein o is a integer from 1 to 20 and R' is a alkyl, aryl, alkyl aryl, or aryl alkyl.

3. The compound of claim 1, wherein each p, q, r, s, t, u, v, w and y is each 1.

4. A compound of formula VIII

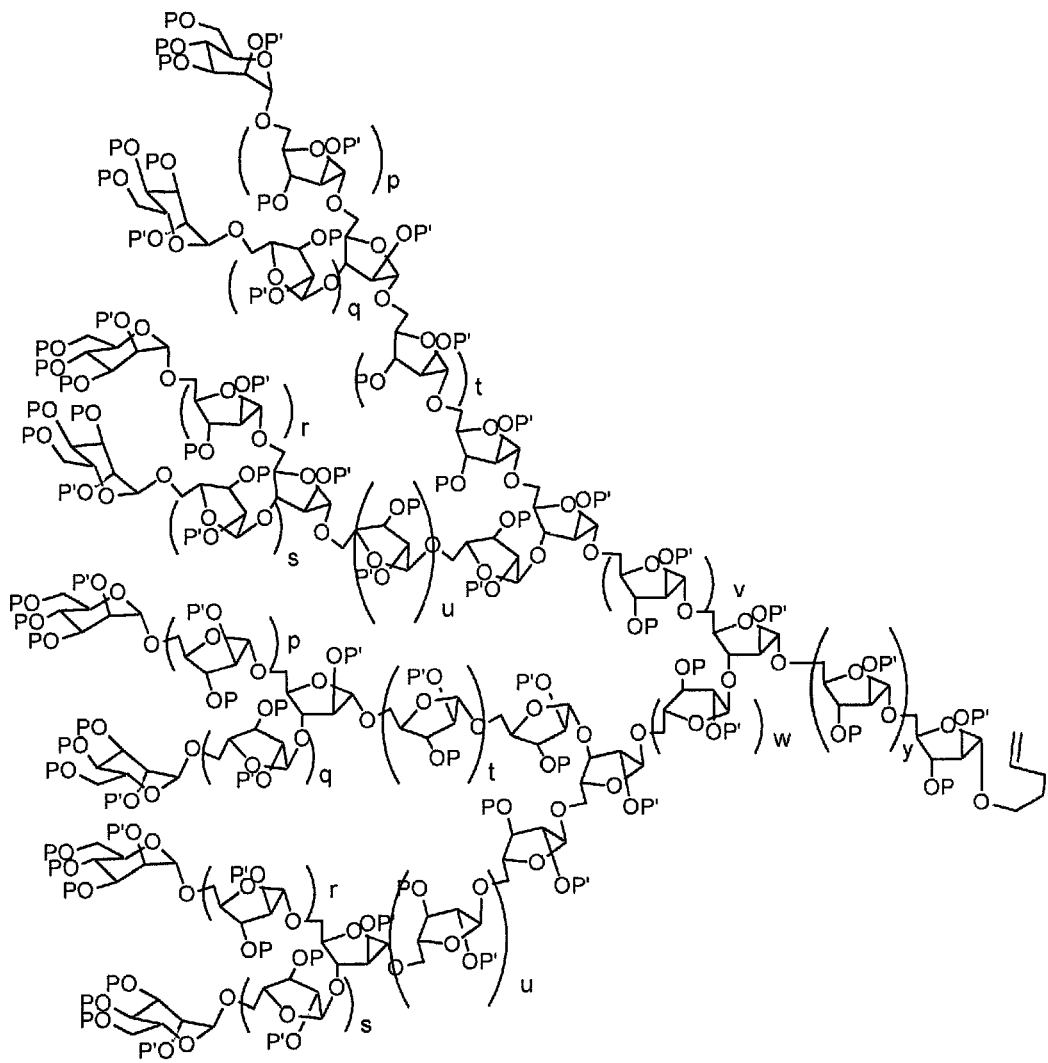

wherein P and P' are hydroxyl protecting groups and each p, q, r, s, t, u, v, w and y is each independently an integer from 1 to 20.

5. The compound of claim 4, wherein P is Bn and P' is Bz.
6. The compound of claim 4, wherein each p, q, r, s, t, u, v, w and y is each 1.
7. A method of making a compound of claim 4
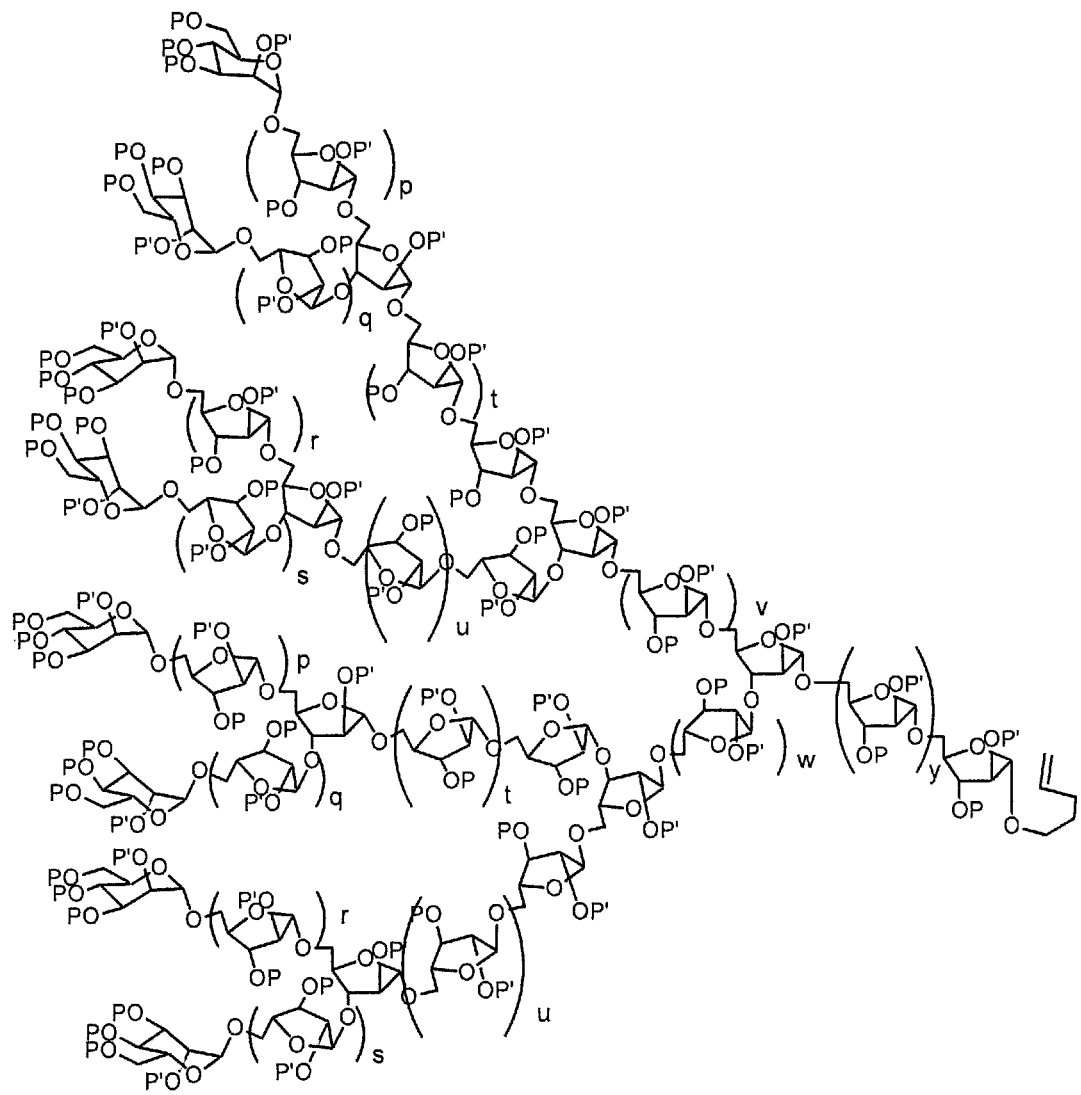

comprising:
(a) reacting a compound of formula 17
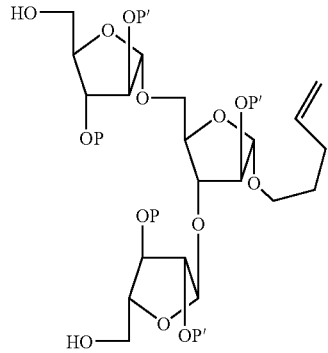
with a compound of formula 4
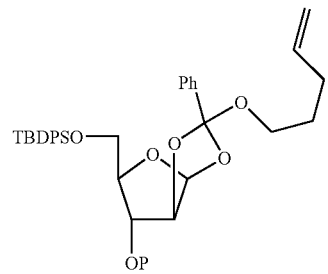
to produce a compound of formula 25a
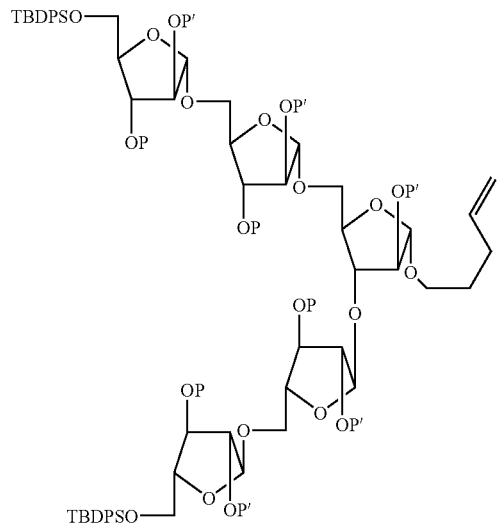
(b) hydrolyzing the compound of formula 25a of step (a) to produce a compound of formula 25b
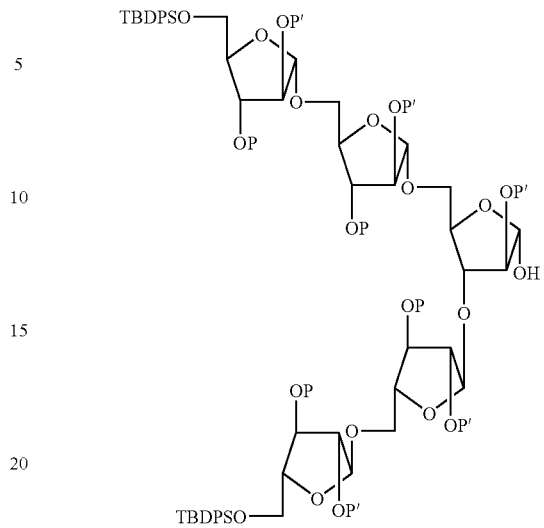
(c) condensing the compound of formula 25b of step (b) to produce a compound of formula 25c
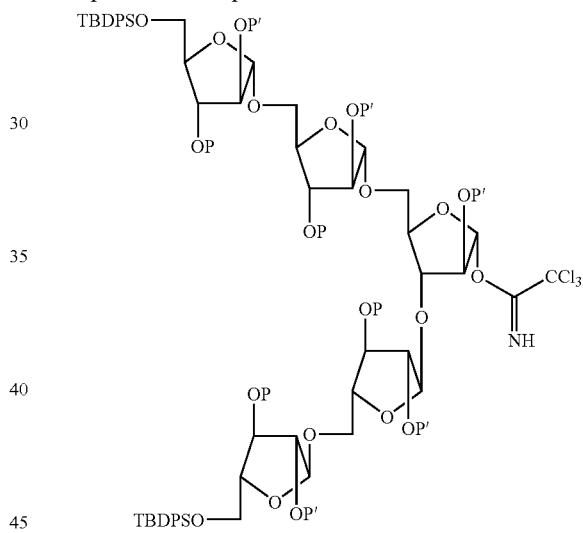
(d) reacting a compound of formula 23
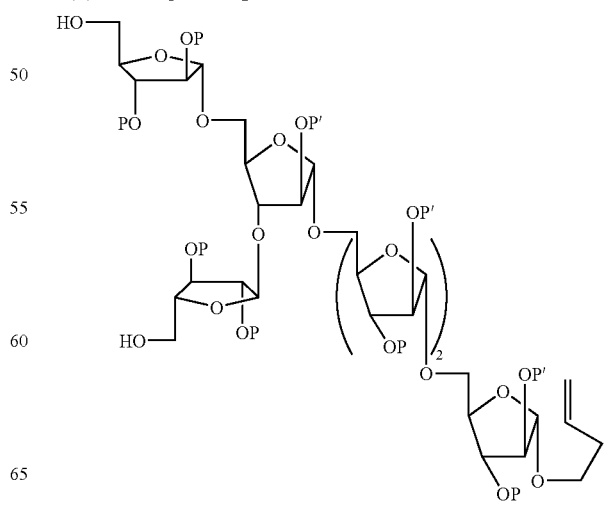

with the compound of formula 25c of step (c) to produce a compound of formula 26a
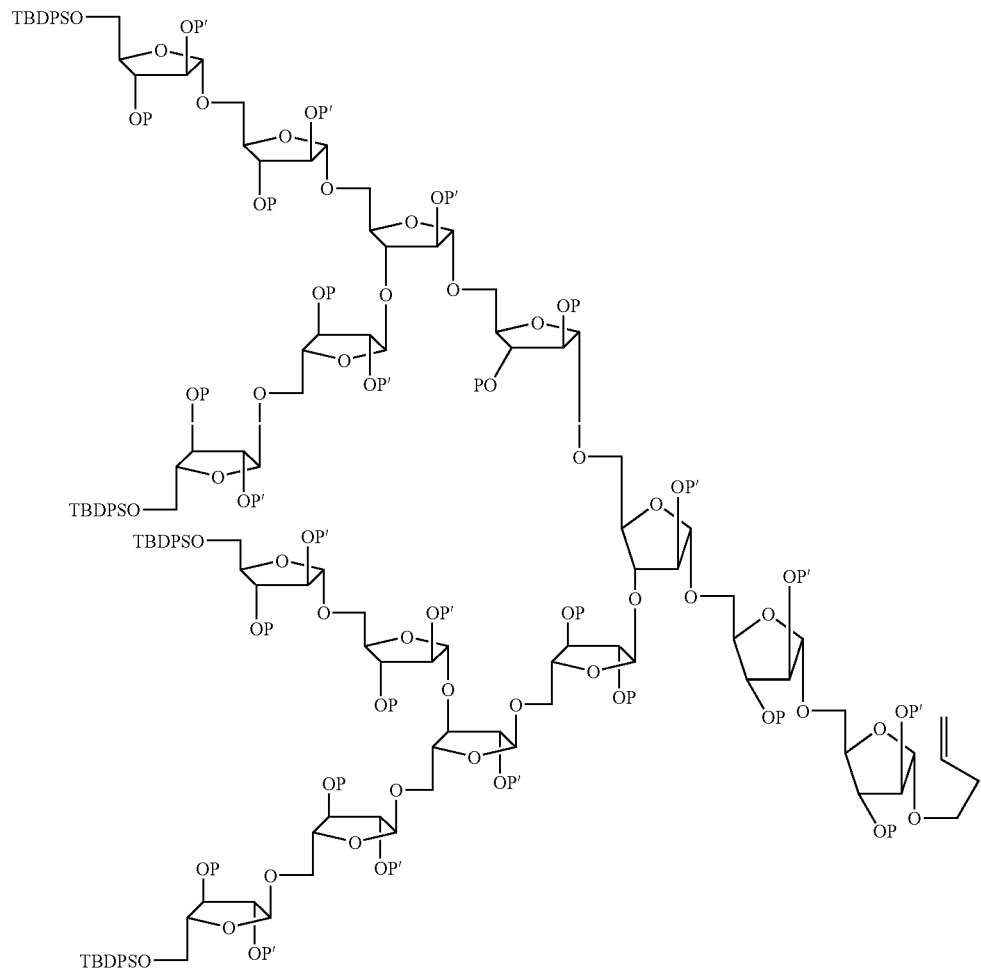
45
(e) desilylating the compound of formula 26a of step (d) with TBAF to produce a compound of formula 26b
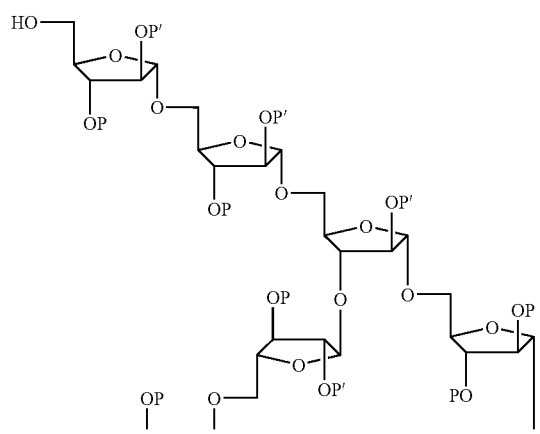

-continued
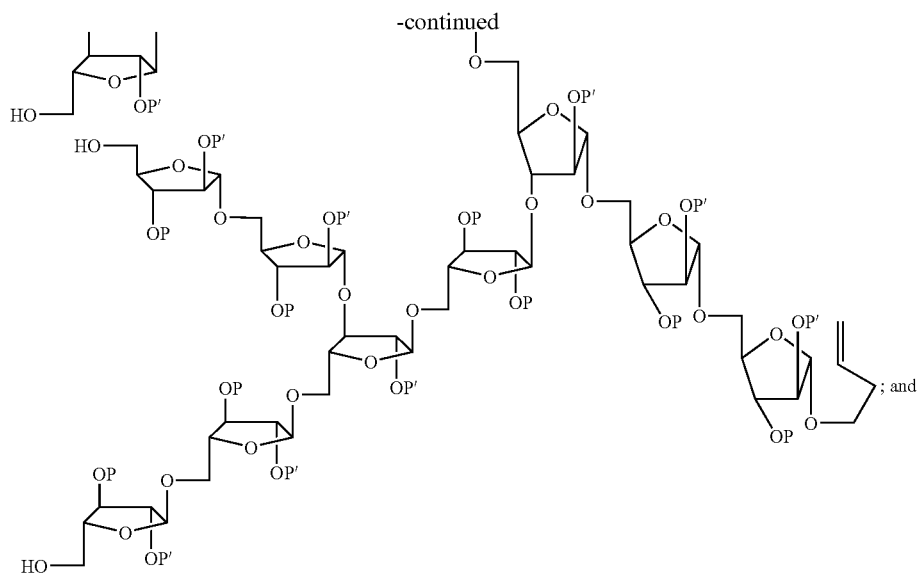
(f) reacting the compound of formula 26b of step (d) with a compound of formula 21b
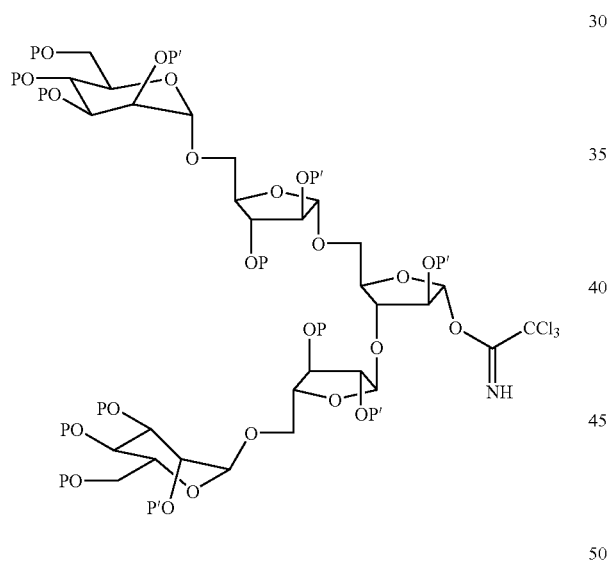
to produce a compound of claim 4.
* * * * *

UNITED STATES PATENT AND TRADEMARK OFFICE
CERTIFICATE OF CORRECTION

PATENT NO. : 7,741,475 B2  Page 1 of 11
APPLICATION NO. : 11/674287
DATED : June 22, 2010
INVENTOR(S) : Fraser-Reid et al.

It is certified that error appears in the above-identified patent and that said Letters Patent is hereby corrected as shown below:

Column 5, lower portion of Formula IV: Please correct

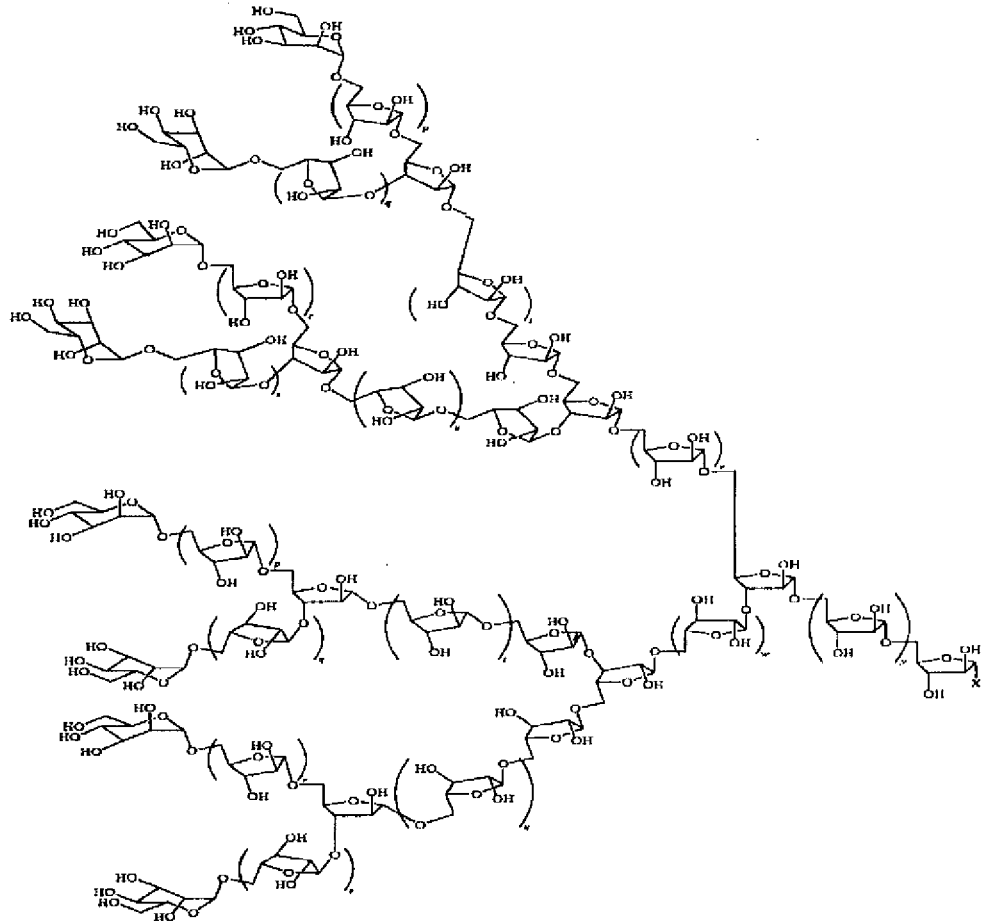

to read:

Signed and Sealed this
First Day of February, 2011

David J. Kappos
*Director of the United States Patent and Trademark Office*

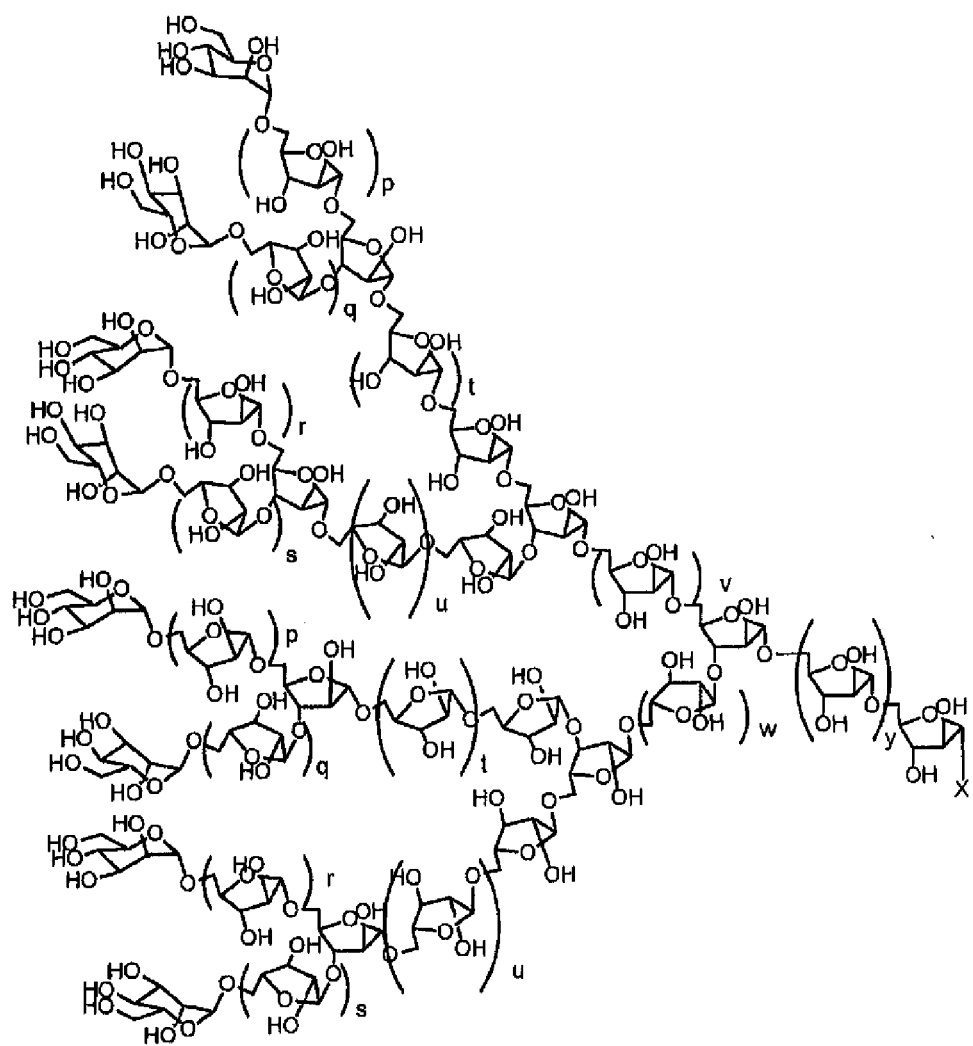

Columns 29-30, Formula IV: Please correct
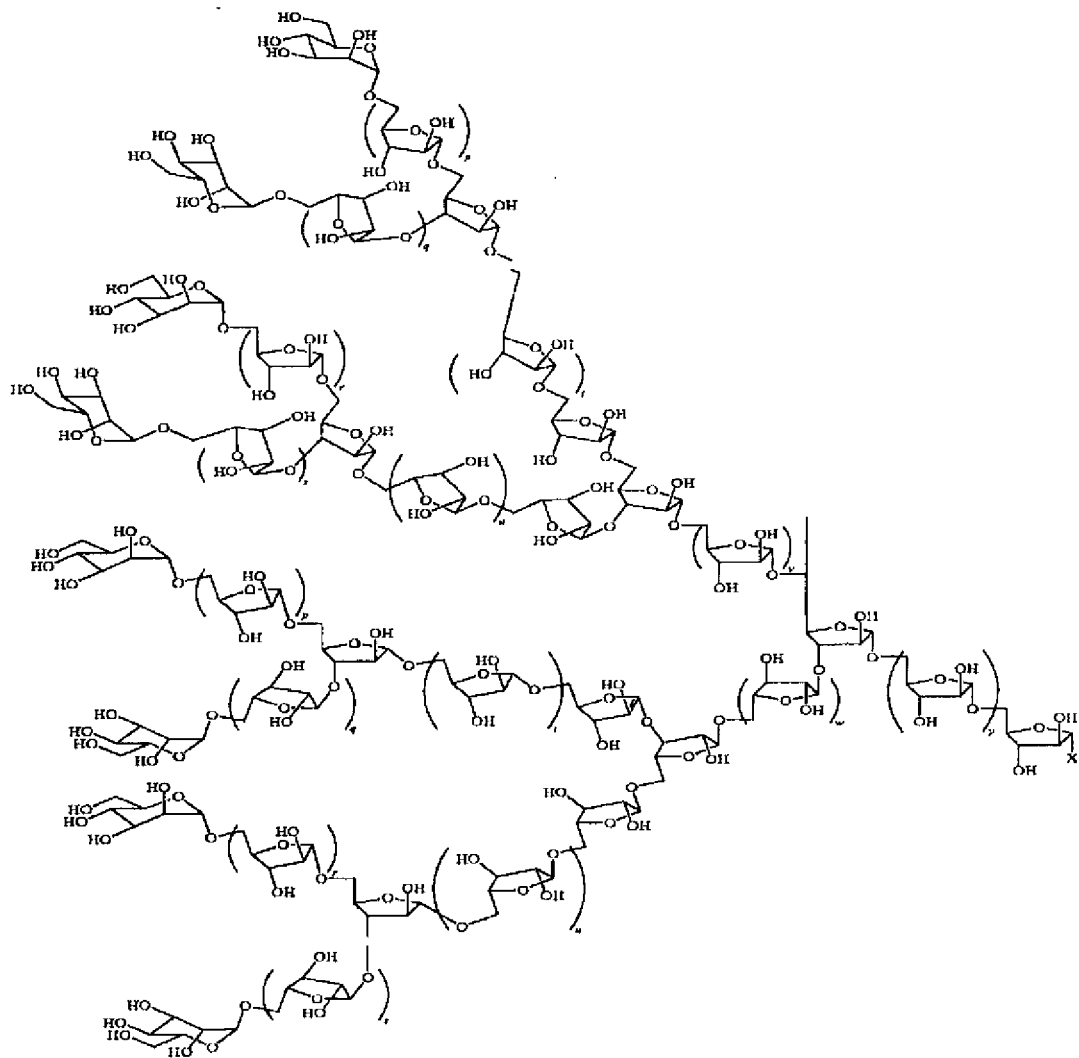
to read:

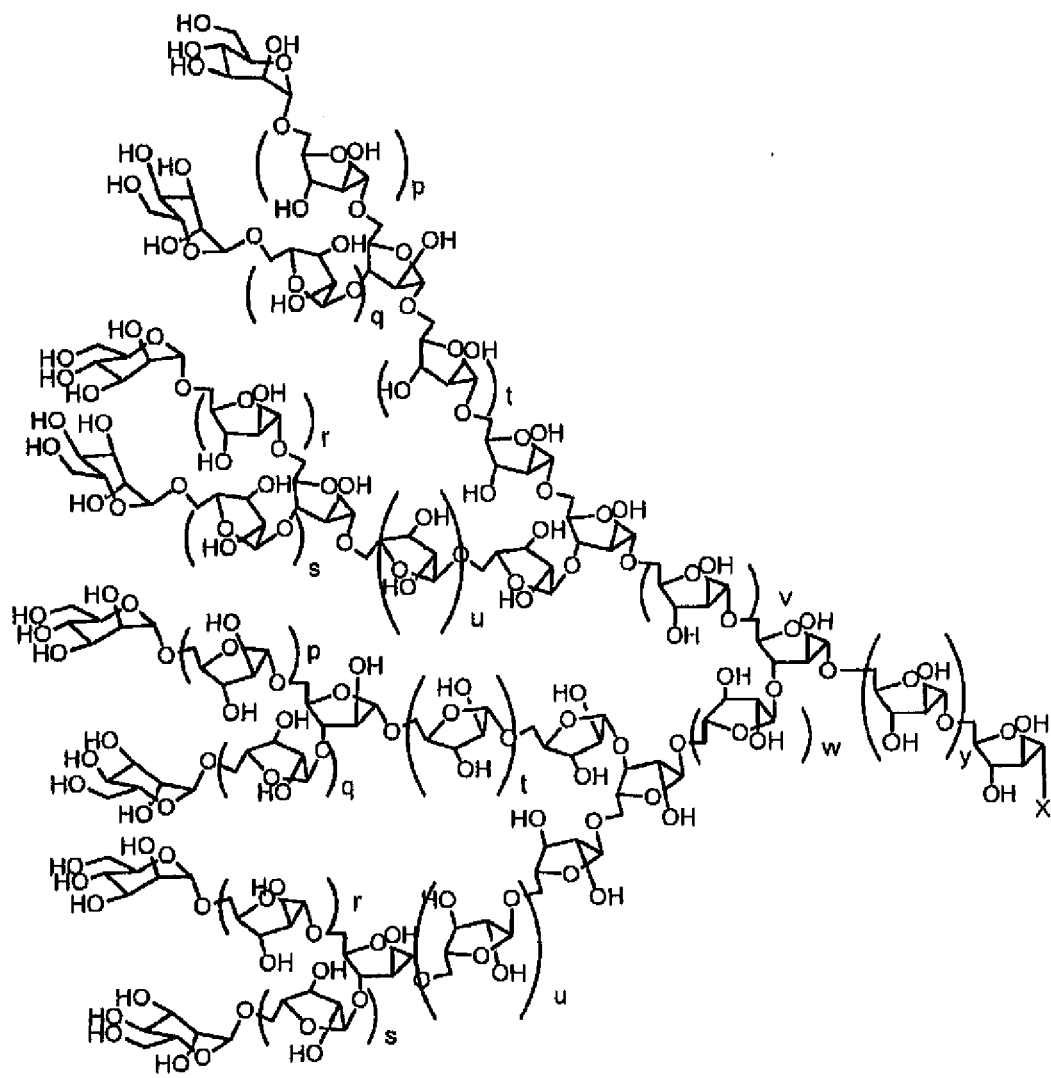

CERTIFICATE OF CORRECTION (continued)
U.S. Pat. No. 7,741,475 B2

Column 37, Scheme 3(a): Please correct the section of Scheme 3(a) presented below:

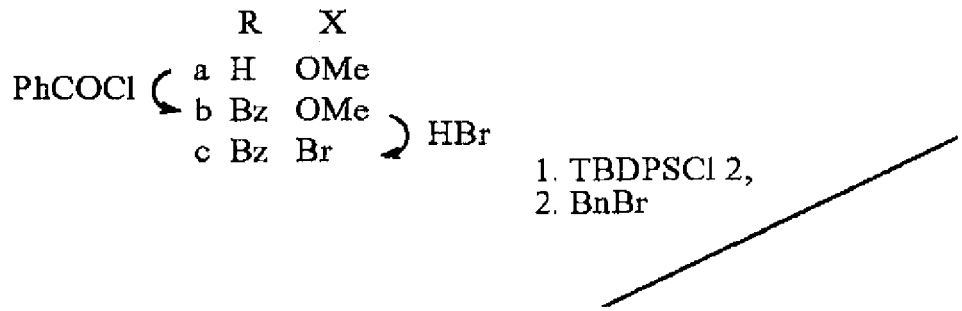

to read:

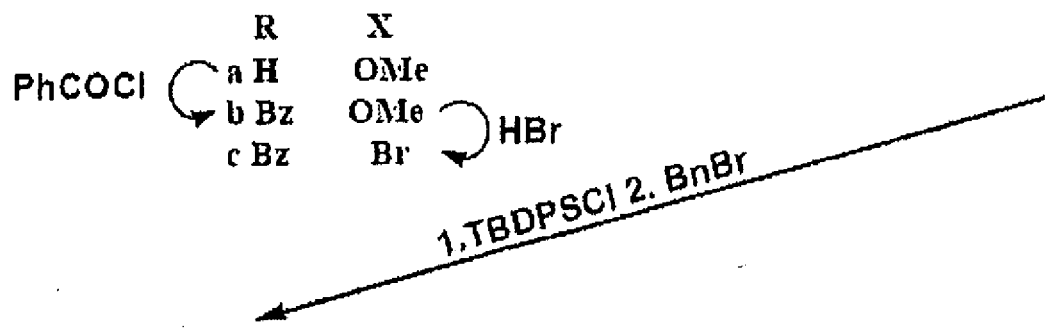

Columns 43 and 44, Scheme 5: Please correct:

CERTIFICATE OF CORRECTION (continued)
U.S. Pat. No. 7,741,475 B2

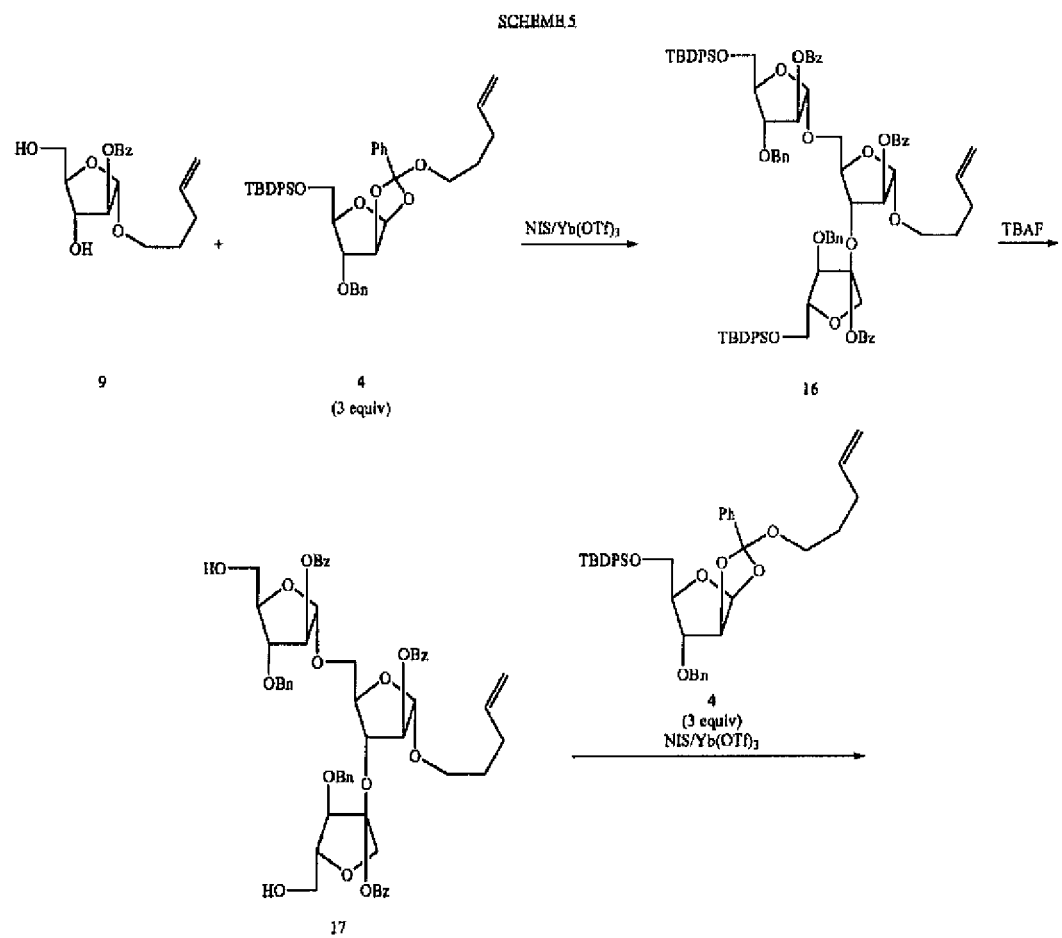

to read:

SCHEME 5
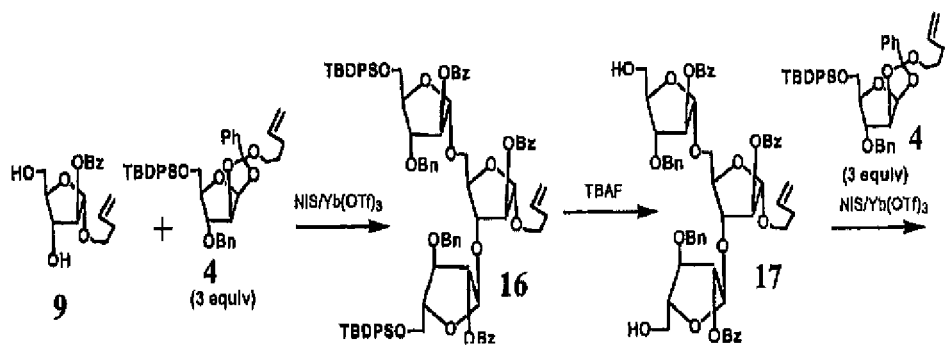
Column 63, Lines 51, 52 and 53: Please correct:
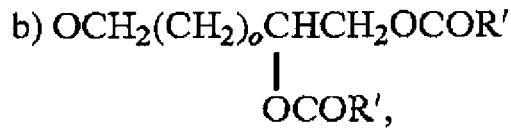
to read:
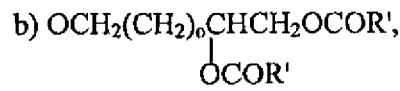
Column 80, Lines 46-65: Please replace:

CERTIFICATE OF CORRECTION (continued)
U.S. Pat. No. 7,741,475 B2

(d) reacting a compound of formula 23

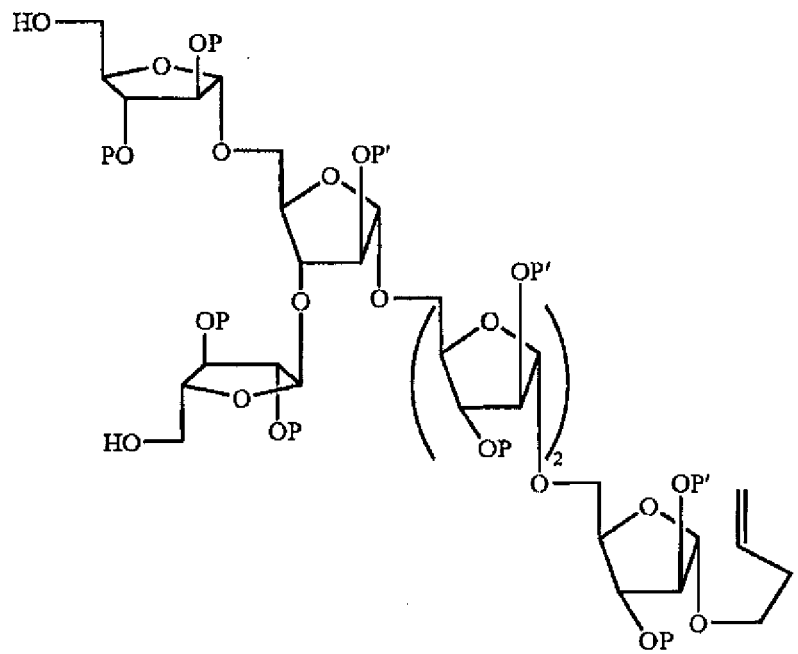

to read:

(d) reacting a compound of formula 23

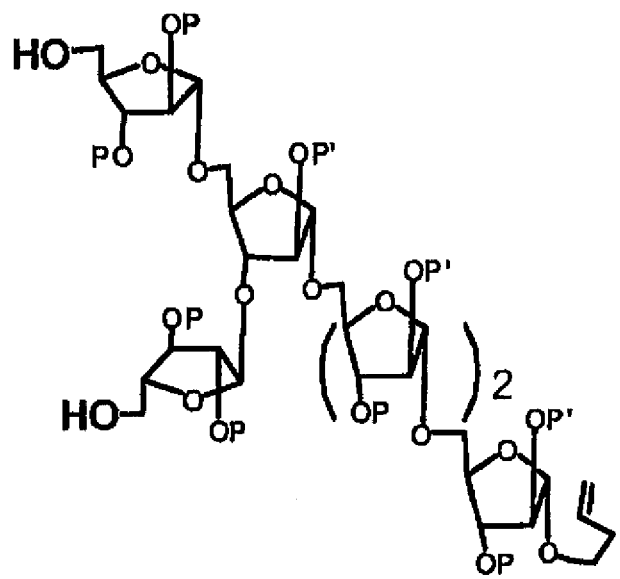

Column 81-82, Compound of Formula 26a: Please replace

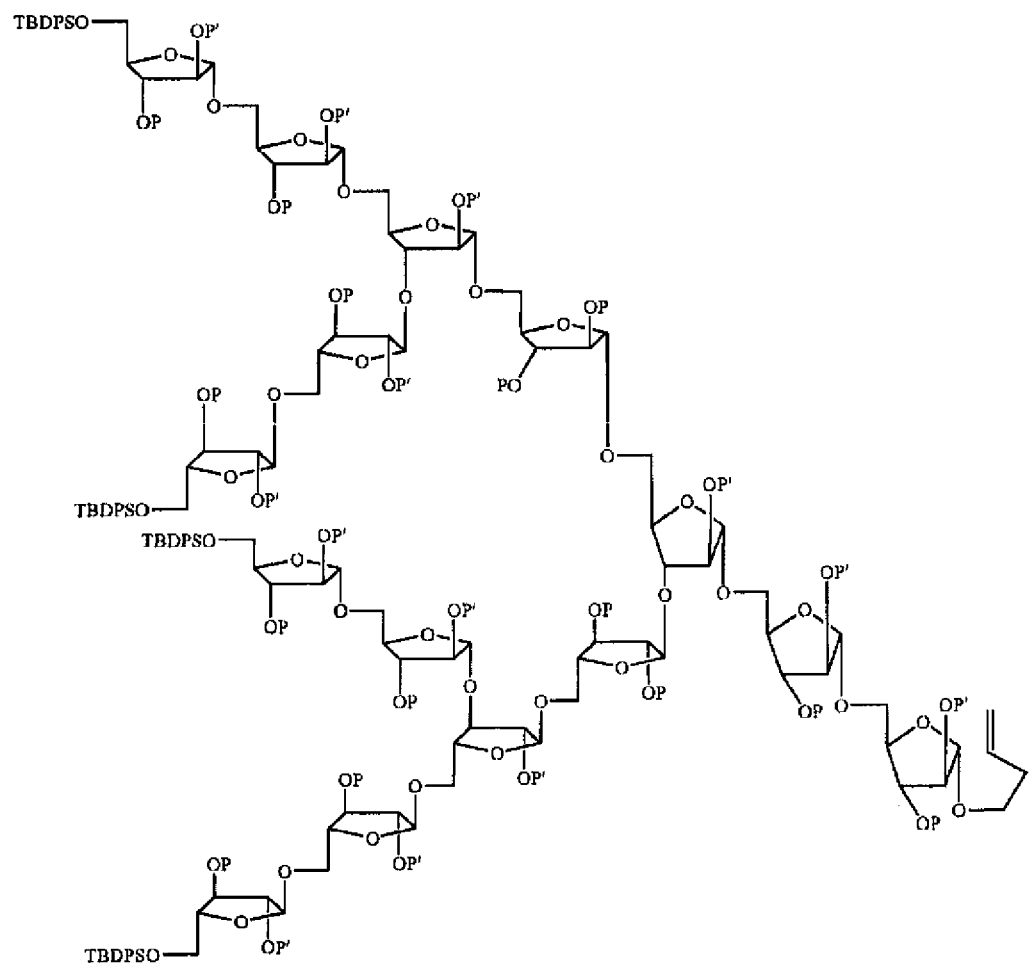
to read:

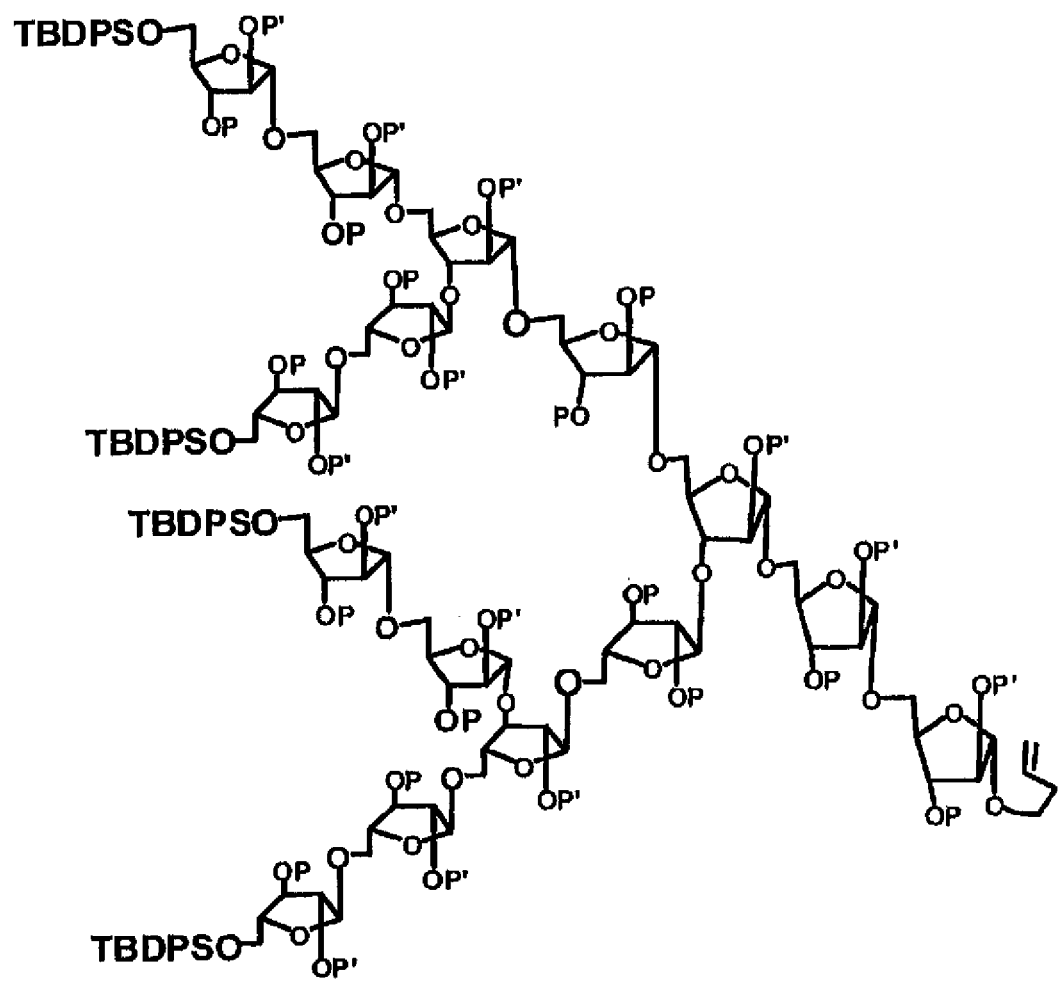
Columns 83-84, -Continued: Please correct:

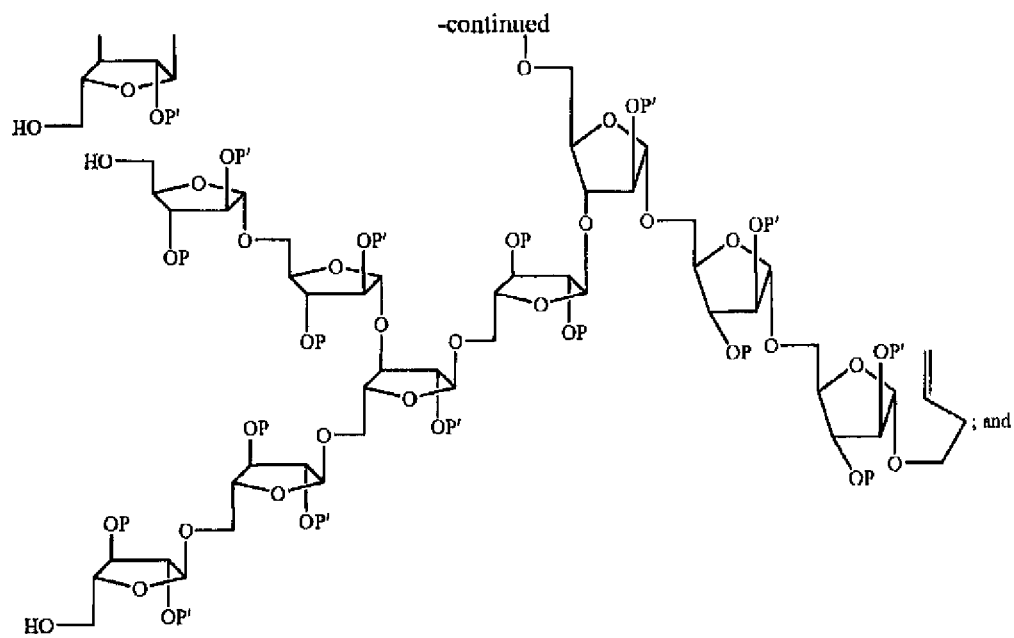
to read:
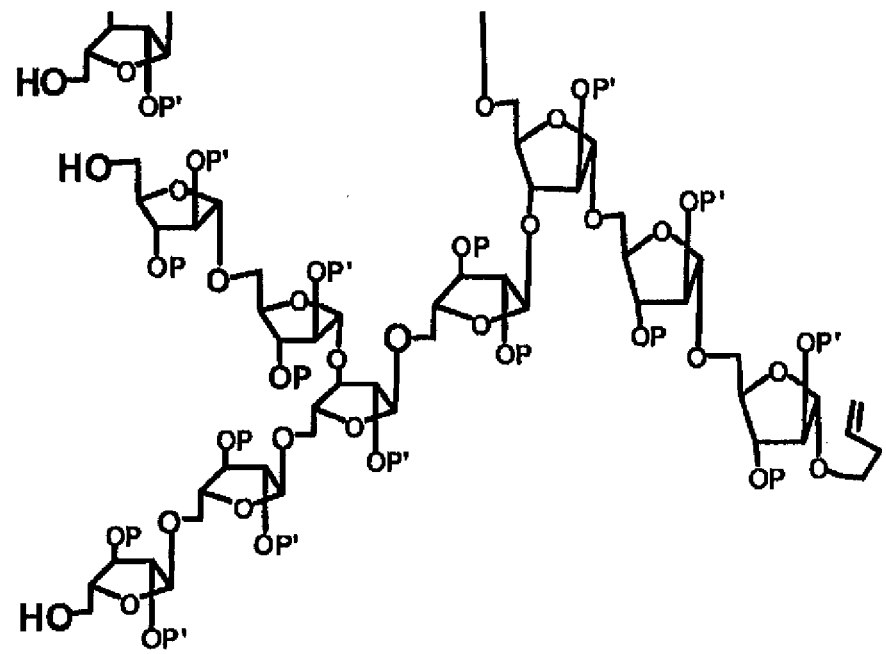
; and